United States Patent
Dupin et al.

(10) Patent No.: US 11,116,763 B2
(45) Date of Patent: Sep. 14, 2021

(54) **MECLOZINE DERIVATIVES AND DICLAZURIL DERIVATIVES FOR USE IN THE PREVENTION AND/OR THE TREATMENT OF DISORDERS ASSOCIATED TO THE INFLAMMATION INDUCED BY *P. ACNES***

(71) Applicants: UNIVERSITÉ DE PARIS, Paris (FR); Assistance Publique—Hopitaux de Paris, Paris (FR); Institut National de la Sante et de la Recherche Medicale (INSERM), Paris (FR); Centre National de la Recherche Scientifique (CNRS), Paris (FR); Sorbonne Universite, Paris (FR)

(72) Inventors: Nicolas Dupin, Paris (FR); Vincent Calvez, Paris (FR); Philippe Grange, Ozoir la Ferriere (FR); Anne-Geneviève Marcelin, Paris (FR)

(73) Assignees: Universite de Paris, Paris (FR); Assistance Publique—Hopitaux de Paris, Paris (FR)

( * ) Notice: Subject to any disclaimer, the term of this patent is extended or adjusted under 35 U.S.C. 154(b) by 0 days.

(21) Appl. No.: 16/317,091

(22) PCT Filed: Jul. 13, 2017

(86) PCT No.: PCT/EP2017/067774
§ 371 (c)(1),
(2) Date: Jan. 11, 2019

(87) PCT Pub. No.: WO2018/011375
PCT Pub. Date: Jan. 18, 2018

(65) Prior Publication Data
US 2019/0224191 A1     Jul. 25, 2019

(30) Foreign Application Priority Data
Jul. 13, 2016  (EP) .................................... 16305912

(51) Int. Cl.
*A61K 31/53* (2006.01)
*A61P 17/10* (2006.01)
(Continued)

(52) U.S. Cl.
CPC ............ *A61K 31/495* (2013.01); *A61K 31/53* (2013.01); *A61K 45/06* (2013.01); *A61P 17/06* (2018.01);
(Continued)

(58) Field of Classification Search
CPC ...... A61K 31/495; A61K 45/06; A61K 31/53; A61K 31/202; A61K 31/203;
(Continued)

(56) References Cited

U.S. PATENT DOCUMENTS

2003/0096815 A1* 5/2003 Hundley ................ A61K 31/00
514/241
2005/0014729 A1 1/2005 Pulaski
(Continued)

FOREIGN PATENT DOCUMENTS

EP    2 589 376         5/2013
JP    2012527315 A      11/2012
(Continued)

OTHER PUBLICATIONS

Apfelbacher et al., *Oral H1 antihistamines as monotherapy for eczema (Review)*, 2 Cochrane Database of Systematic Reviews Art. No. CD007770 (2013).
(Continued)

*Primary Examiner* — Sarah Pihonak
*Assistant Examiner* — Jason Deck
(74) *Attorney, Agent, or Firm* — Panitch Schwarze Belisario & Nadel LLP

(57) ABSTRACT

The present invention relates to compounds of the following general formula (I) or (II) or a pharmaceutically acceptable salt and/or solvate thereof, for use in the prevention and/or the treatment of disorders associated to the inflammation induced by *P. acnes*, in particular in the prevention and/or the treatment of acne, psoriasis, chronic urticaria, urticaria pigmentosa, cutaneous autoinflammatory diseases, hidradenitis or atopic dermatis.

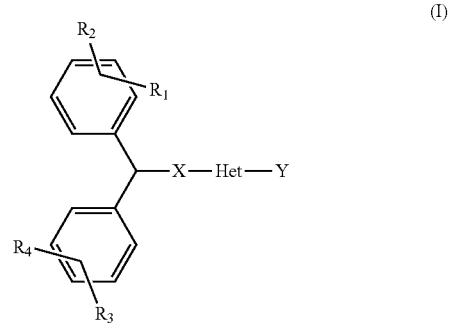

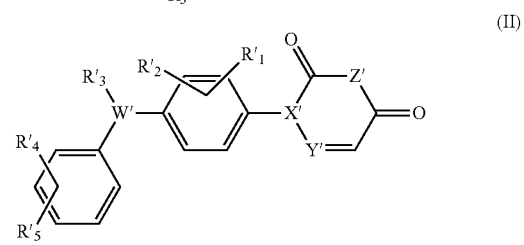

12 Claims, 23 Drawing Sheets
Specification includes a Sequence Listing.

(51) Int. Cl.
*A61P 17/06* (2006.01)
*A61K 31/495* (2006.01)
*A61K 45/06* (2006.01)
*A61K 31/202* (2006.01)
*A61K 31/203* (2006.01)

(52) U.S. Cl.
CPC ............ *A61P 17/10* (2018.01); *A61K 31/202* (2013.01); *A61K 31/203* (2013.01)

(58) Field of Classification Search
CPC . A61K 31/4965; A61K 2300/00; A61P 17/10; A61P 17/06; A61P 17/00; A61P 31/04; C07D 253/075; C07D 295/06
See application file for complete search history.

(56) References Cited

U.S. PATENT DOCUMENTS

2010/0221245 A1  9/2010  Kunin
2010/0278784 A1  11/2010  Pojasek et al.

FOREIGN PATENT DOCUMENTS

| | | | |
|---|---|---|---|
| JP | 2017128541 A | 7/2017 | |
| WO | WO 2004/062673 | 7/2004 | |
| WO | WO 2010135340 A2 | 11/2010 | |
| WO | WO-2017034984 A1 * | 3/2017 | ........... A61K 31/485 |

OTHER PUBLICATIONS

Sharma et al., *H1-antihistamines for chronic spontaneous urticaria (Review)*, 11 Cochrane Database of Systematic Reviews Art. No. CD006137 (2014).
Simons et al., *Histaime and $H_1$-antihistamines: Celebrating a century of progress*, 128(5) J Allergy Clin Immunol 1134-1150.e4 (Dec. 2011).
Achermann et al., *Propionibacterium acnes from Commensal to Opportunistic Biofilm-Associated Implant Pathogen*, 27(3) Clinical Microbiology Reviews 419-440 (Jul. 2014).
Alencar et al., *Pro- and anti-inflammatory activities of the latex from Calotropis procera (Ait.) R.Br. are triggered by compounds fractionated by dialysis*, 55 Inflamm Res. 559-564 (2006).
Baran, *Peroxisome Proliferator-Activated Receptors (PPARs)*, 3 Encyclopedia of Toxicology 812-814 (2014).
Bojar et al., *Acne and Propionibacterium Acnes*, 22 Clinics in Dermatology 375-379 (2004).
Brook et al., *Infections Caused by Propionibacterium Species*, 13 Reviews of Infectious Diseases 819-822 (1991).
Brzuszkiewicz et al., *Comparative Genomics and Transcriptomics of Propionibacterium acnes*, 6(6) PLoS One 1-13 (Jun. 2011).
Brüggemann et al., *The Complete Genome Sequence of Propionibacterium Acnes, a Commensal of Human Skin*, 305 Science 671-673 (Jul. 30, 2004).
Canonica et al., *Antihistaminic, Anti-Inflammatory, and Antiallergic Properties of the Nonsedating Second-Generation Antihistamine Desloratadine: A Review of the Evidence*, 4 WAO Journal 47-53 (Feb. 2011).
Dessinioti et al., *The role of Propionibacterium acnes in acne pathogenesis: facts and controversies*, 28 Clinics in Dermatology 2-7 (2010).
Eishi et al., *Quantitative Analysis of Mycobacterial and Propionibacterium DNA in Lymph Nodes of Japanese and European Patients with Sarcoidosis*, 40(1) Journal of Clinical Microbiology 198-204 (Jan. 2002).
Fehri et al., *Prevalence of Propionibacterium acnes in diseased prostates and its inflammatory and transforming activity on prostate epithelial cells*, 301 International Journal of Medical Microbiology 69-78 (2011).

Fukuoka et al., *Structure-based discovery of anti-influenza virus A compounds among medicines*, 1820 Biochimica et Biophysica Acta 90-95 (2012).
Fung et al., *Treatment Regimens for Patients with Toxoplasmic Encephalitis*, 18(6) Clinical Therapeutics 1037-1057 (1996).
Funke et al., *Clinical Microbiology of Coryneform Bacteria*, 10(1) Clinical Microbiology Reviews 125-159 (Jan. 1997).
Giustizieri et al., *H1 histamine receptor mediates inflammatory responses in human keratinocytes*, 114(5) J. Allergy Clin. Immunol. 1176-1182 (Nov. 2004).
Gohil et al., *Meclizine is neuroprotective in models of Huntington's disease*, 20(2) Human Molecular Genetics 294-300 (2011).
Graham et al., *Cutaneous Biology Proinflammatory cytokine production by human keratinocytes stimulated with Propionibacterium acnes and P. acnes GroEL*, 150 British Journal of Dermatology 421-428 (2004).
Grange et al., *Nicotinamide inhibits Propionibacterium acnes-induced IL-8 production in keratinocytes through the NF-κB and MAPK pathways*, 56 Journal of Dermatological Science 106-112 (2009).
Grange et al., *Production of Superoxide Anions by Keratinocytes Initiates P. acnes-Induced Inflammation of the Skin*, 5(7) PLoS One 1-14 (Jul. 2009).
Gupta et al., *Peroxisome proliferator-activated receptors (PPARs) and PPAR agonists: the 'future' in dermatology therapeutics?*, 307 Arch. Dermatol. Res. 767-780 (2015).
Herman et al., *Antihistamines in the treatment of dermatitis*, 7(6) J Cutan Med Surg 467-473 (Nov.-Dec. 2003) (abstract only).
Jappe et al., *Cutaneous Biology Propionibacterium acnes and inflammation in acne: P. acnes has T-cell mitogenic activity*, 146 British Journal of Dermatology 202-209 (2002).
Jenkins, *A Clinical Study of Chlorcyclizine Hydrochloride, 'Perazil'; A New Antihistaminic Drug*, 42(5) Journal of the National Medical Association 293-298 (Sep. 1950).
Johnson et al., *Cell Wall Compositions and Deoxyribonucleic Acid Similarities Among the Anaerobic Coryneforms, Classical Propionibacteria, and Strains of Arachnia propionica*, 109(3) Journal of Bacteriology 1047-1066 (Mar. 1972).
Jugeau et al., *Induction of toll-like receptors by Propionibacterium acnes*, 153 British Journal of Dermatology 1105-1113 (2005).
Kamisango et al., *Structures and Biological Activities of Peptidoglycans of Listeria monocytogenes and Propionibacterium acnes*, 92 J. Biochem 23-33 (1982).
Kang et al., *Inflammation and Extracellular Matrix Degradation Mediated by Activated Transcription Factors Nuclear Factor-κB and Activator Protein-1 in Inflammatory Acne Lesions* in Vivo, 166(6) American Journal of Pathology 1691-1699 (Jun. 2005).
Kayembe et al., *Diclazuril for Isopora Belli Infection in AIDS*, The Lancet 1397-1398 (Jun. 17, 1989).
Kimura et al., *Mast cells and histamine play an important role in edema and leukocyte recruitment induced by Potamotrygon motoro stingray venom in mice*, 103 Toxicon 65-73 (2015).
Kistowska et al., *IL-1β Drives Inflammatory Responses to Propionibacterium acnes In Vitro and In Vivo*, 134 Journal of Investigative Dermatology 677-685 (2014).
Kochevar et al., *Effects of Systemic Indomethacin Meclizine, and BW755C on Chronic Ultraviolet B-Induced Effects in Hairless Mouse Skin*, 100(2) The Journal of Investigative Dermatology 186-202 (1993).
Lin et al., *Topical Antihistamines Display Potent Anti-Inflammatory Activity Linked in Part to Enhanced Permeability Barrier Function*, 133(2) J. Invest Dermatol. 469-478 (Feb. 2013).
Limson-Pobre et al., *Use of Diclazuril for the Treatement of Isosporiasis in Patients with AIDS*, 20 Clinical Infectious Diseases 201-202 (1995).
Martins et al., *Plasmodium berghei-infected mice: lack of effect of meclizine and cimetidine on the development of pulmonary oedema*, 80(5) Ann Trop Med Parasitol 491-499 (Oct. 1986).
Maruyama, *Early changes in the radiosensitivity of Corynebactium parvum-stimulated CFU-S*, 1(2) Stem Cells 81-96 (1981).
Matsushita et al., *Meclozine Facilitates Proliferation and Differentiation of Chondrocytes by Attenuating Abnormally Activated FGFR3 Signaling in Achondroplasia*, 8(12) PLoS One 1-9 (Dec. 2013).

(56) References Cited

OTHER PUBLICATIONS

McDowell et al., *An Expanded Multilocus Sequence Typing Scheme for* Propionibacterium acnes: *Investigation of 'Pathogenic', 'Commensal' and Antibiotic Resistant Strains*, 7(7) PLoS One 1-14 (Jul. 2012).

McDowell et al., *The Opportunistic Pathogen* Propionibacterium acnes: *Insights into Typing, Human Disease, Clonal Diversification and CAMP Factor Evolution*, 8(9) PLos One 1-22 (Sep. 2013).

Nagy et al., *Distinct Strains of* Propionibacterium acnes *Induce Selective Human β-Defensin-2 and Interleukin-8 Expression in Human Keratinocytes Through Toll-Like Receptors*, 124 J. Inves. Dermatol. 931-938 (2005).

Noel et al., *Pacemaker endocarditis caused by Propionibacterium acnes: A case report*, 41(6) Heart and Lung e21-e23 (Jul. 7, 2015).

Qin et al., Propionibacterium acnes *Induces IL-1β Secretion via the NLRP3 Inflammasome in Human Monocytes*, 134 Journal of Investigative Dermatology 381-388 (2014).

Rabeony et al., *Inhibition of Keratinocyte Differentiation by the Synergistic Effect of IL-17A, IL-22, IL 1α, TNFα and Oncostatin M*, 9(7) PLoS One 1-8 (Jul. 2014).

Shen et al., *Proteomic analysis of the effect of diclazuril on second-generation merozoites of* Eimeria tenella, 113 Parasitol Res. 903-909 (2013).

Trivedi et al., *Gene Array Expression Profiling in Acne Lesions Reveals Marked Upregulation of Genes Involved Inflammation and Matrix Remodeling*, 126 The Society for Investigative Dermatology 1071-1079 (2006).

Tsai et al., Propionibacterium acnes-*induced iNOS and COX-2 protein expression via ROS-dependent NF-κB and AP-1 activation in macrophages*, 69 Journal of Dermatological Science 122-131 (2013).

Tunney et al., *Detection of Prosthetic Hip Infection and Revisions Arthroplasty by Immunofluorescence and PCR Amplification of the Bacterial 16S rRNA Gene*, 37(10) Journal of Clinical Microbiology 3281-3290 (Oct. 1999).

Zedtwitz-Liebenstein et al., *Pacemaker Endocarditis Due to* Propionibacterium acnes, 31(3) Infection 184-185 (2003).

Zhou et al., *A novel serine/threonine protein phosphatase type 5 from second-generation merozoite of* Eimeria tenella *is associated with diclazuril-induced apoptosis*, 112 Parasitol Res. 1771-1780 (2013).

Zhou et al., *Receptor for activated C kinase ortholog of second-generation merozoite in* Eimeria tenella: *clone, characterization, and diclazuril-induced mRNA expression*, 111 Parasitol Res. 1447-1455 (2012).

Dr. Alien J. Dourna, Chicago Tribune, 2 pages, retrieved from the Internet on Jun. 13, 2021 (Jan. 25, 2000).

* cited by examiner

MECLOZINE DERIVATIVES AND DICLAZURIL DERIVATIVES FOR USE IN THE PREVENTION AND/OR THE TREATMENT OF DISORDERS ASSOCIATED TO THE INFLAMMATION INDUCED BY P. ACNES

CROSS-REFERENCE TO RELATED APPLICATIONS

This application is a U.S. National Stage patent application pursuant to 35 U.S.C. § 371 of International Patent Application PCT/EP2017/067774, filed on Jul. 13, 2017, and published as WO 2018/011375 on Jan. 18, 2018, which claims priority to European Patent Application 16305912.4 filed on Jul. 13, 2016, all of which are incorporated herein by reference in their entireties for all purposes.

TECHNICAL FIELD

The present invention relates to two families of compounds, Meclozine derivatives and Diclazuril derivatives for use in the prevention and/or the treatment of disorders associated to the inflammation induced by P. acnes, in particular in the prevention and/or the treatment of acne, psoriasis, chronic urticaria, urticaria pigmentosa, cutaneous autoinflammatory diseases, hidradenitis or atopic dermatis. The present invention also relates to a pharmaceutical composition comprising said compounds for use in the prevention and/or the treatment of disorders associated to the inflammation induced by P. acnes, in particular in the prevention and/or the treatment of acne, psoriasis, chronic urticaria, urticaria pigmentosa, cutaneous autoinflammatory diseases, hidradenitis or atopic dermatis.

BACKGROUND INFORMATION

*Propionibacterium* genus belongs to the phylum Actinobacteria and contains cutaneous species predominantly found on the surface of the skin. The most important cutaneous commensal species are P. acnes, P. granulosum, P. lymphophilum, P. propionicum and P. avidum.

*Propionibacterium acnes* (P. acnes), which was classified previously as *Corynebacterium parvum*, is a gram-positive, aerotolerant-anaerobic bacterium, asporulated and described as diphtheroid or coryneform. A number of unique features of the P. acnes cell wall and outer envelope further distinguishes it from other gram-positive bacteria. P. acnes synthesizes phosphatidylinositol which is usually a characteristic of eukaryotic cells. Also, the peptidoglycan of P. acnes is distinct from most gram-positive bacteria, containing a cross-linkage region of peptide chains with L,L-diaminopimelic acid and D-alanine in which two glycine residues combine with amino and carboxyl groups of two L,L-diaminopimelic acid residues (Kamisango 1982).

P. acnes belong to the normal skin microbiota and is especially found at the sebaceous follicles and areas where sebum production is important (face, chest, back). The bacterial density varies among individuals and explored areas but can reach up to $10^7$ bacteria per $cm^2$ of skin. P. acnes is adapted to this ecological niche in its ability to catabolize fatty acids of the sebum that provide the energy needed for growth (Bojar and Holland 2004). The abundant presence of P. acnes in human commensal flora suggests a reflection of a long coevolution in which the host and the bacteria derive each their advantage. However, if P. acnes strains were considered as a commensal, several studies bring insights to switch the bacteria to opportunistic pathogen as it appears to be present in the oral cavity, the respiratory tract, ocular mucosa and gastrointestinal tract. It also seems to be involved in more invasive infections and clinical conditions (See Review Achermann et al., 2014). Indeed, P. acnes is commonly isolated in the inflammatory acne on skin (Dessinioti 2010) but has also been found in late-stage prosthetic joint infections, endocarditis, endophthalmitis, osteomyelitis, shunt-associated central nervous system infections (Brook and Frazier 1991; Funke 1997; Tunney 1999). More surprisingly, a role in the aetiology of sarcoidosis (Eishi 2002), as well as in prostate cancer is suspected (Fehri 2011). It was also frequently isolated from specimen coming from medical implant biofilm infection (Zedtwitz-Liebenstein 2003).

The genome of P. acnes has been completely sequenced with a size of 2.5 Mbp. It has genes encoding metabolic enzymes enabling it to survive in microaerophilic conditions, but also lipases which degrade the lipids contained in the pilosebaceous follicle providing the necessary energy to the bacteria. Also, P. acnes has genes encoding surface proteins containing the anchor sequence LPXTG, potentially involved in the activation of innate immunity as well as in adhesion (Brüggemann 2004; Brzuszkiewicz 2011). First, P. acnes strains were divided in serotypes I and II corresponding to the presence of galactosyl residues at the surface of the bacteria (Johnson and Cummins 1972). Based on nucleotide sequencing and MLST analysis, six P. acnes phylotypes ($IA_1$, $IA_2$, IB, IC, II, and III) have been identified (McDowell 2013) and are related to their ability to induce the production of pro-inflammatory molecules, their association with infections, their biochemical and morphological characteristics as well as their ability to aggregate (McDowell 2012).

The pathogenicity of P. acnes is characterized by its ability to secrete many components in the environment which are able to interact with the immune system. Colonization of the pilosebaceous gland by P. acnes is the first event which can result in an inflammatory response, wherein the bacterium 1) secret lytic enzymes and lipases contributing to attack the follicular epithelium; 2) produces chemotactic factors that will attract neutrophils across the epithelial membrane (Jappe 2002); and 3) activate the TLRs receptors of innate immunity. Indeed, P. acnes is able to induce in vitro production of proinflammatory molecules (interleukins IL-1α/β, IL-8, IL-12, TNF-α, β-defensins) by the keratinocytes, sebocytes and monocytes but also in vivo in the acne lesions. This production is thereby via the TLR-2 receptor and the activation of the NF-κB and MAPK signaling pathways as well as via the NLRP3 inflammasome pathway. P. acnes also induces a massive production of reactive oxygen species (ROS) by keratinocytes contributing to the initiation and the amplification of the inflammatory reaction (Graham 2004; Grange 2009a; Grange 2009b; Kang 2005; Nagy 2005; Trivedi 2006; Qin 2014; Kistowska 2014, Jugeau 2005).

From 25-30 years, the treatment of acne was to act either on the amount of sebum secreted and/or on either the reduction of bacterial density in the pilosebaceous gland. Acne responds very slowly to antibiotic treatments that should last several months. Moreover, the widespread use of antibiotics in the treatment of acne has caused considerable selection pressure, leading to the onset of P. acnes resistance to macrolide antibiotics and tetracyclines, with now 40% of resistant strains. Bacterial resistance, particularly of P. acnes to antibiotics has become a major global problem and several lines of research are directed to the development of new therapeutic approaches.

Therefore, to date, a need exists for preventing and/or a treating disorders associated to associated to the inflammation induced by *P. acnes*.

In this study, we phenotypically screened chemical library in order to identified new molecules able to decrease the inflammation induced by *P. acnes*.

BRIEF SUMMARY OF THE INVENTION

The inventors of the present invention have thus discovered two families of compounds, Meclozine derivatives and Diclazuril derivatives in the prevention and/or the treatment of disorders associated to the inflammation induced by *P. acnes*, in particular in the prevention and/or the treatment of acne, psoriasis, chronic urticaria, urticaria pigmentosa, cutaneous autoinflammatory diseases, hidradenitis or atopic dermatis.

Thus, a first object of the invention is a compound of the following general formula (I):

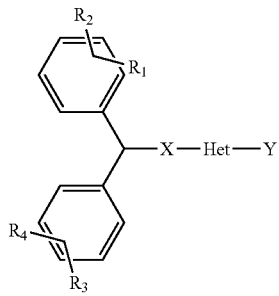

or a pharmaceutically acceptable salt and/or solvate thereof, wherein:
  Het is a nitrogen-containing heterocycloalkyl;
  X is a single bond, a ($C_1$-$C_6$)alkyl group or a ($C_1$-$C_6$) alkoxy group, in particular a single bond, a ($C_1$-$C_3$) alkyl group or a ($C_1$-$C_3$)alkoxy group;
  Y is a group selected from —$R_{10}$C(O)NH$R_{11}$; —$R_{10}$C (O)N$R_{11}$; ($C_1$-$C_6$)alkyl; or ($C_1$-$C_6$)alkyl-aryl with ($C_1$-$C_6$)alkyl optionally substituted with =O, =S or a phenyl and with aryl optionally substituted with one or several substituents selected from hydrogen atom, halo, —CN, —$NO_2$, —O$R_{12}$, —N$R_{13}R_{14}$, —C(O)O$R_{15}$, —C(O)N$R_{16}R_{17}$, —S(O)$_2$N$R_{18}R_{19}$, —S(O)$_2$$R_{20}$, —NHS(O)$_2$$R_{21}$, —NHC(O)$R_{22}$, or a group selected from ($C_1$-$C_6$)alkyl, aryl, ($C_1$-$C_6$)alkyl-aryl, heterocycle, ($C_1$-$C_6$)alkyl-heterocycle, said group being optionally substituted with one or several groups selected from halo, ($C_1$-$C_6$)alkyl, —O$R_{23}$ or —OC(O) $R_{24}$, or with two adjacent substituents which form together with the carbon atoms to which they are chemically linked an heterocycle;
  $R_1$ to $R_4$ are, independently of one another, hydrogen atom or a group selected from halo, —$NO_2$, —CN, —O$R_{25}$, —N$R_{26}R_{27}$, —C(O)O$R_{28}$, —S(O)$_2$$R_{29}$, or a ($C_1$-$C_6$) alkyl group optionally substituted with one or several groups selected from halo or —O$R_{30}$;
  $R_{10}$ to $R_{30}$ are, independently of one another, hydrogen atom, halo, or a group selected from ($C_1$-$C_6$)alkyl, aryl, ($C_1$-$C_6$)alkyl-aryl, heterocycle, ($C_1$-$C_6$)alkyl-heterocycle, said group being optionally substituted with one or several groups selected from halo, ($C_1$-$C_6$)alkyl, $CF_3$ or —O$R_{31}$;
  $R_{31}$ is hydrogen atom, halo or a ($C_1$-$C_6$)alkyl group;
for use in the prevention and/or the treatment of disorders associated to the inflammation induced by *P. acnes*, in particular in the prevention and/or the treatment of acne, psoriasis, chronic urticaria, urticaria pigmentosa, cutaneous autoinflammatory diseases, hidradenitis or atopic dermatis.

A second object of the invention is a compound of the following general formula (II):

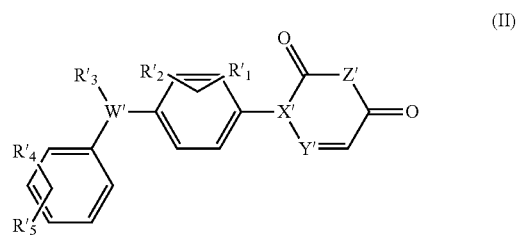

or a pharmaceutically acceptable salt and/or solvate thereof, wherein:
  X', Y' and Z' are, independently of one another, CH, $CH_2$, NH or N;
  W' is CH or SH;
  $R'_1$ and $R'_2$ are, independently of one another, hydrogen atom, halo, —CN, —$NO_2$, —$CF_3$, —$OR'_7$, —$NR'_8R'_9$, or a ($C_1$-$C_6$)alkyl group;
  $R'_3$ is H, —CN, =O, $OR'_{10}$, or a ($C_1$-$C_6$)alkyl group;
  $R'_4$ and $R'_5$, are, independently of one another, hydrogen atom or a group selected from halo, —$NO_2$, —CN, —$OR'_{11}$, —$NR'_{12}R'_{13}$, —C(O)$OR'_{14}$, —S(O)$_2$$R'_{15}$, or a ($C_1$-$C_6$)alkyl group optionally substituted with one or several groups selected from halo or —$OR'_{16}$;
  $R'_7$ to $R'_{16}$ are, independently of one another, hydrogen atom or a group selected from ($C_1$-$C_6$)alkyl, aryl, ($C_1$-$C_6$)alkyl-aryl, heterocycle, ($C_1$-$C_6$)alkyl-heterocycle, said group being optionally substituted with one or several groups selected from halo, ($C_1$-$C_6$)alkyl, $CF_3$ or —$OR'_{17}$;
  $R'_{17}$ is hydrogen atom, halo or a ($C_1$-$C_6$)alkyl group;
for use in the prevention and/or the treatment of disorders associated to the inflammation induced by *P. acnes*, in particular in the prevention and/or the treatment of acne, psoriasis, chronic urticaria, urticaria pigmentosa, cutaneous autoinflammatory diseases, hidradenitis or atopic dermatis.

A third object of the present invention relates to a pharmaceutical composition comprising at least one compound of general formula (I) and/or one compound of general formula (II) and at least one pharmaceutically acceptable excipient, for use in the prevention and/or the treatment of disorders the inflammation induced by *P. acnes*, in particular in the prevention and/or the treatment of acne, psoriasis, chronic urticaria, urticaria pigmentosa, cutaneous autoinflammatory diseases, hidradenitis or atopic dermatis.

Definition

For the purpose of the invention, the term "pharmaceutically acceptable" is intended to mean what is useful to the preparation of a pharmaceutical composition, and what is generally safe and non-toxic, for a pharmaceutical use.

The term "pharmaceutically acceptable salt or solvate" is intended to mean, in the framework of the present invention, a salt or solvate of a compound which is pharmaceutically acceptable, as defined above, and which possesses the pharmacological activity of the corresponding compound.

The pharmaceutically acceptable salts comprise:

(1) acid addition salts formed with inorganic acids such as hydrochloric, hydrobromic, sulfuric, nitric and phosphoric acid and the like; or formed with organic acids such as acetic, benzenesulfonic, fumaric, glucoheptonic, gluconic, glutamic, glycolic, hydroxynaphtoic, 2-hydroxyethanesulfonic, lactic, maleic, malic, mandelic, methanesulfonic, muconic, 2-naphtalenesulfonic, propionic, succinic, dibenzoyl-L-tartaric, tartaric, p-toluenesulfonic, trimethylacetic, and trifluoroacetic acid and the like, and (2) base addition salts formed when an acid proton present in the compound is either replaced by a metal ion, such as an alkali metal ion, an alkaline-earth metal ion, or an aluminium ion; or coordinated with an organic or inorganic base. Acceptable organic bases comprise diethanolamine, ethanolamine, N-methylglucamine, triethanolamine, tromethamine and the like. Acceptable inorganic bases comprise aluminium hydroxide, calcium hydroxide, potassium hydroxide, sodium carbonate and sodium hydroxide.

Acceptable solvates for the therapeutic use of the compounds of the present invention include conventional solvates such as those formed during the last step of the preparation of the compounds of the invention due to the presence of solvents. As an example, mention may be made of solvates due to the presence of water (these solvates are also called hydrates) or ethanol.

The terms "$(C_1-C_6)$alkyl", as used in the present invention, refers to a straight or branched saturated hydrocarbon chain containing from 1 to 6 carbon atoms including, but not limited to, methyl, ethyl, n-propyl, iso-propyl, n-butyl, iso-butyl, sec-butyl, t-butyl, n-pentyl, iso-pentyl, sec-pentyl, tert-pentyl, n-hexyl, iso-hexyl, sec-hexyl, tert-hexyl, and the like.

Similarly, the terms "$(C_1-C_3)$alkyl", as used in the present invention, refers to a straight or branched saturated hydrocarbon chain containing from 1 to 3 carbon atoms including, but not limited to, methyl, ethyl, n-propyl, iso-propyl, and the like.

The term "aryl", as used in the present invention, refers to an aromatic hydrocarbon group comprising preferably 6 to 10 carbon atoms and comprising one or more, notably 1 or 2, fused rings, such as, for example, a phenyl or naphtyl group. Advantageously, it will be a phenyl group.

The term "$(C_1-C_6)$alkyl-aryl", as used in the present invention, refers to an aryl group as defined above bound to the molecule via a $(C_1-C_6)$alkyl group as defined above. In particular, the $(C_1-C_6)$alkyl-aryl group is a benzyl or a propylbenzyl group.

The term "$(C_1-C_6)$alkoxy", as used in the present invention, refers to a $(C_1-C_6)$alkyl group as defined above bound to the molecule via an oxygen atom, including, but not limited to, methoxy, ethoxy, n-propoxy, iso-propoxy, n-butoxy, iso-butoxy, sec-butoxy, t-butoxy, n-pentoxy, n-hexoxy, and the like. Similarly, the term "$(C_1-C_3)$alkoxy", as used in the present invention, refers to a $(C_1-C_3)$alkyl group as defined above bound to the molecule via an oxygen atom, including, but not limited to, methoxy, ethoxy, n-propoxy, iso-propoxy, and the like. In particular, the $(C_1-C_6)$ alkoxy group is a methoxy group or ethoxy group.

The term "$(C_3-C_6)$cycloalkyl", as used in the present invention, refers to a hydrocarbon ring having 3 to 6 carbon atoms, notably cyclopropyl, cyclopentyl, and cyclohexyl. Preferably, the $(C_3-C_6)$cycloalkyl group is a cyclopropyl group.

The term "heterocycle" as used in the present invention refers to a saturated, unsaturated or aromatic hydrocarbon monocycle or polycycle (comprising fused, bridged or spiro rings), such as a bicycle, in which one or more, advantageously 1 to 4, and more advantageously 1 or 2, carbon atoms have each been replaced with a heteroatom selected from nitrogen, oxygen and sulphur atoms, and notably being a nitrogen atom. Advantageously, the heterocycle comprises 5 to 15, notably 5 to 10 atoms in the ring(s). Each ring of the heterocycle has advantageously 5 or 6 members.

According to a particular embodiment, the heterocycle is a saturated, unsaturated or aromatic hydrocarbon monocycle or bicycle (comprising fused, bridged or spiro rings, notably fused rings), each cycle having 5 or 6 members and 1 to 4, notably 1 or 2, carbon atoms having each been replaced with a nitrogen or oxygen atom, notably a nitrogen atom.

A heterocycle can be notably thiophene, furan, pyrrole, imidazole, pyrazole, oxazole, isoxazole, thiazole, isothiazole, isothiazolidine, triazoles (1,2,3-triazole and 1,2,4-triazole), benzofuran, indole, benzothiophene, benzimidazole, indazole, benzoxazole, benzisoxazole, benzothiazole, benzisothiazole, pyridine, pyrimidine, pyridazine, pyrazine, triazine, quinoline, isoquinoline, quinoxaline, quinazoline, piperidine, piperazine, triazinane, morpholine, pyrrolidine, dihydropyridines, dihydropyrimidines (notably 1,2-dihydropyrimidine), dihydropyridazines, dihydropyrazines, dihydrotriazines, tetrahydropyridines, tetrahydropyrimidines, tetrahydropyridazines, tetrahydropyrazines, tetrahydrotriazines, tetrahydrofuran, dioxane, dioxalane, etc. In particular, the heterocycle is piperidine or piperazine.

The term "nitrogen-containing heterocycle" as used in the present invention refers to a heterocycle as defined above containing at least one nitrogen atom.

Such a nitrogen-containing heterocycle is thus a saturated, unsaturated or aromatic hydrocarbon monocycle or polycycle (comprising fused, bridged or spiro rings), such as a bicycle, in which one or more, advantageously 1 to 4, and more advantageously 1 or 2, carbon atoms have each been replaced with a heteroatom selected from nitrogen, oxygen and sulphur atoms, at least one of the heteroatom(s) being a nitrogen atom, and notably all the heteroatoms are nitrogen. Advantageously, the heterocycle comprises 5 to 15, notably 5 to 10 atoms in the ring(s). Each ring of the heterocycle has advantageously 5 or 6 members.

A nitrogen-containing heterocycle can be notably pyrrole, imidazole, pyrazole, oxazole, isoxazole, thiazole, isothiazole, isothiazolidine, triazoles (1,2,3-triazole and 1,2,4-triazole), indole, benzimidazole, indazole, benzoxazole, benzisoxazole, benzothiazole, benzisothiazole, pyridine, pyrimidine, pyridazine, pyrazine, triazine, quinoline, isoquinoline, quinoxaline, quinazoline, piperidine, piperazine, triazinane, morpholine, pyrrolidine, dihydropyridines, dihydropyrimidines (notably 1,2-dihydropyrimidine), dihydropyridazines, dihydropyrazines, dihydrotriazines, tetrahydropyridines, tetrahydropyrimidines, tetrahydropyridazines, tetrahydropyrazines, tetrahydrotriazines, etc. In particular, the heterocycle is piperidine or piperazine.

The term "$(C_1-C_6)$alkyl-heterocycle", as used in the present invention, refers to an heterocycle group as defined above bound to the molecule via a $(C_1-C_6)$alkyl group as defined above. In particular, the $(C_1-C_6)$alkyl-heterocycle group is a methyl-heterocycle group.

The term "halogen" or "halo", as used in the present invention, refers to a fluorine, bromine, chlorine or iodine atom.

DETAILED DESCRIPTION OF THE INVENTION

Meclozine Derivatives

According to a particular embodiment of the first object of the present invention, in the compound of the general formula (I) or a pharmaceutically acceptable salt and/or solvate thereof for use in the prevention and/or the treatment of disorders associated to the inflammation induced by *P. acnes*, X is a single bond, a $(C_1-C_6)$alkyl group or a $(C_1-C_6)$alkoxy group, in particular a single bond, a $(C_1-C_3)$ alkyl group or a $(C_1-C_3)$alkoxy group. More particularly, X is a single bond or a $(C_1-C_3)$alkoxy group, notably a single bond or a propoxy preferably n-propoxy group. Advantageously, X is a single bond.

In a preferred embodiment, in the compound of general formula (I), Y is a group selected from $—R_{10}C(O)NHR_{11}$; $—R_{10}C(O)NR_{11}$; $(C_1-C_6)$alkyl; or $(C_1-C_6)$alkyl-aryl with $(C_1-C_6)$alkyl optionally substituted with $=O$, $=S$ or a phenyl and with aryl optionally substituted with one or several substituents selected from hydrogen atom, halo, $—CN$, $—NO_2$, $—OR_{12}$, $—NR_{13}R_{14}$, $—C(O)OR_{15}$, $—C(O)NR_{16}R_{17}$, $—S(O)_2NR_{18}R_{19}$, $—S(O)_2R_{20}$, $—NHS(O)_2R_{21}$, $—NHC(O)R_{22}$, or a group selected from $(C_1-C_6)$alkyl, aryl, $(C_1-C_6)$alkyl-aryl, heterocycle, $(C_1-C_6)$alkyl-heterocycle, said group being optionally substituted with one or several groups selected from halo, $(C_1-C_6)$alkyl, $—OR_{23}$ or $—OC(O)R_{24}$, or with two adjacent substituents which form together with the carbon atoms to which they are chemically linked an heterocycle.

In particular, Y is a group selected from $—R_{10}C(O)NHR_{11}$, $—R_{10}C(O)NR_{11}$ or $(C_1-C_6)$alkyl-aryl with $(C_1-C_6)$ alkyl optionally substituted with $=O$, $=S$ or a phenyl and with aryl optionally substituted with one or several substituents selected from hydrogen atom, halo, $—CN$, $—NO_2$, $—OR_{12}$, $—NR_{13}R_{14}$, $—C(O)OR_{15}$, $—C(O)NR_{16}R_{17}$, $—S(O)_2NR_{18}R_{19}$, $—S(O)_2R_{20}$, $—NHS(O)_2R_{21}$, $—NHC(O)R_{22}$, or a group selected from $(C_1-C_6)$alkyl, aryl, $(C_1-C_6)$ alkyl-aryl, heterocycle, $(C_1-C_6)$alkyl-heterocycle, said group being optionally substituted with one or several groups selected from halo, $(C_1-C_6)$alkyl, $—OR_{23}$ or $—OC(O)R_{24}$, or with two adjacent substituents which form together with the carbon atoms to which they are chemically linked an heterocycle.

More particularly, Y is a $(C_1-C_6)$alkyl-aryl with $(C_1-C_6)$ alkyl optionally substituted with $=O$, $=S$ or a phenyl and with aryl optionally substituted with one or several substituents selected from hydrogen atom, halo, $—CN$, $—NO_2$, $—OR_{12}$, $—NR_{13}R_{14}$, $—C(O)OR_{15}$, $—C(O)NR_{16}R_{17}$, $—S(O)_2NR_{18}R_{19}$, $—S(O)_2R_{20}$, $—NHS(O)_2R_{21}$, $—NHC(O)R_{22}$, or a group selected from $(C_1-C_6)$alkyl, aryl, $(C_1-C_6)$ alkyl-aryl, heterocycle, $(C_1-C_6)$alkyl-heterocycle, said group being optionally substituted with one or several groups selected from halo, $(C_1-C_6)$alkyl, $—OR_{23}$ or $—OC(O)R_{24}$, or with two adjacent substituents which form together with the carbon atoms to which they are chemically linked an heterocycle.

Advantageously, Y is a $(C_1-C_6)$alkyl-aryl with aryl optionally substituted with one or several substituents, preferably one to four substituents, notably one or two substituents, selected from hydrogen atom, halo, $—CN$, $—NO_2$, $—OR_{12}$, $—NR_{13}R_{14}$, $—C(O)OR_{15}$, $—C(O)NR_{16}R_{17}$, $—S(O)_2NR_{18}R_{19}$, $—S(O)_2R_{20}$, $—NHS(O)_2R_{21}$, $—NHC(O)$ $R_{22}$, or a group selected from $(C_1-C_6)$alkyl, aryl, $(C_1-C_6)$ alkyl-aryl, heterocycle, $(C_1-C_6)$alkyl-heterocycle, said group being optionally substituted with one or several groups selected from halo, $(C_1-C_6)$alkyl, $—OR_{23}$ or $—OC(O)R_{24}$, or with two adjacent substituents which form together with the carbon atoms to which they are chemically linked an heterocycle.

More advantageously, Y is a $(C_1-C_6)$alkyl-aryl with aryl optionally substituted with one or several substituents, preferably one to four substituents, notably one or two substituents, selected from hydrogen atom, halo, $—CN$, $—NO_2$, $—OR_{12}$, $—NR_{13}R_{14}$, $—C(O)NR_{16}R_{17}$, $—S(O)_2NR_{18}R_{19}$, or a group selected from $(C_1-C_6)$alkyl, aryl, $(C_1-C_6)$alkyl-aryl, heterocycle or $(C_1-C_6)$alkyl-heterocycle; preferably said substituents are, independently of one another, hydrogen atom, halo, $—CN$, $—NO_2$, $—OR_{12}$, $—NR_{13}R_{14}$, $—C(O)NR_{16}R_{17}$, $—S(O)_2NR_{18}R_{19}$, or a group selected from $(C_1-C_6)$alkyl, heterocycle or $(C_1-C_6)$alkyl-heterocycle; more particularly said substituents are, independently of one another, hydrogen atom, halo, $—OR_{12}$, $—NR_{13}R_{14}$ or a $(C_1-C_6)$alkyl group. Advantageously said substituents are, independently of one another, hydrogen atom, halo, or a $(C_1-C_6)$alkyl notably $(C_1-C_3)$alkyl group.

In the above definitions of Y, the $(C_1-C_6)$alkyl-aryl is preferably a $(C_1-C_6)$alkyl-phenyl, more preferably a $(C_1-C_3)$ alkyl-phenyl.

In a particular embodiment of the first object of the present invention, X is a single bond, an $(C_1-C_3)$alkyl or $(C_1-C_3)$alkoxy group, notably a single bond, a propyl or a ethoxy preferably n-propyl or ethoxy group and Y is a $(C_1-C_6)$alkyl-aryl optionally substituted with one to four groups selected from $(C_1-C_6)$alkyl notably methyl and $(C_1-C_6)$alkoxy notably methoxy, preferably a $(C_1-C_6)$alkyl-phenyl optionally substituted with one to four groups selected from $(C_1-C_6)$alkyl notably methyl and $(C_1-C_6)$alkoxy notably methoxy. In this embodiment, X is preferably a $(C_1-C_3)$ alkoxy group notably an ethoxy and Y is preferably a $(C_1-C_6)$alkyl-phenyl.

According to another particular embodiment of the first object of the present invention, X is a single bond and Y is $(C_1-C_6)$alkyl-phenyl optionally substituted with one or several substituents, preferably one to four substituents, notably one or two substituents, selected from hydrogen atom, halo, $—CN$, $—NO_2$, $—OR_{12}$, $—NR_{13}R_{14}$, $—C(O)NR_{16}R_{17}$, $—S(O)_2NR_{18}R_{19}$, or a group selected from $(C_1-C_6)$alkyl, aryl, $(C_1-C_6)$alkyl-aryl, heterocycle or $(C_1-C_6)$alkyl-heterocycle; preferably said substituents are, independently of one another, hydrogen atom, halo, $—CN$, $—NO_2$, $—OR_{12}$, $—NR_{13}R_{14}$, $—C(O)NR_{16}R_{17}$, $—S(O)_2NR_{18}R_{19}$, or a group selected from $(C_1-C_6)$alkyl, heterocycle or $(C_1-C_6)$alkyl-heterocycle; more particularly said substituents are, independently of one another, hydrogen atom, halo, $—OR_{12}$, $—NR_{13}R_{14}$ or a $(C_1-C_6)$alkyl group. Advantageously said substituents are, independently of one another, hydrogen atom, halo, or a $(C_1-C_6)$alkyl notably $(C_1-C_3)$alkyl group.

In the compound of general formula (I), Het is a nitrogen-containing heterocycloalkyl or a moiety of formula (I'), in particular, Het is a nitrogen-containing heterocycloalkyl having five or six members including notably one or two nitrogen atoms, more particularly Het is a piperazinyl or a piperidinyl, preferably Het is a piperazinyl.

Advantageously, the compound of the first object of the invention is of the following general formula (Ia):

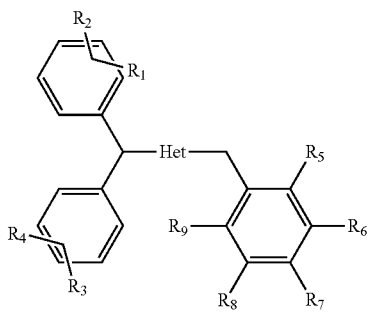

(Ia)

or a pharmaceutically acceptable salt and/or solvate thereof, wherein Het is a nitrogen-containing heterocycloalkyl, in particular having five or six members including notably one or two nitrogen atoms, more particularly Het is a piperazinyl or a piperidinyl, preferably Het is a piperazinyl.

Advantageously, the compound of the first object of the invention is of the following general formula (Ib):

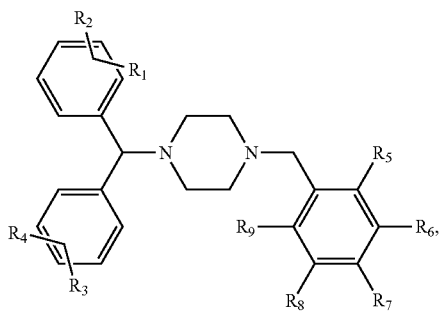

(Ib)

or a pharmaceutically acceptable salt and/or solvate thereof.

In the compound of general formula (I), (Ia) or (Ib), $R_1$ to $R_4$ are, independently of one another, hydrogen atom or a group selected from halo, $-NO_2$, $-CN$, $-OR_{25}$, $-NR_{26}R_{27}$, $-C(O)OR_{28}$, $-S(O)_2R_{29}$, or a $(C_1-C_6)$alkyl group optionally substituted with one or several groups selected from halo or $-OR_{30}$. In particular, $R_1$ to $R_4$ are, independently of one another, hydrogen atom or a group selected from halo, $-NO_2$, $-CN$, $-OR_{25}$, $-NR_{26}R_{27}$ or a $(C_1-C_6)$alkyl group, more particularly $R_1$ to $R_4$ are, independently of one another, hydrogen atom or a group selected from halo, $-OR_{25}$, $-NR_{26}R_{27}$ or a $(C_1-C_6)$alkyl group. Preferably, $R_1$ to $R_4$ are, independently of one another, hydrogen atom or halo, notably H, Cl or F.

In the compound of general formula (Ia) or (Ib), $R_5$ to $R_9$ are, independently of one another, hydrogen atom, halo, $-CN$, $-NO_2$, $-OR_{12}$, $-NR_{13}R_{14}$, $-C(O)OR_{15}$, $-C(O)NR_{16}R_{17}$, $-S(O)_2NR_{18}R_{19}$, $-S(O)_2R_{20}$, $-NHS(O)_2R_{21}$, $-NHC(O)R_{22}$, or a group selected from $(C_1-C_6)$alkyl, aryl, $(C_1-C_6)$alkyl-aryl, heterocycle, $(C_1-C_6)$alkyl-heterocycle, said group being optionally substituted with one or several groups selected from halo, $(C_1-C_6)$alkyl, $-OR_{23}$ or $-OC(O)R_{24}$; or the couple $R_5$-$R_6$, $R_6$-$R_7$, $R_8$-$R_8$ or $R_8$-$R_9$ form together with the carbon atoms to which they are chemically linked, an heterocycle, while the others are hydrogen atoms.

In a particular embodiment, the couple $R_5$-$R_6$, $R_6$-$R_7$, $R_8$-$R_8$ or $R_8$-$R_9$ form together with the carbon atoms to which they are chemically linked, an heterocycle, while the others are hydrogen atoms; said heterocycle preferably comprises 5 or 6 members, including notably one or two oxygen or nitrogen atom.

In another particular embodiment, $R_5$ to $R_9$ are, independently of one another, hydrogen atom, halo, $-CN$, $-NO_2$, $-OR_{12}$, $-NR_{13}R_{14}$, $-C(O)NR_{16}R_{17}$, $-S(O)_2NR_{18}R_{19}$, or a group selected from $(C_1-C_6)$alkyl, aryl, $(C_1-C_6)$alkyl-aryl, heterocycle or $(C_1-C_6)$alkyl-heterocycle; preferably $R_5$ to $R_9$ are, independently of one another, hydrogen atom, halo, $-CN$, $-NO_2$, $-OR_{12}$, $-NR_{13}R_{14}$, $-C(O)NR_{16}R_{17}$, $-S(O)_2NR_{18}R_{19}$, or a group selected from $(C_1-C_6)$alkyl, heterocycle or $(C_1-C_6)$alkyl-heterocycle; more particularly $R_5$ to $R_9$ are, independently of one another, hydrogen atom, halo, $-OR_{12}$, $-NR_{13}R_{14}$ or a $(C_1-C_6)$alkyl group. Advantageously $R_5$ to $R_9$ are, independently of one another, hydrogen atom, halo, or a $(C_1-C_6)$alkyl notably $(C_1-C_3)$alkyl group.

In a particular embodiment of the first object of the present invention:

X is a single bond, an $(C_1-C_3)$alkyl or $(C_1-C_3)$alkoxy group, notably a single bond, a propyl preferably n-propyl or an ethoxy group;

Y is a $(C_1-C_6)$alkyl-aryl preferably $(C_1-C_6)$alkyl-phenyl optionally substituted with one or several groups selected from $(C_1-C_6)$alkyl notably methyl or $(C_1-C_6)$ alkoxy notably methoxy; and $R_1$ to $R_4$ are, independently of one another, H or a group selected from halo, $-OR_{13}$, $-NR_{14}R_{15}$ or a $(C_1-C_6)$ alkyl group, preferably H or halo, notably H, Cl or F.

According to another particular embodiment of the first object of the present invention, in the formula (Ia) or (Ib):

$R_1$ to $R_4$ are, independently of one another, H or a group selected from halo, $-OR_{13}$, $-NR_{14}R_{15}$ or a $(C_1-C_6)$ alkyl group, preferably H or halo, notably H, Cl or F; and $R_5$ to $R_9$ are, independently of one another, H, halo, $-OR_{19}$, $-NR_{20}R_{21}$ or a $(C_1-C_6)$alkyl group, in particular H, halo, or a $(C_1-C_6)$alkyl notably $(C_1-C_3)$alkyl group.

In the above definition of Y and $R_1$ to $R_9$, $R_{10}$ to $R_{30}$ are, independently of one another, hydrogen atom, halo, or a group selected from $(C_1-C_6)$alkyl, aryl, $(C_1-C_6)$alkyl-aryl, heterocycle, $(C_1-C_6)$alkyl-heterocycle, said group being optionally substituted with one or several groups selected from halo, $(C_1-C_6)$alkyl, $CF_3$ or $-OR_{31}$, $R_{31}$ being hydrogen atom, halo or a $(C_1-C_6)$alkyl group; in particular, $R_{10}$ to $R_{30}$ are, independently of one another, hydrogen atom, halo, or a group selected from $(C_1-C_6)$alkyl.

In a particular embodiment of the first object of the invention, the compound of general formula (I), (Ia) or (Ib) is in the form of a salt, notably a salt of hydrochloric acid, in particular the dihydrochloride salt.

In a particular embodiment of the first object of the invention, the compound of general formula (I) can be a compound of the following formula (Ic), commonly named Meclozine:

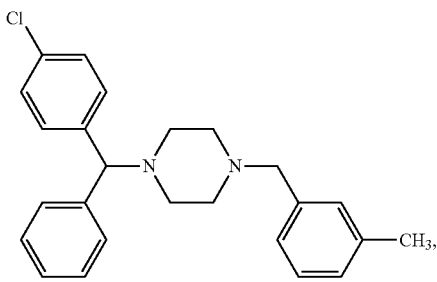

(Ic)

or a pharmaceutically acceptable salt and/or solvate thereof, preferably it is the dihydrochloride salt of compound (Ic), i.e. the compound commonly named Meclozine dihydrochloride.

The compound of general formula (I) can also be selected from Lidoflazine (formula Id), GBR12909 (formula Ie), Chlorcyclizine (formula If) and Lomerizine (formula Ig), or a pharmaceutically acceptable salt and/or solvate thereof such as an hydrochloride or dihydrochloride salt:

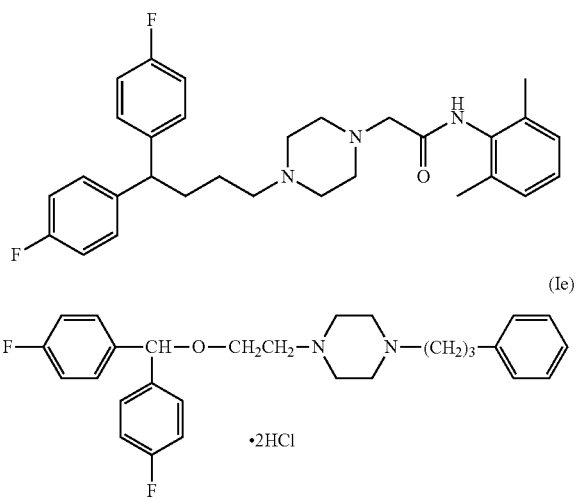

(Id)

(Ie)

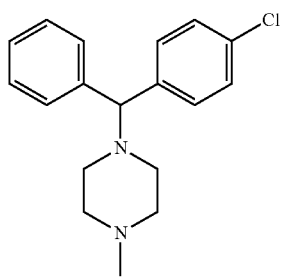

(If)

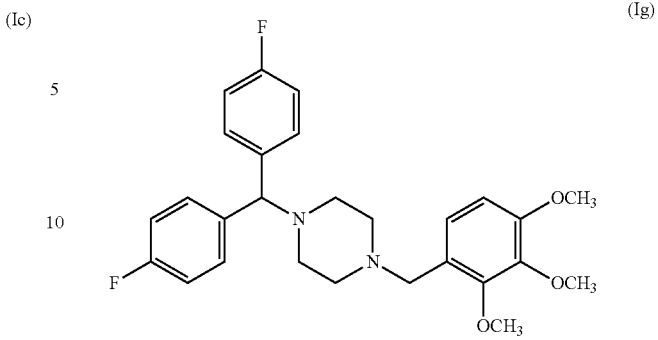

(Ig)

According to one particular embodiment, the present invention is directed to the compound of general formula (I) as defined above for use in the prevention and/or the treatment of disorders associated the inflammation induced by *P. acnes*.

The present invention also relates to a method for preventing and/or for treating disorders associated to the inflammation induced by *P. acnes*, comprising the administration to a person in need thereof of an effective dose of a compound of formula (I) as defined above.

The present invention also relates to the use of a compound of formula (I) as defined above, for the manufacture of a drug for the prevention and/or the treatment of disorders associated to the inflammation induced by *P. acnes*.

The disorders associated to the inflammation induced by *P. acnes* may be in particular acne, psoriasis, chronic urticaria, urticaria pigmentosa, cutaneous autoinflammatory diseases, hidradenitis or atopic dermatis.

Diclazuril Derivatives

The stereoisomers or mixtures of stereoisomers in any proportion, including the mixture of enantiomers, notably the racemate mixture, are also part of the second object of the present invention.

Within the meaning of this invention, "stereoisomers" is intended to designate diastereoisomers or enantiomers. These are therefore optical isomers. Stereoisomers which are not mirror images of one another are thus designated as "diastereoisomers," and stereoisomers which are non-superimposable mirror images are designated as "enantiomers". An equimolar mixture of two enantiomers is called a racemate mixture.

In particular, the second object of the invention is a compound of the following general formula (IIa):

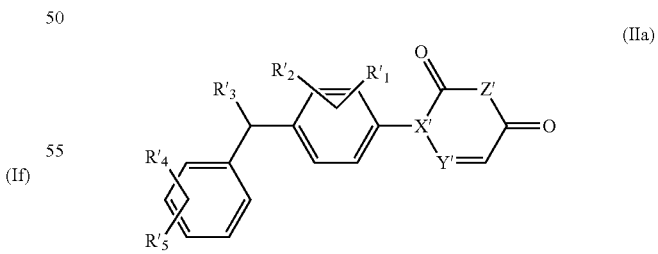

(IIa)

or a pharmaceutically acceptable salt and/or solvate thereof, wherein:

X', Y' and Z' are, independently of one another, CH, $CH_2$, NH or N;

$R'_1$ and $R'_2$ are, independently of one another, hydrogen atom, halo, —CN, —$NO_2$, —$CF_3$, —$OR'_7$, —$NR'_8R'_9$, or a ($C_1$-$C_6$)alkyl group;

$R'_3$ is H, —CN, =O, $OR'_{10}$, or a ($C_1$-$C_6$)alkyl group;

$R'_4$ and $R'_5$, are, independently of one another, hydrogen atom or a group selected from halo, —$NO_2$, —CN, —$OR'_{11}$, —$NR'_{12}R'_{13}$, —$C(O)OR'_{14}$, —$S(O)_2R'_{15}$, or a ($C_1$-$C_6$)alkyl group optionally substituted with one or several groups selected from halo or —$OR'_{16}$;

$R'_7$ to $R'_{16}$ are, independently of one another, hydrogen atom or a group selected from ($C_1$-$C_6$)alkyl, aryl, ($C_1$-$C_6$)alkyl-aryl, heterocycle, ($C_1$-$C_6$)alkyl-heterocycle, said group being optionally substituted with one or several groups selected from halo, ($C_1$-$C_6$)alkyl, $CF_3$ or —$OR'_{17}$;

$R'_{17}$ is hydrogen atom, halo or a ($C_1$-$C_6$)alkyl group;

for use in the prevention and/or the treatment of disorders associated to the inflammation induced by P. acnes, in particular in the prevention and/or the treatment of acne, psoriasis, chronic urticaria, urticaria pigmentosa, cutaneous autoinflammatory diseases, hidradenitis or atopic dermatis.

According to a particular embodiment of the second object of the present invention, in the compound of the general formula (II) or (IIa), or a pharmaceutically acceptable salt and/or solvate thereof, for use in the prevention and/or the treatment of disorders associated to the inflammation induced by P. acnes, at least two of X', Y' and Z' are N and the other is CH or $CH_2$, more particularly X', Y' and Z' are N.

In the compound of formula (II) or (IIa) of the invention, $R'_1$ and $R'_2$ are, independently of one another, hydrogen atom, halo, —CN, —$NO_2$, —$CF_3$, —$OR'_7$, —$NR'_8R'_9$, or a ($C_1$-$C_6$)alkyl group; in particular hydrogen atom, halo, —$CF_3$, —$OR'_7$, or a ($C_1$-$C_6$)alkyl group; more particularly hydrogen atom, halo, —$CF_3$, —OH, or a ($C_1$-$C_6$)alkyl group. Preferably $R'_1$ and $R'_2$ are, independently of one another, hydrogen atom or halo notably Cl.

In the compound of formula (II) or (IIa) of the invention, $R'_3$ is H, —CN, =O, $OR'_{10}$, or a ($C_1$-$C_6$)alkyl group; in particular —CN, =O, or $OR'_{10}$; more particularly —CN, =O, or OH. Preferably $R'_3$ is —CN.

In the compound of formula (II) or (IIa) of the invention, $R'_4$ and $R'_5$, are, independently of one another, hydrogen atom or a group selected from halo, —$NO_2$, —CN, —$OR'_{11}$, —$NR'_{12}R'_{13}$, —$C(O)OR'_{14}$, —$S(O)_2R'_{15}$, or a ($C_1$-$C_6$)alkyl group optionally substituted with one or several groups selected from halo or —$OR'_{16}$; in particular, $R'_5$ is an hydrogen atom and $R'_4$ is a hydrogen atom or a group selected from halo, —$NO_2$, —CN, —$OR'_{11}$, —$NR'_{12}R'_{13}$, —$C(O)OR'_{14}$, —$S(O)_2R'_{15}$, or a ($C_1$-$C_6$)alkyl group optionally substituted with one or several groups selected from halo or —$OR'_{16}$; more particularly, $R'_5$ is an hydrogen atom and $R'_4$ is selected from the group consisting of hydrogen atom, halo, —$OR'_{11}$, or a ($C_1$-$C_6$)alkyl group optionally substituted with one or several groups selected from halo or —$OR'_{16}$; even more particularly, $R'_5$ is an hydrogen atom and $R'_4$ is selected from the group consisting of hydrogen atom, halo, —$CF_3$, —OH, and a ($C_1$-$C_6$)alkyl group. Preferably $R'_5$ is an hydrogen atom and $R'_4$ is an hydrogen atom or halo; more preferably $R'_5$ is an hydrogen atom and $R'_4$ is an hydrogen atom or Cl.

In the above definitions of $R'_1$ to $R'_5$, $R'_7$ to $R'_{16}$ are, independently of one another, hydrogen atom, or a group selected from ($C_1$-$C_6$)alkyl, aryl, ($C_1$-$C_6$)alkyl-aryl, heterocycle, ($C_1$-$C_6$)alkyl-heterocycle, said group being optionally substituted with one or several groups selected from halo, ($C_1$-$C_6$)alkyl, $CF_3$ or —$OR'_{17}$, $R'_{17}$ being an hydrogen atom, halo or a ($C_1$-$C_6$)alkyl group.

In a particular embodiment of the second object of the invention, in the compound of general formula (II) or (IIa):

X', Y' and Z' are N; and $R'_1$ and $R'_2$ are, independently of one another, hydrogen atom, halo, —$CF_3$, —OH, or a ($C_1$-$C_6$)alkyl group, preferably hydrogen atom or halo notably Cl.

In a particular embodiment of the second object of the invention, in the compound of general formula (II) or (IIa):

X', Y' and Z' are N;

$R'_1$ and $R'_2$ are, independently of one another, hydrogen atom, halo, —$CF_3$, —OH, or a ($C_1$-$C_6$)alkyl group, preferably hydrogen atom or halo notably Cl; and $R'_3$ is H, —CN, =O, or $OR'_{10}$; preferably —CN, =O, or OH, more preferably —CN.

In a particular embodiment of the second object of the invention, in the compound of general formula (II) or (IIa):

X', Y' and Z' are N;

$R'_1$ and $R'_2$ are, independently of one another, hydrogen atom, halo, —$CF_3$, —OH, or a ($C_1$-$C_6$)alkyl group, preferably hydrogen atom or halo notably Cl;

$R'_3$ is H, —CN, =O, or $OR'_{10}$; preferably —CN, =O, or OH, more preferably —CN;

$R'_5$ is an hydrogen atom; and $R'_4$ is a hydrogen atom or a group selected from halo, —$NO_2$, —CN, —$OR'_{11}$, —$NR'_{12}R'_{13}$, —$C(O)OR'_{14}$, —$S(O)_2R'_{15}$, or a ($C_1$-$C_6$)alkyl group optionally substituted with one or several groups selected from halo or —$OR'_{16}$; in particular $R'_4$ is selected from the group consisting of hydrogen atom, halo, —$OR'_{11}$, or a ($C_1$-$C_6$)alkyl group optionally substituted with one or several groups selected from halo or —$OR'_{16}$.

In a particular embodiment of the second object of the invention, in the compound of general formula (II) or (IIa):

X', Y' and Z' are N;

$R'_1$ and $R'_2$ are, independently of one another, hydrogen atom, halo, —$CF_3$, —OH, or a ($C_1$-$C_6$)alkyl group, preferably hydrogen atom or halo notably Cl;

$R'_3$ is H, —CN, =O, or $OR'_{10}$; preferably —CN, =O, or OH, more preferably —CN;

$R'_5$ is an hydrogen atom; and $R'_4$ is selected from the group consisting of hydrogen atom, halo, —$CF_3$, —OH, and a ($C_1$-$C_6$)alkyl group; preferably hydrogen atom or halo notably Cl.

Advantageously, the compound of the first object of the invention is of the following general formula (IIb) or (IIc):

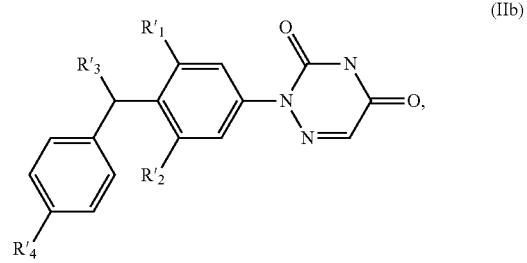

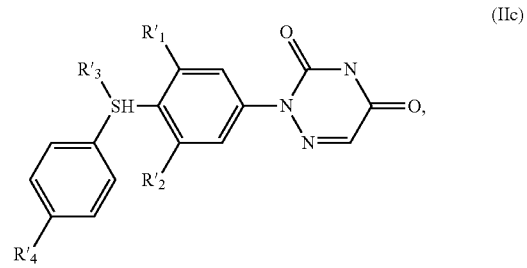

or a pharmaceutically acceptable salt and/or solvate thereof.

In a particular embodiment of the second object of the invention, the compound of general formula (II) can be a compound of the following formula (IId), commonly named Diclazuril:

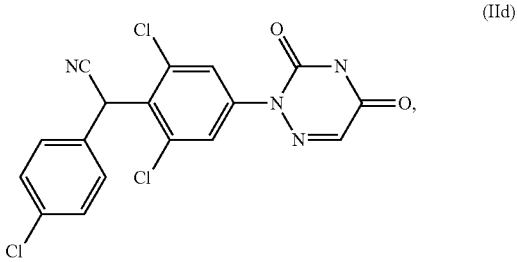

(IId)

or a pharmaceutically acceptable salt and/or solvate thereof.

The compound of general formula (II) can also be a compound of the following formula (IIe), commonly named PH000645-PH or a pharmaceutically acceptable salt and/or solvate thereof:

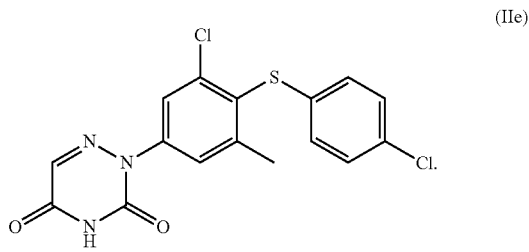

(IIe)

According to one particular embodiment, the present invention is directed to the compound of general formula (II) or (IIa) as defined above for use in the prevention and/or the treatment of disorders associated the inflammation induced by *P. acnes*.

The present invention also relates to a method for preventing and/or for treating disorders associated to the inflammation induced by *P. acnes*, comprising the administration to a person in need thereof of an effective dose of a compound of formula (II) or (IIa) as defined above.

The present invention also relates to the use of a compound of formula (II) or (IIa) as defined above, for the manufacture of a drug for the prevention and/or the treatment of disorders associated to the inflammation induced by *P. acnes*.

The disorders associated to the inflammation induced by *P. acnes* may be in particular acne, psoriasis, chronic urticaria, urticaria pigmentosa, cutaneous autoinflammatory diseases, hidradenitis or atopic dermatis.

Pharmaceutical Composition

The present invention also relates to a pharmaceutical composition comprising at least one compound of formula (I) or of formula (II) or (IIa) as defined above and at least one pharmaceutically acceptable excipient, for use in the prevention and/or the treatment of disorders associated to the inflammation induced by *P. acnes*.

The pharmaceutical compositions according to the invention may be formulated notably for topical administration, oral administration or for injection, wherein said compositions are intended for mammals, including humans. The pharmaceutical composition can be administered orally by means of tablets and gelatin capsules.

When a solid composition is prepared in the form of tablets, the main active ingredient is mixed with a pharmaceutical vehicle such as gelatin, starch, lactose, magnesium stearate, talc, gum arabic and the like. The tablets may be coated with sucrose or with other suitable materials, or they may be treated in such a way that they have a prolonged or delayed activity and they continuously release a predetermined amount of active principle.

A preparation in gelatin capsules is obtained by mixing the active ingredient with a diluent and pouring the mixture obtained into soft or hard gelatin capsules.

For administration by injection, aqueous suspensions, isotonic saline solutions or sterile and injectable solutions which contain pharmacologically compatible dispersing agents and/or wetting agents are used.

The pharmaceutical compositions according to the invention may also be administered topically by means of a cream, gel, stick or serum.

The active ingredient may be administered in unit dosage forms of administration, in mixture with standard pharmaceutical carriers, to animals or to humans.

The pharmaceutical compositions according to the invention may further comprise at least one other active ingredient, used for treating and/or preventing acne such as topical antibiotic (erythromycine, dalacine), topical anti-inflammatory (benzoyl peroxydes derivatives), topical anti-seborrheic (isotretinoin, tretinoin, adapalene), zinc derivatives (zinc gluconate), cyclins, or isotretinoin.

The present invention relates also to a pharmaceutical composition comprising:
(i) at least one compound of formula (I) or of formula (II) or (IIa) as defined above, and
(ii) at least one other active ingredient, such as one used for treating and/or preventing acne, such as topical antibiotic (erythromycine, dalacine), topical anti-inflammatory (benzoyl peroxydes derivatives), topical anti-seborrheic (isotretinoin, tretinoin, adapalene), zinc derivatives (zinc gluconate), cyclins, or isotretinoin,
as a combination product for simultaneous, separate or sequential use.

According to one particular embodiment, the present invention is directed to the pharmaceutical composition as defined above for use in the prevention and/or the treatment of disorders associated to the inflammation induced by *P. acnes*.

The present invention also relates to a method for preventing and/or treating disorders associated to the inflammation induced by *P. acnes*, comprising the administration to a person in need thereof of an effective dose of the pharmaceutical composition as defined above.

The present invention also relates to the use of the pharmaceutical composition as defined above, for the manufacture of a drug for the prevention and/or the treatment of disorders associated to the inflammation induced by *P. acnes*.

The disorders associated to the inflammation induced by *P. acnes* may be in particular acne, psoriasis, chronic urticaria, urticaria pigmentosa, cutaneous autoinflammatory diseases, hidradenitis or atopic dermatis.

The examples which follow illustrate the invention without limiting its scope in any way.

EXAMPLES

Example 1

Figure 1A:
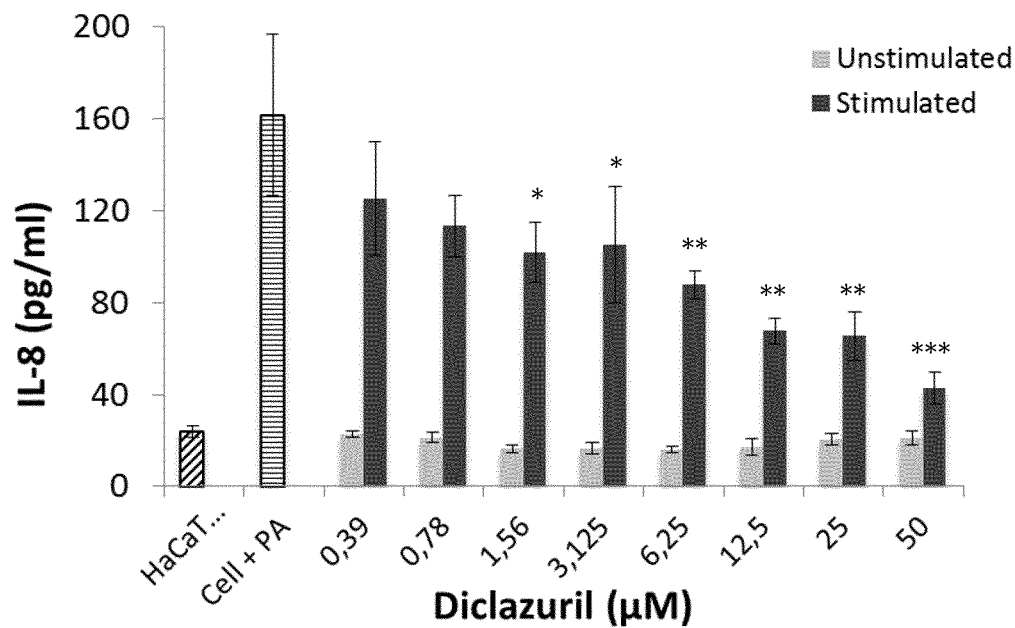
FIG. 1: Dose-dependent inhibition of IL-8 production and cell viability evaluation by keratinocytes pre-treated with Diclazuril and Meclozine. HaCaT cell were incubated for 24 h with (A, C) diclazuril and (B, D) meclozine alone at concentrations ranging from 0.39 to 50 μM (gray bar) and stimulated with *P. acnes* (dark bar). Controls experiments were done with HaCaT cell untreated and unstimulated (hatched bar) and with HaCaT cells stimulated with *P. acnes* only (horizontal line bar). Measurement of IL-8 production was realized by ELISA and cytotoxicity was determined by the MTT assay as described in Materials and Methods. Data are means±S.D. of three separate experiments. Statistical significance is indicated by * (P<0.05),  (P<0.01), * (P<0.001), and **** (P<0.0001), respectively.
Figure 1B:
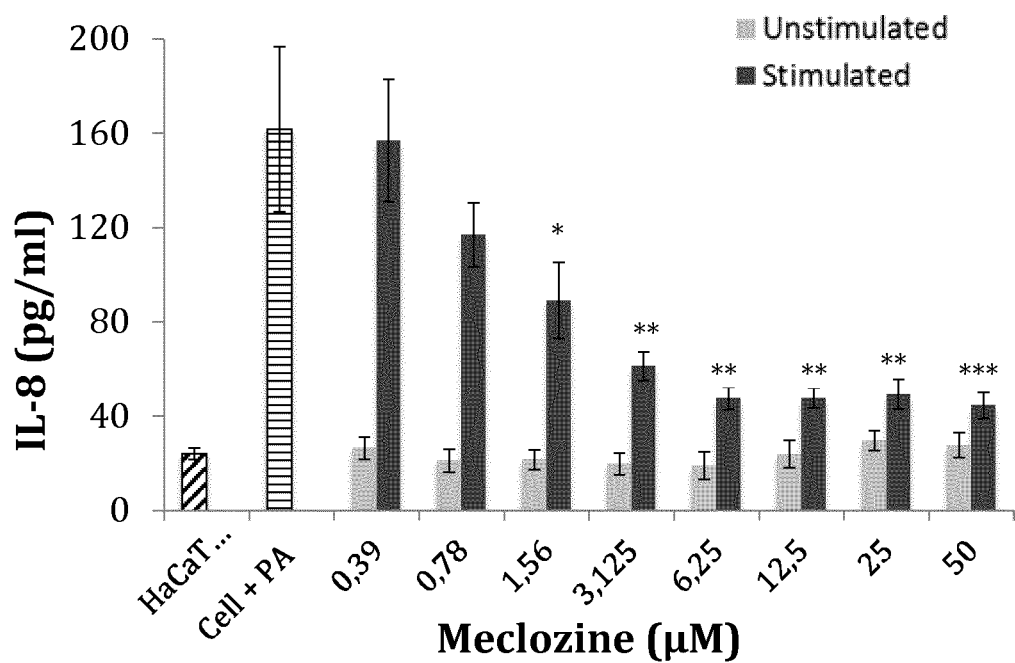
Figure 1C:
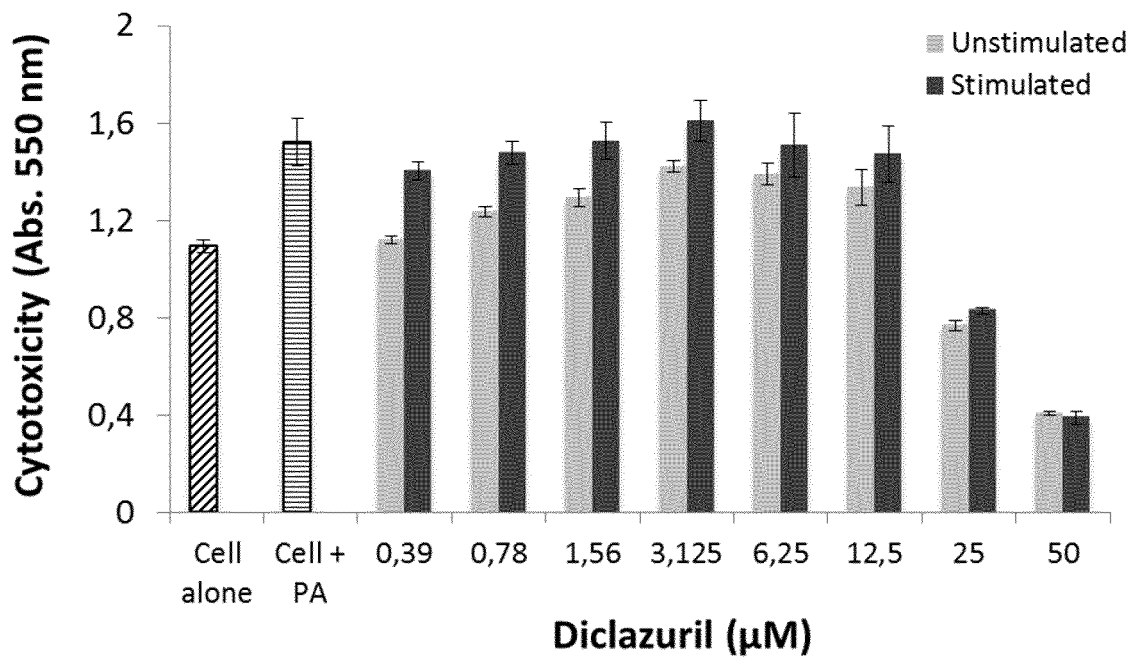
Figure 1D:
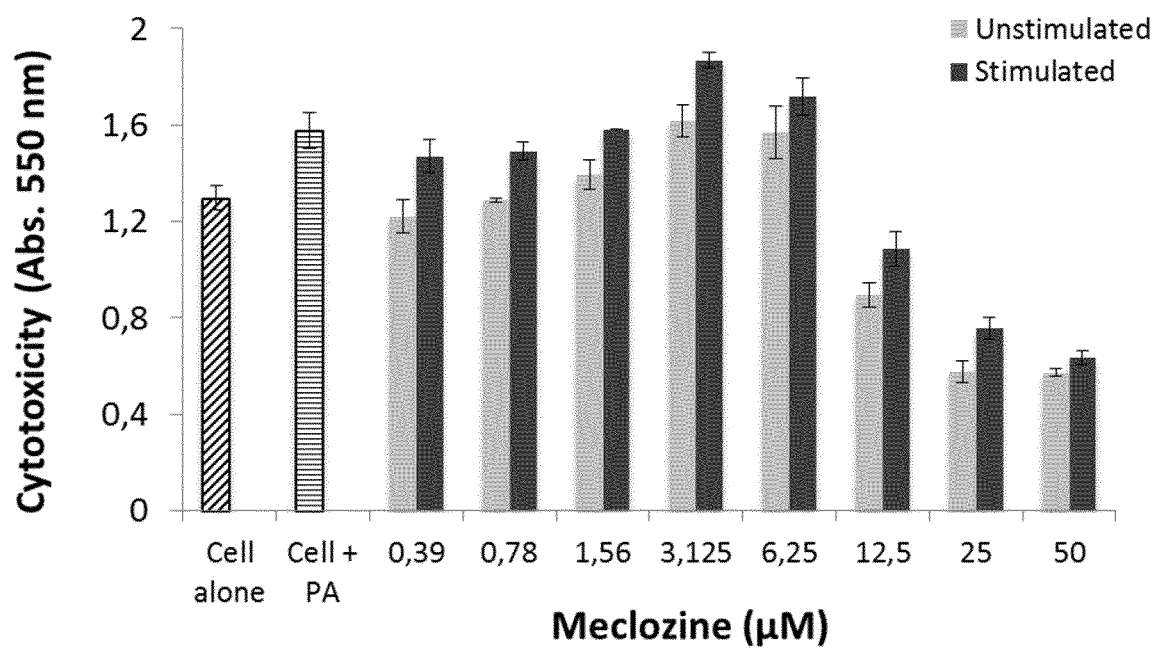

Biological Activities of the Compounds According to the Invention

Materials and Methods

Bacterial strain and conditions of growth. *P. acnes* strain 6919 was obtained from the American Type Culture Collection (Manassas, Va.) and *P. acnes* strains RON and PIE were isolated from patient with joint infection. All strains were grown under anaerobic conditions in reinforced clostridial liquid and solid medium (RCM) (Difco Laboratories, Detroit, Mich.). *P. acnes* was transferred from the bacterial stock onto RCM agar plate and incubated for 5 days under anaerobic condition by using a GasPak™ EZ Anaerobic Container System (Becton Dickinson & Co, Sparks Md., USA). A single colony was transferred into 100 ml RCM and grown as described above. Bacterial suspension was then store frozen at −80° C. in presence of 10% glycerol final. This stock was called «start stock» and used for all the experiments. For routine culture, 100 ml of RCM was used and bacteria were harvested after 5 days at 37° C. by centrifugation at 7,000×g for 10 min at 4° C. Pellets were pooled and washed in about 30 ml of cold sterile PBS [1.5 mM $KH_2PO_4$, 2.7 mM $Na_2HPO_4.7H_2O$, 0.15 M NaCl (pH 7.4)] and centrifuged again as described above. Finally, the bacterial pellet was suspended in sterile PBS (1:10 from volume culture).

Cell culture, pretreatment and stimulation. The immortalized human keratinocyte cell line HaCaT, fibroblast MRC5 were grown in Dulbecco's modified Eagle's medium-Glutamax-I (DMEM) with 1 mM sodium pyruvate. The immortalized human monocytic cell line ThP1 was grown in Roswell Park Memorial Institute 1640 Medium-Glutamax-I (RPMI). DMEM and RPMI were supplemented with 0.1% and 10% heat-inactivated fetal calf serum (Invitrogen), and an antibiotic/antimycotic solution (10 U/ml Penicillin, 10 □g/ml Streptomycin, 0.25 □g/ml Amphoterin) at 37° C. in humidified atmosphere containing 5% CO2 as described (Life Technologie). Primary human keratinocytes (NHDK) and fibroblast (HDF) were grown in the KGM-Gold and in FGM-2 Bullet Kit, respectively, as described by the manufacturer (Lonza). The immortalized cell lines were routinely tested to assess the absence of Mycoplasma infection. Cells, cultivated in 6- or 96-well polystyrene plates, were pretreated with appropriate molecule solution for 1 to 48 h at 37° C. in the dark at the appropriate concentration. Then, for stimulation, cells were incubated for 15 min to 24 h with the *P. acnes* suspension adjusted at the appropriate concentration at 37° C. in 5% CO2. For experiences using an in vitro model of psoriasis, the primary human keratinocytes (NHDK) were grown in culture medium for 24 hours. The medium was removed and replaced with culture medium containing meclozine, diclazuril and JAK inhibitor (used as positive control) at the concentrations of 0.39, 0.78, 1.56, 3.12, 6.25 and 12.5 μM and the pro-inflammatory mixture M5 (combination of IL-17A, OSM, TNF-α, IL-22, IL-1a at 10 ng/ml) was added to the cells followed by an incubation for 48 or 72 hours.

Cell viability assays. Viability of cells was estimated by using the MTT assay where cells were incubated with a 0.2% MTT solution in cell culture medium for 4 h at 37° C. The MTT solution was then discarded and DMSO added to solubilize the MTT-formazan cristals produced in living cells. After thorough mixing, the absorbance was measured at 540 nm.

ELISA. Human IL-1β, IL-8, hBD-2 and TNF-α protein concentration were measured in the supernatants of stimulated cells using various ELISA Sets (all from Ready-Set-Go from eBioscience, except hBD-2 measurements: Human DEFB4A/BD-2 ELISA Kit from LSBio) according to the manufacturer's instructions. We used serial dilutions of recombinant human IL-1β, IL-8, hBD-2 and TNF-α for standard curve. The optical density was determined at 450 nm at a wavelength correction of 540 nm.

RT-qPCR assay. Cells were grown in 6 wells polystyrene plate and pretreated for 24 h with diclazuril and meclozine at 10 μM and stimulated 5 h by *P. acnes* as described previously. Total RNA was isolated using the NucleoSpin RNA and treated with DNAse I, according to the manufacturer's instructions (Macherey-Nagel, Hoerdt, France). RNA concentration was determined at 260 nm on a nanodrop (Labtech, France) and the ratios for all samples were ranging between 1.6 and 1.9. Complementary DNA were generated from 100 ng of total RNA at 50° C. for 10 min followed by the quantitative PCR analysis, carried out in the LightCycler Nano (Roche), and performed with the iTaq Universal SYBR Green One-Step kit (Bio-Rad Laboratories, Hercules, Calif., USA) with a 2-step cycles conditions set at 95° C. for 60 s followed by 40 cycles of 95° C. for 15 s, 68° C. for 60 s, and ended by a melting curve at 65-95° C., 60 s with 0.1° C./s. From the amplification curves, the threshold cycles (Ct) are determined for the studied genes. The amount of relative RNA in stimulated cells relative to control cells is calculated according to the method of 2Δct and expressed as a relative fold change expression normalized to gene expression of internal control (GAPDH). IL-8 primers used: sens 5'-TCTTGGCAGCCTTCCTGATT-3', anti-sens 5'-TTTCGTGTTGGCGCAGTGT-3' and GAPDH primers: sens 5'-GCCACATCGCTCAGACAC-3', GADPH anti-sens 5'-GCCCAATACGACCAAATCC-3'. Sample quantification was made in triplicate.

Western Blot analysis. Whole cell protein extracts (25 μg) were separated by electrophoresis (LDS-PAGE) under denaturing conditions with NuPAGE Novex 4-12% Bis-Tris gel (1 mm, 12 wells, Invitrogen, UK) and proteins were transferred onto nitrocellulose membranes and saturated in 20 ml of saturation buffer consisting of TBS 1X (Tris Buffered Saline) containing 200 mM Tris, 1.4 M NaCl (pH 7.6), 5% no fat milk, 0.1% Tween 20 for 1 h. After washing three times for 15 min with 15 ml of TBS/T buffer [1X TBS, 0.1% Tween-20], membranes were incubated overnight with gentle mixing at 4° C. with 10 ml of rabbit polyclonal primary antibodies against human ICAM-1 (SC-7891, 1:500), PPARa (SC-398394, 1:250), PPARb (SC-74517, 1:200), PPARg (SC-7196, 1:500), IkB (SC-371, 1:500), p-IkB (SC-7977, 1:500), Cox-2 (SC-7951, 1:250), p-mTOR (CS, Ref 2974, 1:1000), mTOR (CS, Ref 2972, 1:1000), p-p38 (SC-17852, 1:500), p38 (SC-535, 1:250), ERK (SC-94, 1:500), JNK (SC-571, 1:500), and mouse monoclonal primary antibodies against human p-PI3 kinase (CS, Ref 4228, 1:250), PI3 kinase (CS, Ref 4257, 1:250), p-Akt1/2/3 (SC-81433, 1:500), p-ERK (SC-7383, 1:500), p-JNK (SC-6254, 1:500), b-actin used to control loading, (SC-47778, 1:1000) diluted in TBS/T supplemented with 5% BSA (antibodies were purchased from Santa Cruz Biotechnology, Inc., Santa Cruz, Calif., USA abbreviated SC; and from Cell Signaling Technology, Inc. Leiden, The Netherlands abbreviated CS above). After washing to remove unbound antibodies, bound primary antibodies were detected by incubation for 1 h using secondary antibody against rabbit- and mouse IgG (Santa Cruz Biotechnology, SC-2357, 1:5000 and SC-2005, 1:5000, respectively). Unbound material was removed by washing and peroxidase activity was detected in a chemiluminescence assay (WesternBright ECL, Advansta, Menlo Park, USA).

Statistical analysis. The statistical significance of differences between data from experimental groups was analyzed by paired Student's-test. A level of $P \leq 0.05$ was accepted as significant. Statistical significance is indicated by * (P≤0.05),  (P≤0.01), and * (P≤0.001), respectively.
Results 1. Diclazuril and Meclozine Dose-Dependently Inhibits *P. acnes*-Induced IL-8 Production in Keratinocytes.

Both molecules, diclazuril and meclozine, were purchased separately from Sigma and tested independently on immortalized keratinocytes HaCaT cell for their capacity to inhibit the IL-8 production in a dose-dependent manner. HaCaT cells were pre-treated with diclazuril and meclozine, at the concentrations ranging from 0.39 to 50 µM, for 24 h and then stimulated with *P. acnes* suspension as described in Materials and Methods. The production of IL-8 was measured on culture supernatant by ELISA and the viability of cells was estimated by MTT assay (FIG. 1). For both molecules, diclazuril and meclozine, their capacity to inhibit the production of IL-8 in a dose-dependent manner with an IC50 at about 6 µM (P=0.011) and 3 µM (P=0.0024), respectively (FIG. 1A, B) is confirmed, while no change was observed in pretreated cells without being stimulated. Moreover, no cytotoxicity was observed at the IC50 concentrations (FIG. 1 C, D).

Same results were obtained with two other *P. acnes* strains (RON, PIE) on primary keratinocytes NHDK and fibroblast (HDF) cell lines.

2. Diclazuril and Meclozine Dose-Dependently Inhibits *P. acnes*-Induced IL-β Production in Monocytes.

Figure 2A:
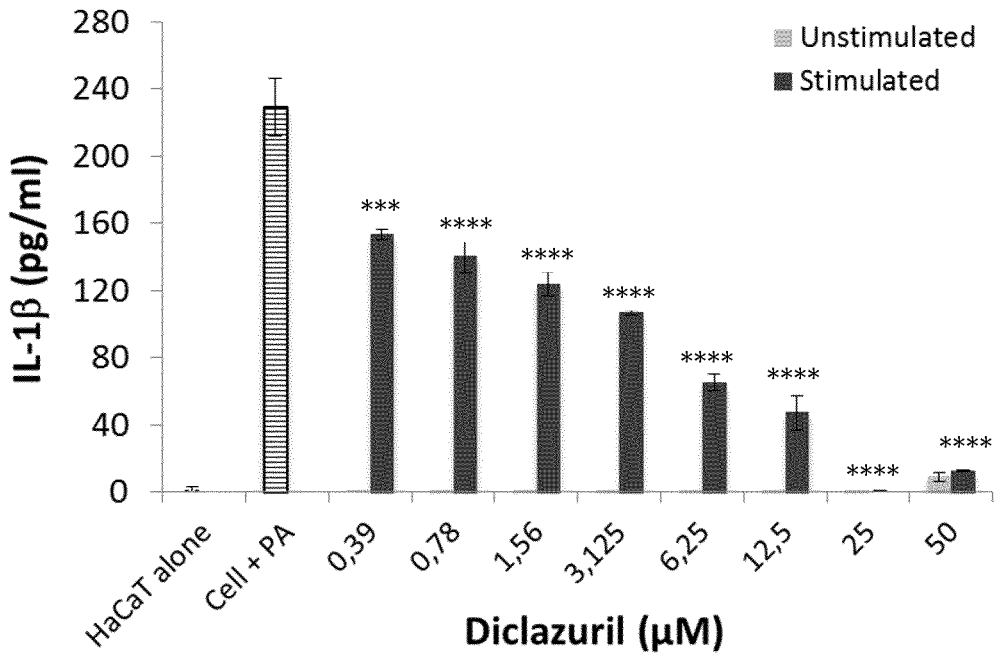
FIG. 2: Dose-dependent inhibition of IL-1β production and cell viability evaluation by monocytes pre-treated with Diclazuril and Meclozine. ThP-1 cell were incubated for 24 h with (A, C) diclazuril and (B, D) meclozine alone at concentrations ranging from 0.39 to 50 μM (gray bar) and stimulated with *P. acnes* (dark bar). Controls experiments were done with ThP-1 cell untreated and unstimulated (hatched bar) and with ThP-1 cells stimulated with *P. acnes* only (horizontal line bar). Measurement of IL-1β production was realized by ELISA and cytotoxicity was determined by the MTT assay as described in Materials and Methods. Data are means±S.D. of three separate experiments. Statistical significance is indicated by * (P<0.05),  (P<0.01), * (P<0.001), and **** (P<0.0001), respectively.
Figure 2B:
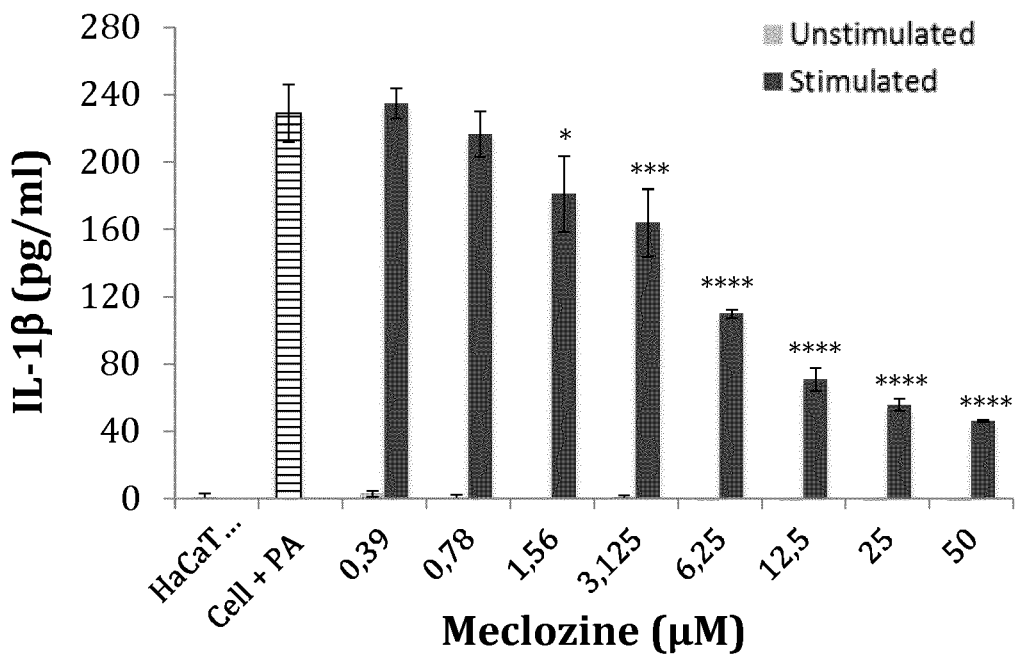
Figure 2C:
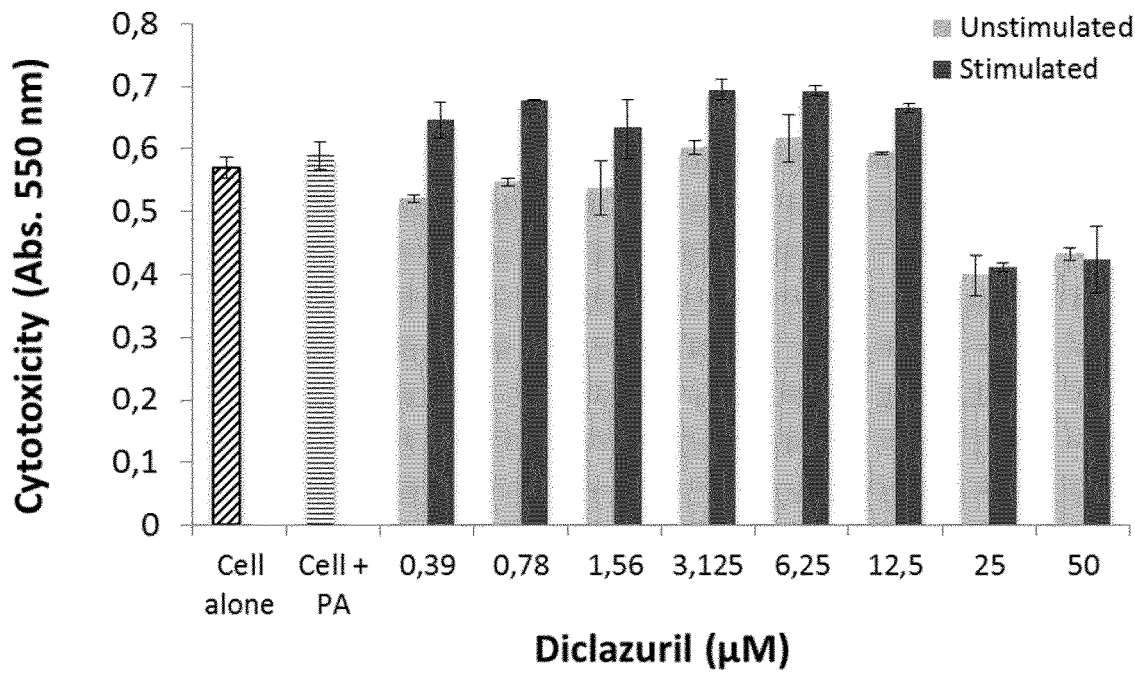
Figure 2D:
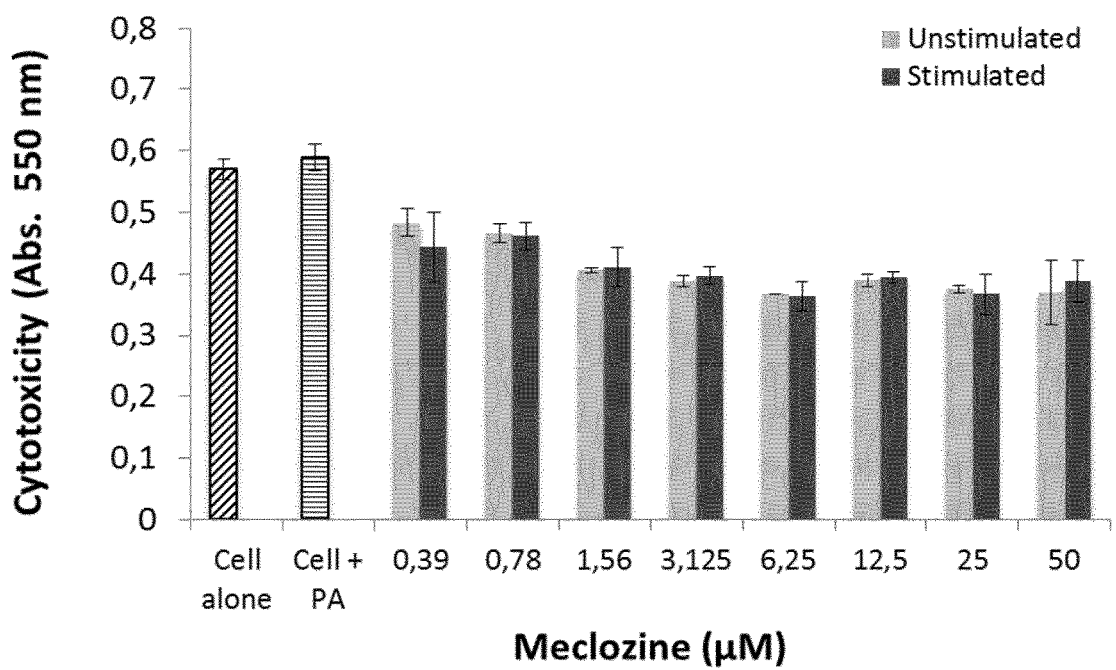

Both molecules, were tested to inhibit the production of IL-1β by the monocytic cell line. ThP-1 cells were pre-treated with diclazuril and meclozine, at the concentrations ranging from 0.39 to 50 µM, for 24 h and then stimulated with *P. acnes* suspension as described in Materials and Methods. The production of IL-1β was measured on culture supernatant by ELISA and the viability of cells was estimated by MTT assay (FIG. 2). It has been shown that diclazuril and meclozine were able to inhibit the production of IL-1β in a dose-dependent manner with an IC50 at about 3 µM for diclazuril (P=5.8 $0.10^{-6}$) and 6 µM for meclozine (P=6.9 $0.10^{-6}$) (FIG. 2A, B), with no cytotoxicity for diclazuril (FIG. 2C) and moderate cytotoxicity at 64% for meclozine (FIG. 2D). In parallel we tested the ability of both molecules, diclazuril and meclozine, to inhibit the production of TNF-α by the monocytic cell line and shown no effect (Data not shown).

3. Diclazuril and Meclozine Inhibit *P. acnes*-Induced IL-8 and IL-1β mRNA Production.

Figure 3A:
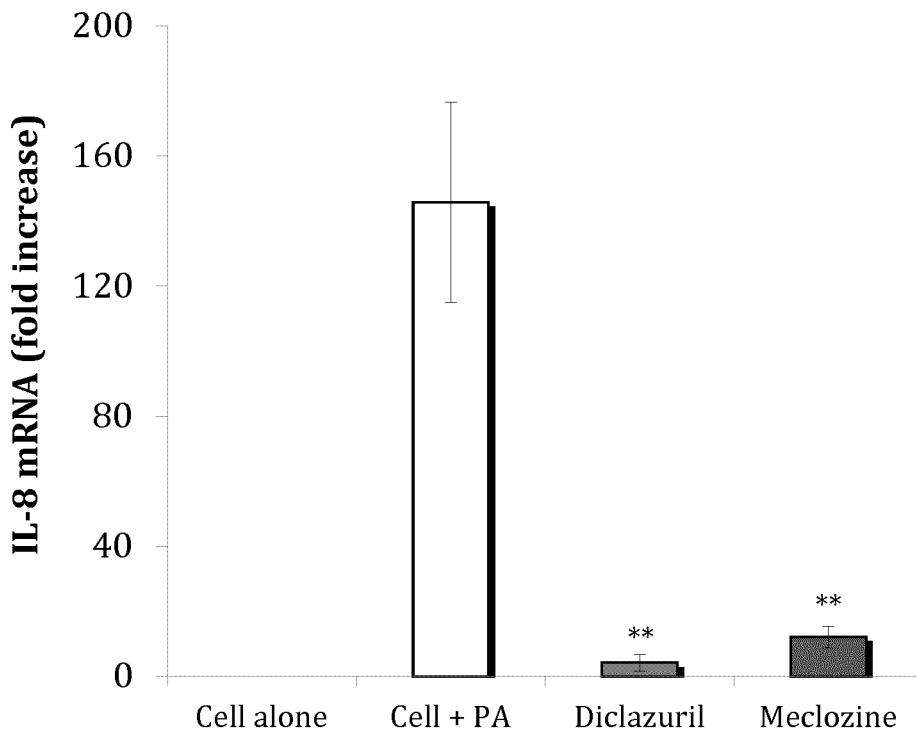
FIG. 3: Diclazuril and meclozine inhibit *P. acnes*-induced IL-8 and IL-1β mRNA productions. (A) HaCaT cells and (B) ThP-1 cells were pre-treated for 24 h by diclazuril (light gray bar) and meclozine (dark gray bar) at 10 μM and then stimulated for 5 h with *P. acnes* suspension ($OD_{600\ nm}$=0.3). Control experiments were done with unpre-treated and unstimulated cells (cell alone) and with cell stimulated by *P. acnes* only (white bar). Total RNA was extracted and IL-8/IL-1β mRNA levels were determined by real-time RT-PCR. IL-8 and IL-1β mRNA levels were compared with GAPDH mRNA level (used as control) and are expressed as foldchange. Data are means±S.D. of three separate experiments. Statistical significance is indicated by * (P<0.05),  (P<0.01), * (P<0.001), and **** (P<0.0001), respectively.
Figure 3B:
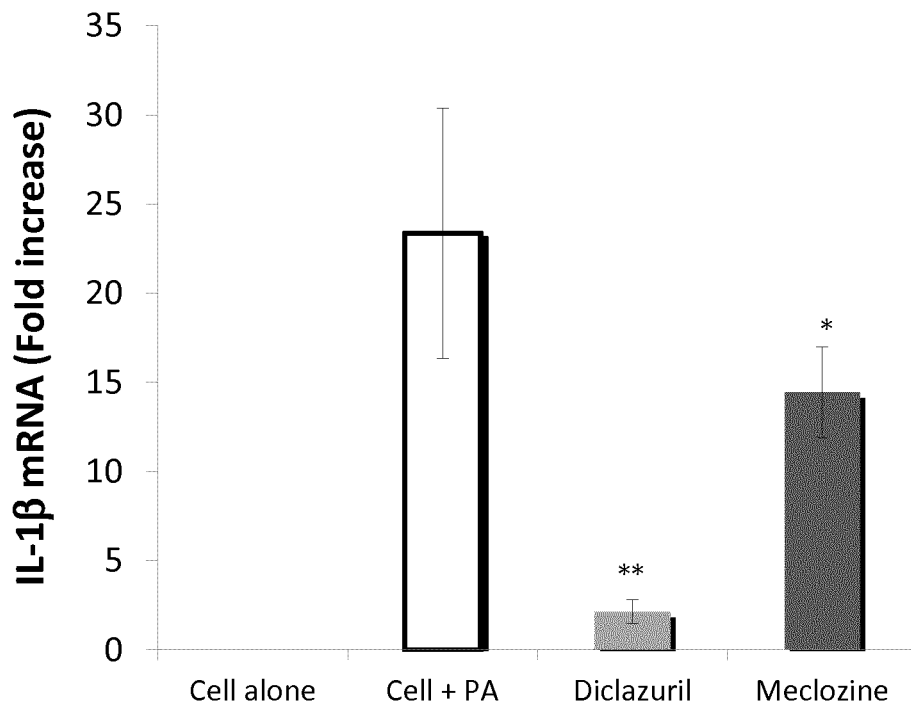

As it has been shown that *P. acnes*-induced IL-8 and IL-1β protein production were inhibited by diclazuril and meclizine, it has been investigated whether IL-8 and IL-1β traductions were also regulated at the mRNA level. RT-qPCR analysis are used to assess the effect of diclazuril and meclozine on the level of IL-8 and IL-1β mRNA production in HaCaT keratinocyte cells and ThP-1 monocyte cells lines stimulated by *P. acnes* (FIG. 3A). Both cell lines were pretreated for 24 h with diclazuril and meclozine at 10 µM and stimulated for 5 h with *P. acnes*. Controls experiments were done with unpretreated/unstimulated cell and with *P. acnes* stimulated cells only. We showed that *P. acnes* strongly induced IL-8 and IL-1β mRNA productions. However, when cells were pretreated with diclazuril and meclozine, mRNA-IL-8 and -IL-1β productions were inhibited by up to 97% in HaCaT cells (P=0.002, P=0.002) (FIG. 3A), and by up to 91% and 38% in ThP-1 cells (P=0.002, P=0.047) (FIG. 3B).

4. Diclazuril and Meclozine Inhibition of MAPK Pathways.

Figure 4A:
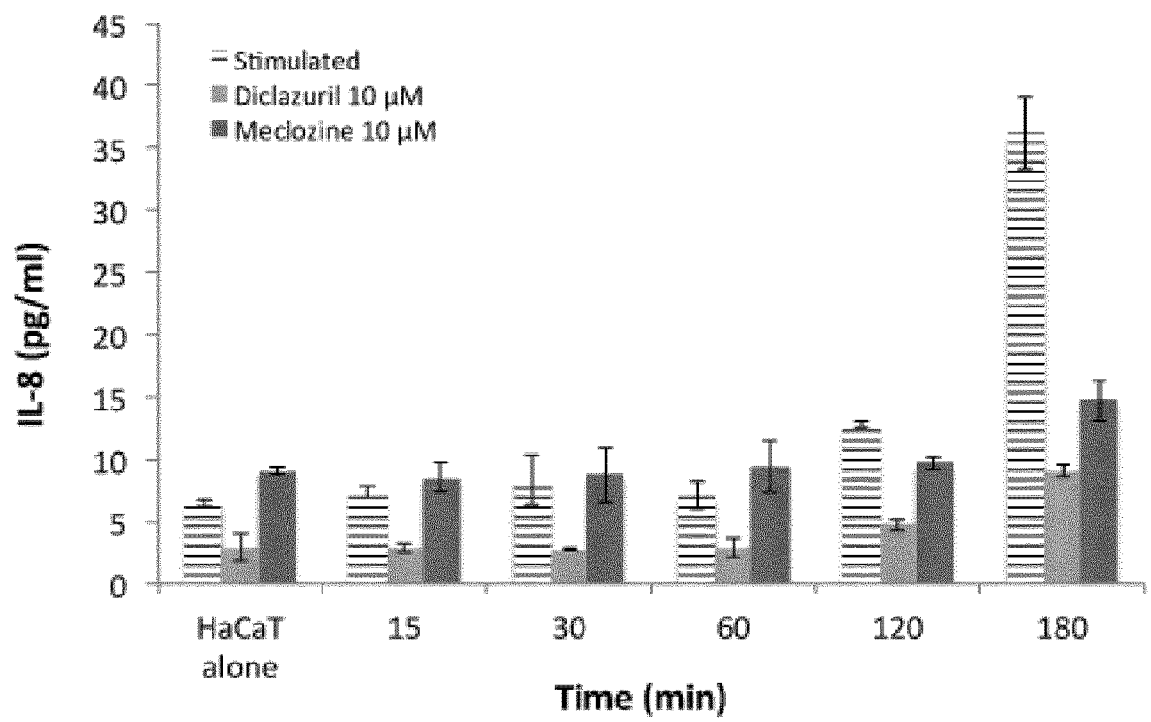
FIG. 4: Diclazuril and meclozine inhibit inflammatory signaling pathways. HaCaT cells were pre-treated for 24 h with diclazuril and meclozine at 10 μM and then stimulated with *P. acnes* for 15, 30, 60, 120 and 180 min. At each time measurement of IL-8 production was realized by ELISA supernatant (A) and whole-cell lysates were prepared and used for IκB (B), (C) p-ERK, western blot analysis, using the appropriate antibodies.
Figure 4B:
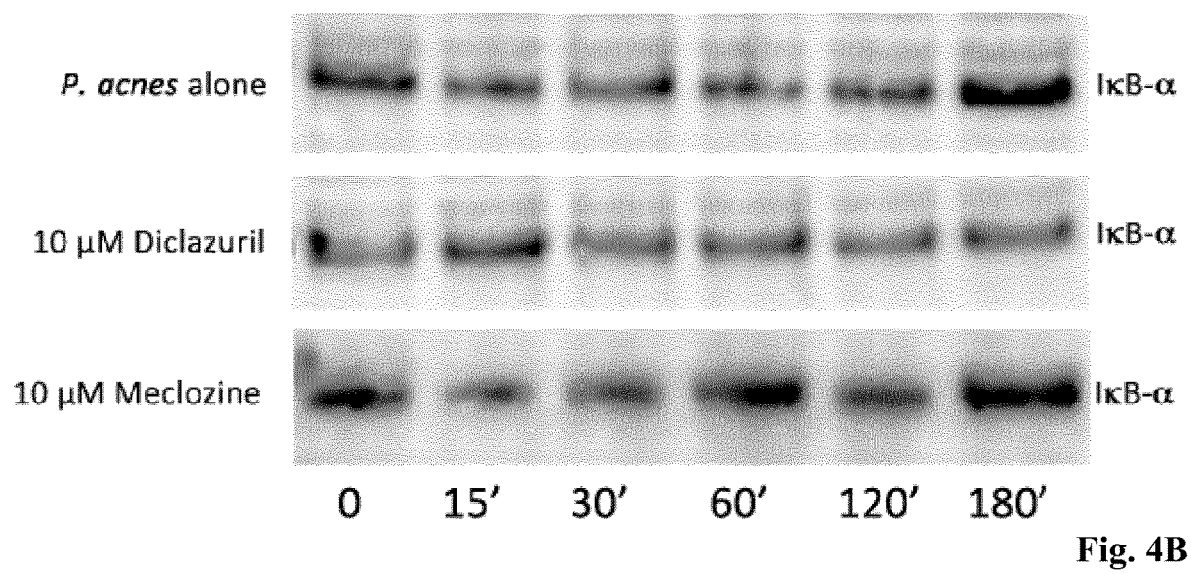
Figure 4C:
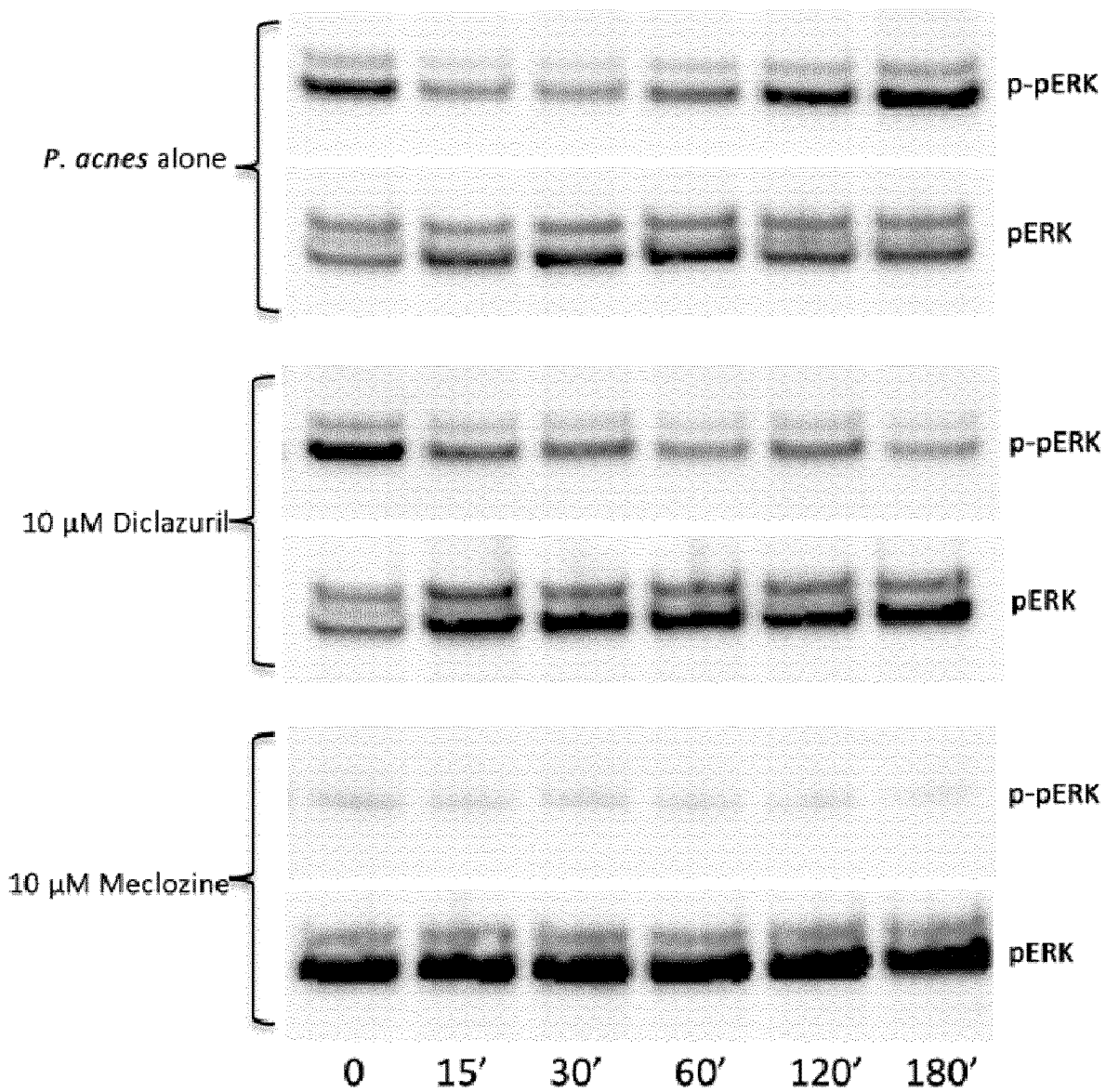

The molecular basis for the inhibition of IL-8 production by diclazuril and meclozine has been investigated, in particular it has been evaluated if they interfered with signaling pathways known to be activated when keratinocytes are stimulated with *P. acnes*. It has first been confirmed the activation of IL-8 production when cells were stimulated by *P. acnes* while pre-treatment with both, diclazuril and meclozine, inhibit such production (FIG. 4A). It has also been confirmed that the activation of TLR-2 by *P. acnes* led to IκB degradation and the stimulation of MAPK pathways in HaCaT cells as a time lag in the response of the HaCaT cell was observed for both the IkB and ERK pathways (FIG. 4B, C, panels *P. acnes* alone). It has been shown that pre-treating HaCaT cells keratinocytes with diclazuril before *P. acnes* stimulation did not prevented the degradation of IκB (FIG. 4B). However, both molecules prevented the phosphorylation of ERKs induced by *P. acnes* (FIG. 4C, panels 10 µM diclazuril, meclozine). Stripping and subsequent reprobing of the blot with antibodies against total ERKs demonstrated no change in total protein levels following *P. acnes* stimulation, suggesting that *P. acnes* activated pre-existing ERKs. These data suggest that the inhibition by diclazuril and meclozine of *P. acnes*-induced IL-8 production in keratinocytes involves downregulation of the MAPK pathways.

5. Diclazuril and Meclozine Inhibit PGN- and LTA-Induced IL-8 and IL-1β Production.

Figure 5A:
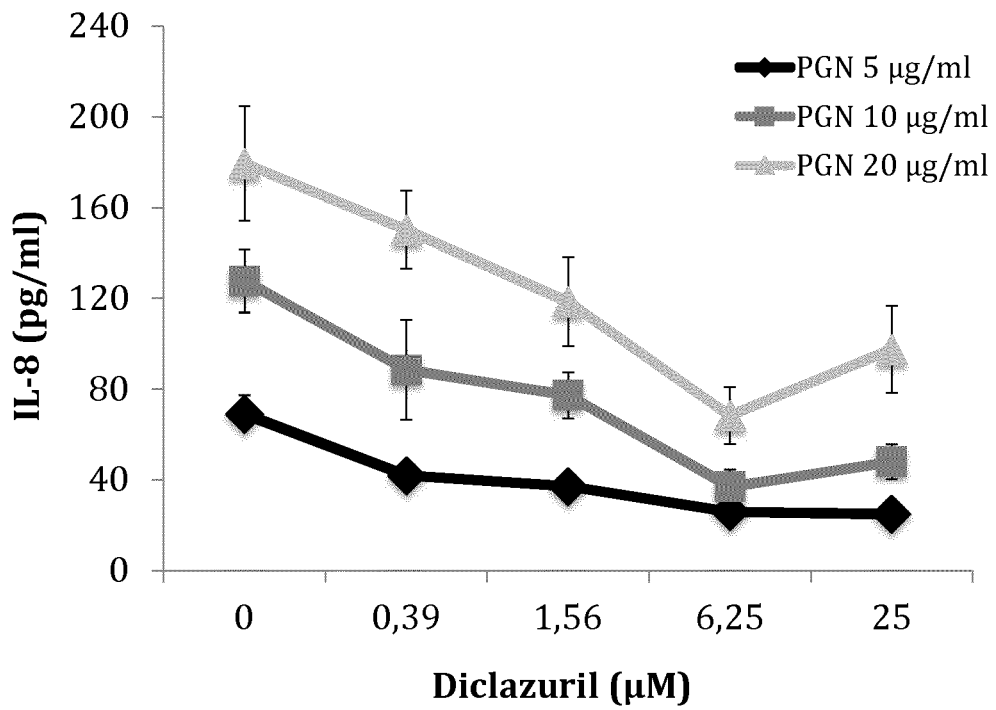
FIG. 5: Dose-dependent inhibition of IL-8 production by keratinocytes pre-treated with Diclazuril and Meclozine and stimulated with PGN. HaCaT cells were incubated for 24 h with (A) diclazuril and (B) meclozine at concentrations ranging from 0.39 to 25 μM and then stimulated with PGN at 5 (light gray curve), 10 (middle gray curve), and 20 μg/ml (dark gray curve). Controls experiments were done with untreated HaCaT cells. Measurement of IL-8 production was realized by ELISA as described in Materials and Methods. Data are means±S.D. of three separate experiments.
Figure 5B:
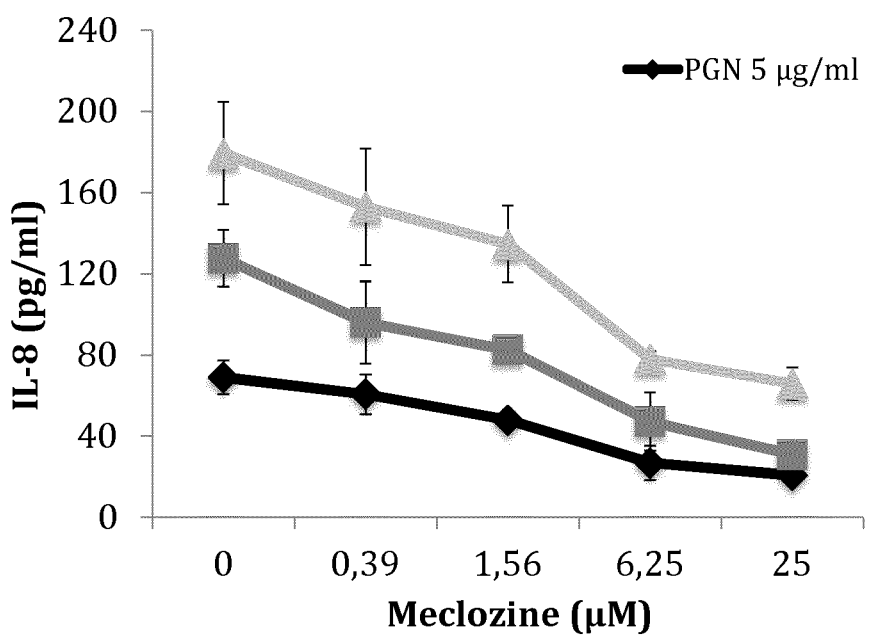

Previously it has been shown that diclazuril and meclozine were able to inhibit IL-8 and IL-1β productions at the transcriptional and traductional levels in pretreated cells stimulated with *P. acnes*. Here, it is investigated if the nature of the cell stimuli would have an impact on the diclazuril and meclozine effects on the IL-8 and IL-1β productions. Both, HaCaT and ThP-1 cell lines were pre-treated with several concentrations of diclazuril and meclozine ranging from 0.39 to 25 µM for 24 h, and then stimulated with 3 different concentrations of peptidoglycanne (PGN) and lipoteicoic acid (LTA) at 5, 10 and 20 µg/ml for 18 h at 37° C. Levels of IL-8 and IL-1β productions were measured by ELISA on the culture supernatants and shown in FIGS. 5 and 6. It is showed that IL-8 production dose-dependently increase when cell are only stimulated with various concentrations of PGN (5, 10, 20 µg/ml) starting at about 70 pg/ml, raising up to 130 and 180 pg/ml. Pretreatment of keratinocytes with diclazuril decreased the production of IL-8 by an average of 65% at 6.25 µM regardless of the initial PGN dose used (FIG. 5A). Same results were obtained with meclozine and at 6.25 µM the IL-8 production was reduced by 60% (FIG. 5B).

Figure 6A:
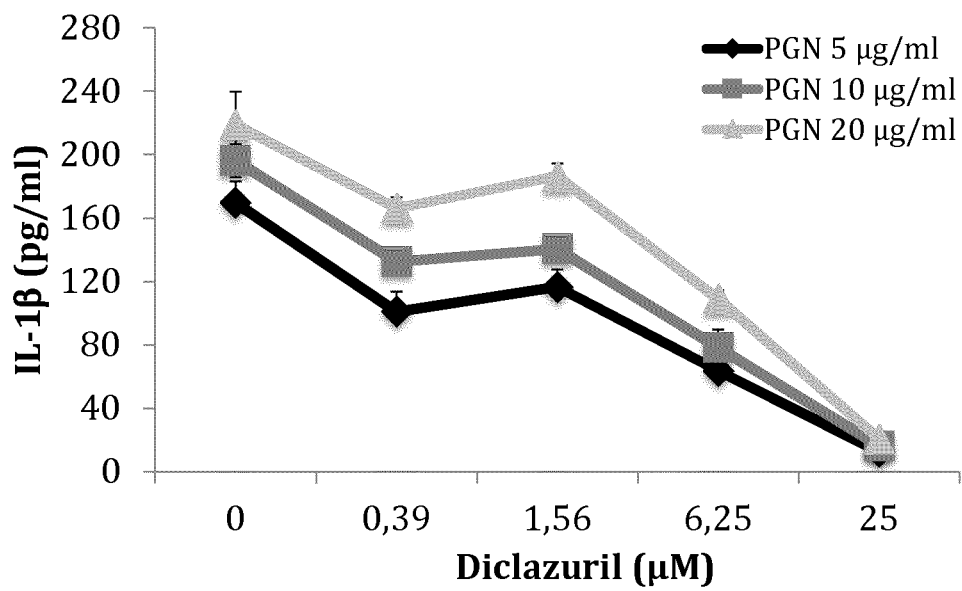
FIG. 6: Dose-dependent inhibition of IL-1β production by monocytes pre-treated with Diclazuril and Meclozine and stimulated with PGN and LTA. ThP-1 cells were incubated for 24 h with (A, C) diclazuril and (B, D) meclozine at concentrations ranging from 0.39 to 25 μM and then stimulated with PGN (A, B) and LTA (C, D) at 5 (light gray curve), 10 (middle gray curve), and 20 μg/ml (dark gray curve). Controls experiments were done with untreated ThP-1 cells. Measurement of IL-1β production was realized by ELISA as described in Materials and Methods. Data are means±S.D. of three separate experiments.
Figure 6B:
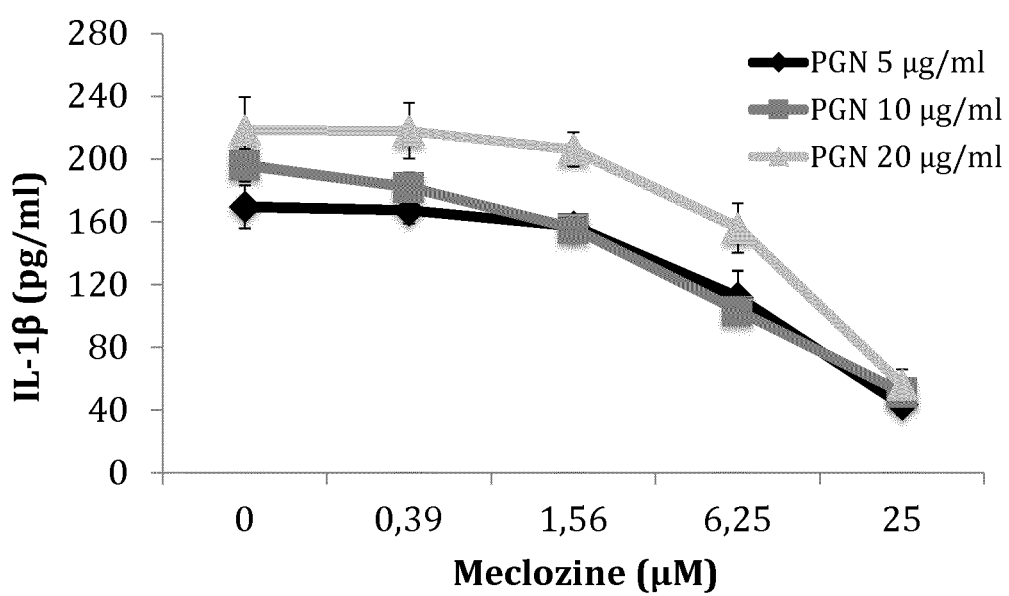
Figure 6C:
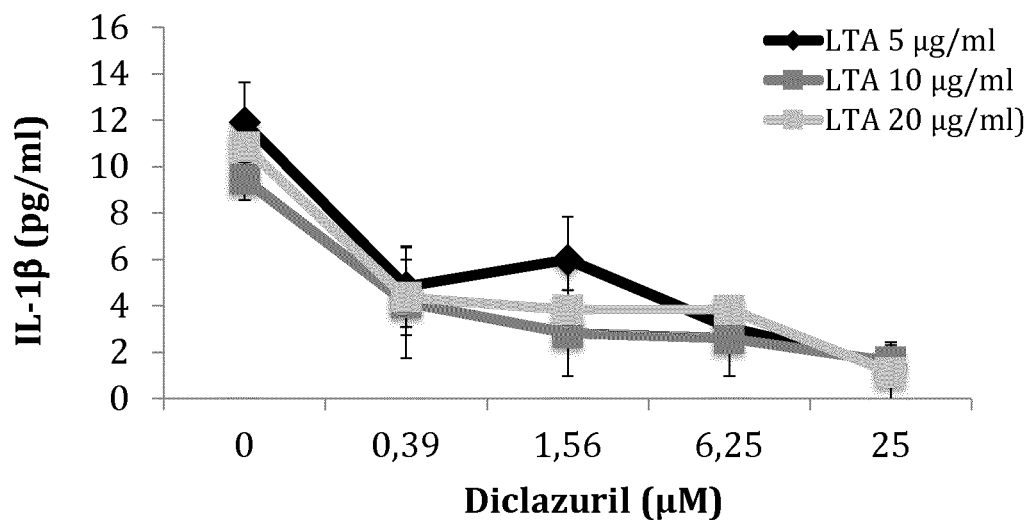
Figure 6D:
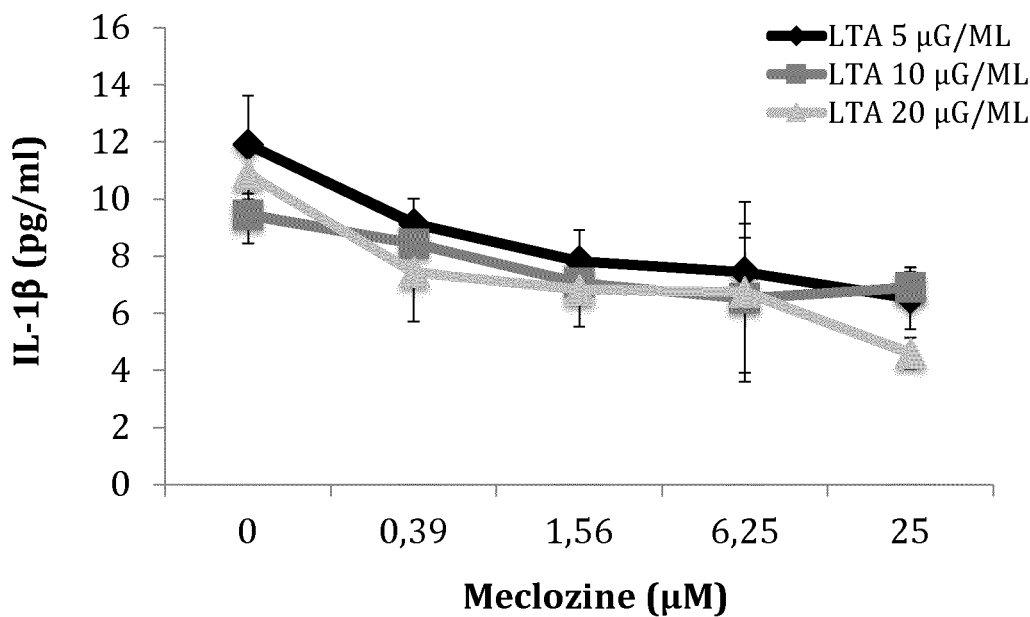

To assess the effect of diclazuril and meclozine on the IL-1β production, monocytic ThP-1 cell line stimulated either by PGN and LTA is used. It has been shown that the production of IL-1β was induced from 170 to 210 pg/ml with PGN (FIG. 6A, B) and from 9 to 12 pg/ml with LTA (FIG. 6C, D). Pretreatment of cells with diclazuril and meclozine, dose-dependently inhibited the IL-1β production. Pretreatment at 6.25 µM with diclazuril decreased the IL-1β production by an average of 64% (FIG. 6A, C), and with meclozine by an average of 36% (FIG. 6B, D).

6. Time-Dependent Effect of Keratinocyte Pre-Treatment on IL-8 Production.

Figure 7A:
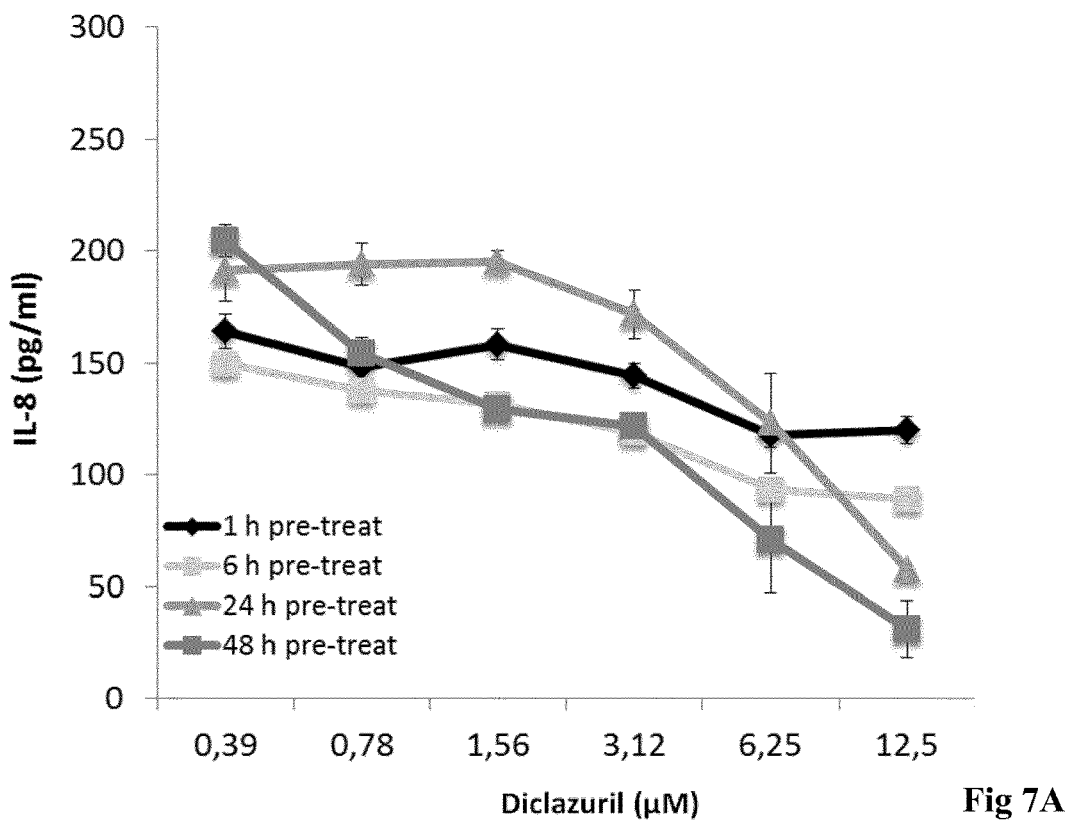
FIG. 7: Time-dependent effect of diclazuril and meclozine pre-treatment. HaCaT cells were pre-treated with diclazuril (A, C) and meclozine (B, D) at concentrations ranging from 0.39 to 12.5 μM for 1 h (light gray curve), 6 h (middle gray curve), 24 h (dark gray curve), and 48 h (black curve), and then stimulated by *P. acnes* for 18 h. Measurement of IL-8 production was realized by ELISA and cytotoxicity was determined by the MTT assay as described in Materials and Methods. Data are means±S.D. of three separate experiments.
Figure 7B:
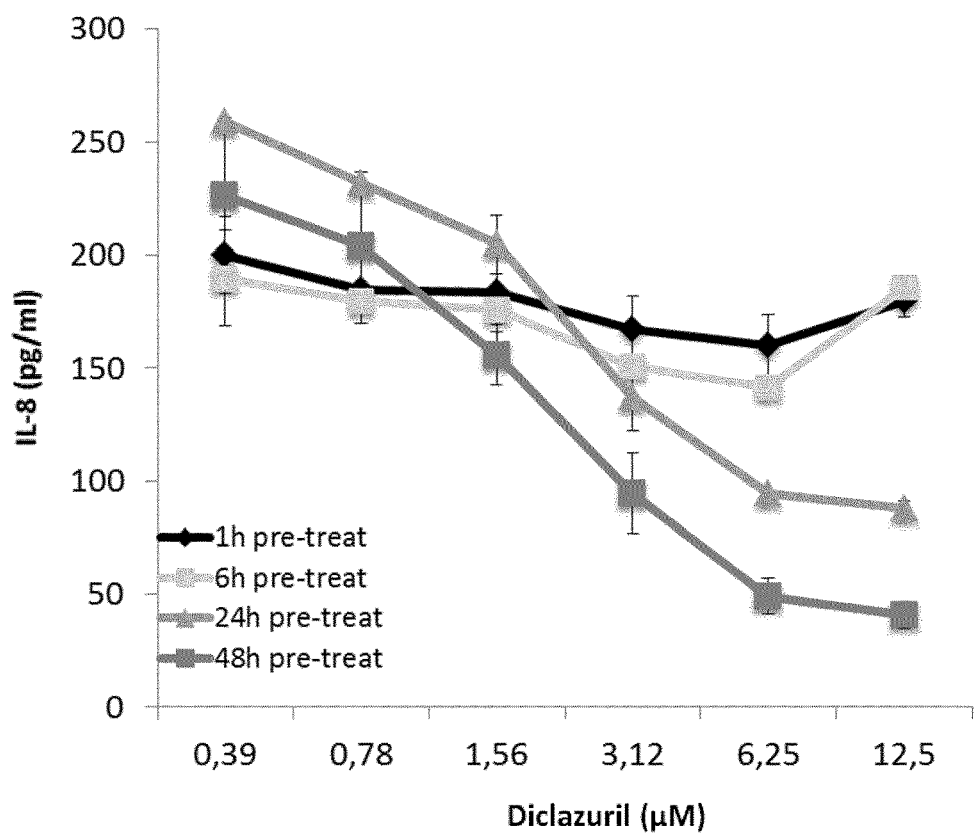
Figure 7C:
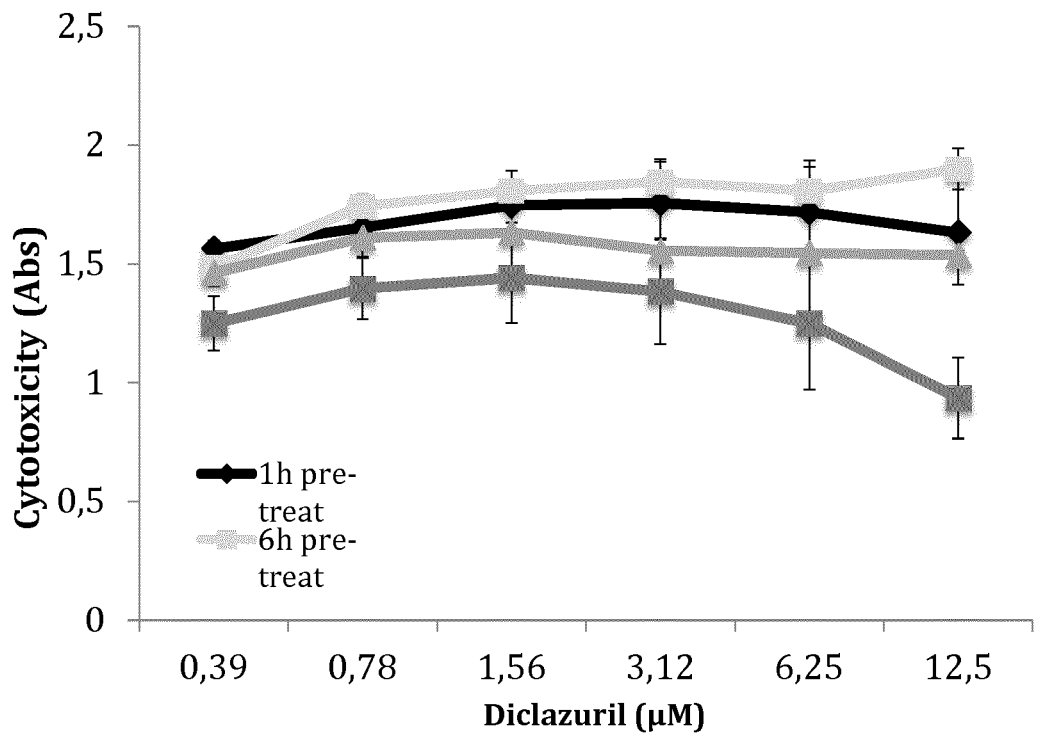
Figure 7D:
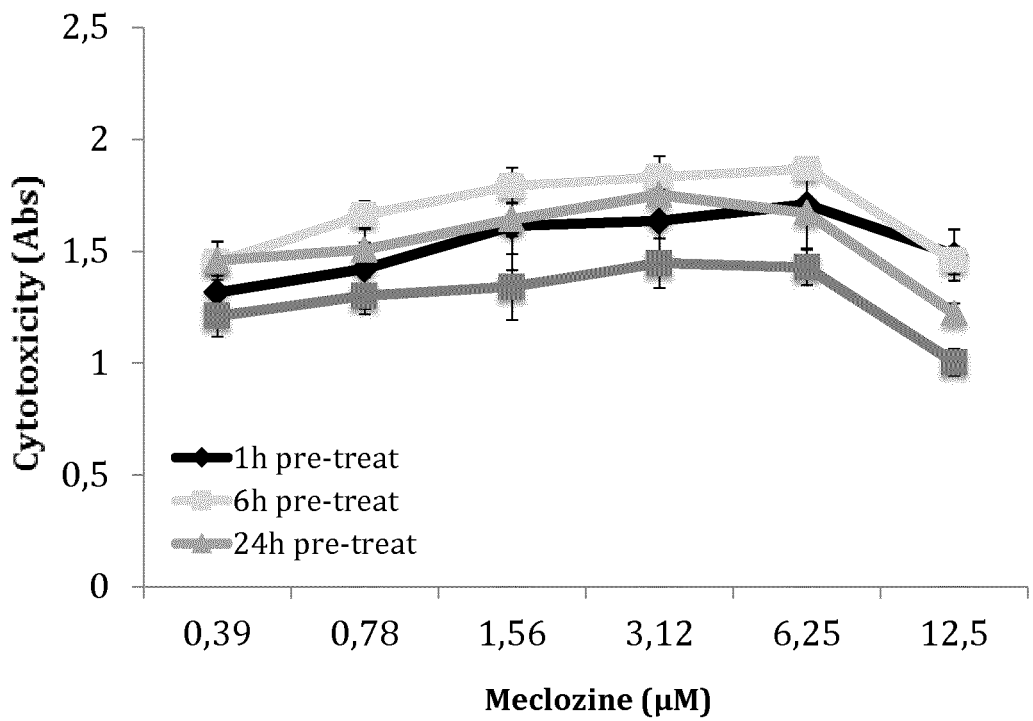

In this experiment the effect of various time of keratinocytes pretreatment by diclazuril and meclozine on the IL-8 production is evaluated. Keratinocyte HaCaT cell line was pretreated for 1, 6, 24 and 48 h with diclazuril and meclozine at concentrations ranging from 0.39 to 12.5 µM and then stimulated with *P. acnes* (FIG. 7). For 1 and 6 h pretreatment, both molecules did not reduce significantly the IL-8 production (FIG. 7A, B). After 24 h pretreatment, we confirmed the effect of diclazuril and meclozine by reducing the IL-8 production by 36% (P=0.03) and 63% (P=0.00004) at 6.25 µM, respectively. Interestingly, when cell pre-treatment was raised to 48 h the IL-8 production decrease by 65% (P=0.0004) with diclazuril and with 78% (P=0.0002) with meclozine (FIG. 7A, B) without any major impact on cell viability (FIG. 7C, D). Here we shown that increasing pre-treatment time of cell contribute to enhance the IL-8 production.

7. Comparison Between Diclazuril and Meclozine With Molecules Used in Acne Treatment.

Figure 8A:
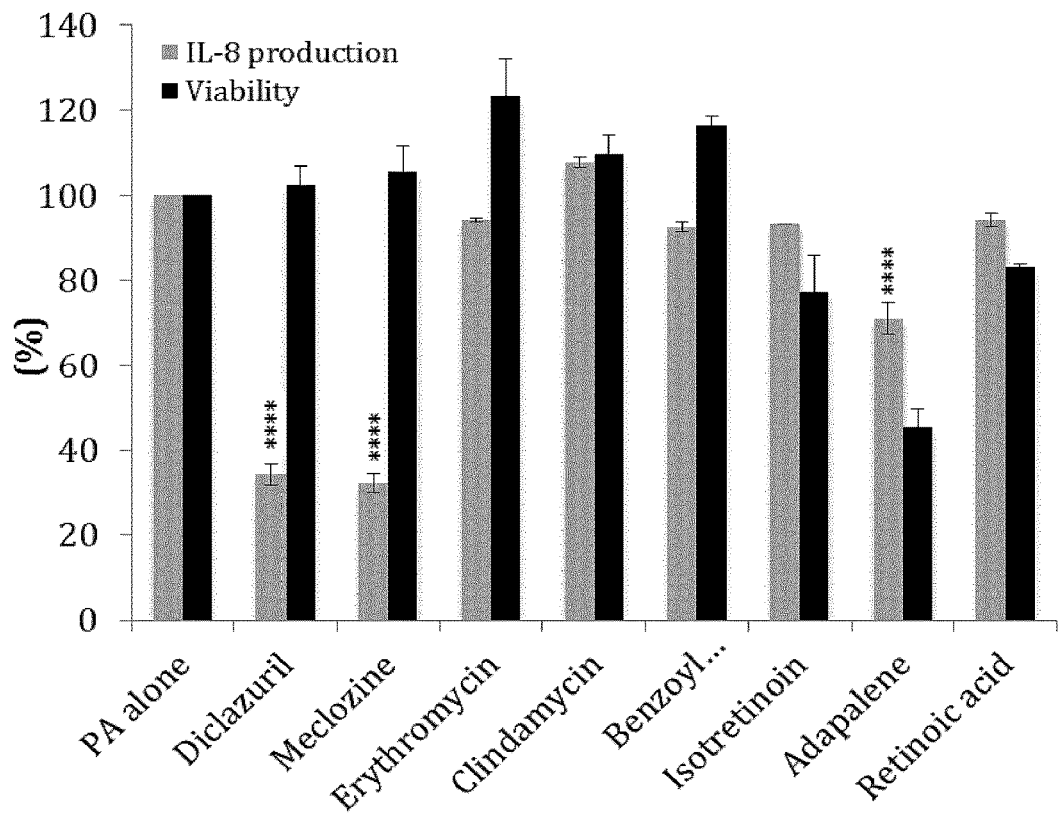
FIG. 8: Comparison effect on IL-8 production between diclazuril and meclozine with common commercial molecules used in acne treatment. HaCaT cells were pre-treated with diclazuril, meclozine, erythromycine, clindamycine, Luperox (benzoyl peroxide), isotretinoine, adapalene and retinoic acid at 6 μM (A) and 12.5 μM (B) for 24 h, and then stimulated by *P. acnes* for 18 h. Controls experiments corresponded to unpre-treated but *P. acnes* stimulated HaCaT cell (PA alone). Measurement of IL-8 production (gray bar) was realized by ELISA and cytotoxicity (black bar) was determined by the MTT assay as described in Materials and Methods. Data are means±S.D. of three separate experiments. Statistical significance is indicated by * (P<0.05),  (P<0.01), * (P<0.001), and **** (P<0.0001), respectively.
Figure 8B:
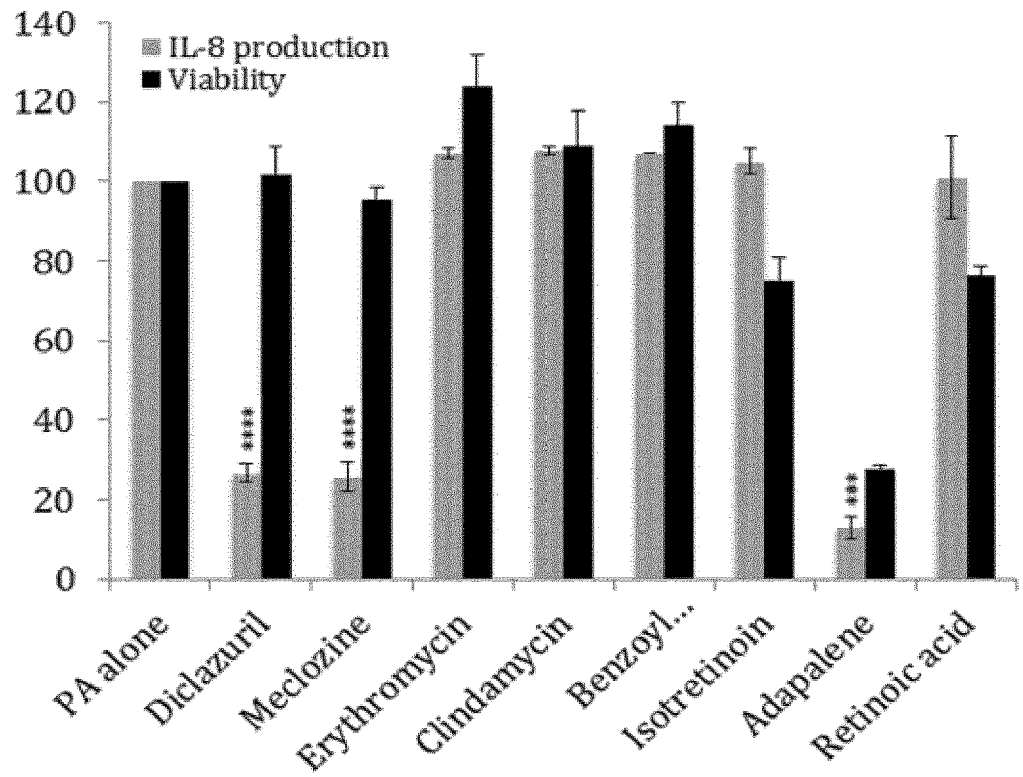

In this experiment we compared the effect of diclazuril and meclozine with the most common molecules (antibiotics, benzoyl peroxide, retinoids) used in the treatment of acne on the IL-8 production. Keratinocyte HaCaT cell was pretreated for 24 h with all molecules at 6.25 and 12.5 µM and then stimulated with *P. acnes* (FIG. 8). As we shown before, diclazuril and meclozine were able to decease the IL-8 production by >60% with no toxicity. In parallel, antibiotics erythromycine and clindamycine as well as benzoyl peroxide have very low none significative or no effect on the IL-8 production with no toxicity. However, we show that retinoids are able to decrease moderately the IL-8 production. Isotretinoin and retinoic acid are able to decrease IL-8 production by 5% and adapalene significantly by 20%. All retinoids exhibits cytotoxicity at about 20% for isotretinoin and retinoic acid and at about 60% for adapalene (FIG. 8A). Moreover, when the concentration of all molecules tested was raised up to 12.5 µM (FIG. 8B), we confirmed the strong effect of diclazuril and meclozine on IL-8 production with no cytotoxicity. However, the other molecules have no effect beside the adapalene witch shown a IL-8 reduction by 90% but associated with 75% cytotoxicity.

8. Capacity to Inhibit the Inflammatory Reaction Induced by *P. acnes* in an In Vivo Model of Inflammation.

According to previous results showing in vitro efficacy of both molecules on the anti-inflammatory response, we tested their capacity to inhibit the inflammatory reaction induced by *P. acnes* in an in vivo model of inflammation.

This model is based on the capacity of mouse ears to react while *P. acnes* is intradermally injected. The inflammatory reaction is evaluated each day over a period of 4 days after *P. acnes* injection by measuring the thickness of the ears, the redness as well as the presence of a desquamation and/or small pustules. At the end of the experiment, final measurement of inflammation was realized and photographic pictures of ears were taken. Then, mice were euthanized and ears were immediately fixed in a formalin-containing buffer for a future histological analysis.

The experimental design consisted of 3 groups containing 10 mice each. 1) PBS corresponds to the non-treated group injected with PBS. 2) PA+Vehicle TOPIC corresponds to *P. acnes* injected in ears treated with Vaseline alone. 3) PA+diclazuril corresponds to *P. acnes* injected in ears treated with 1.3% diclazuril mixed with Vaseline.

The preparation of the 1.3% diclazuril gel consisted of extemporaneously gently mixing 6.5 mg of diclazuril with 0.5 mg of Vaseline for 1 min at room temperature (21° C.) and then directly applied to the mouse ears.

Figure 9A:
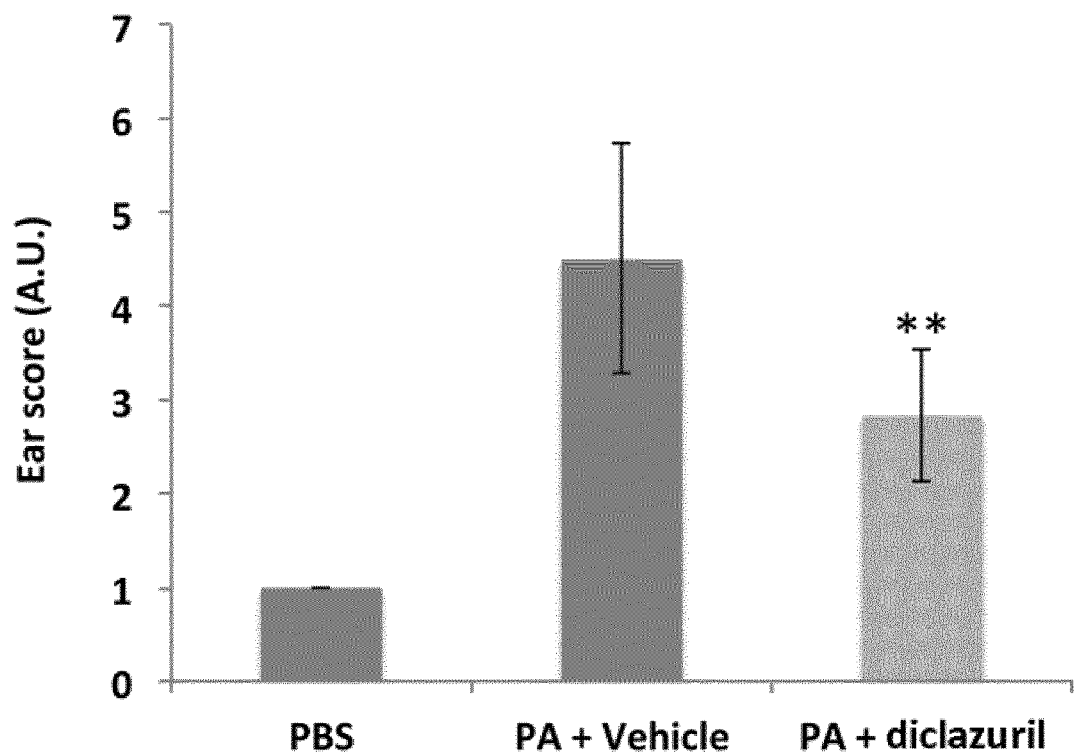
FIG. 9: Effect of VNPA-A2 gel topical application on *P. acnes*-induced inflammation in vivo. Ears of mice were intradermally injected with *P. acnes* ($OD_{620\ nm}$=1.0 corresponding to $2.10^7$ CFU/20 μl in PBS) to induce inflammation. Subsequently, 1.3% diclazuril gel was applied on the ear skin surface of mice each day for 3 days. (A) The score corresponding to the ear thickness, the peeling and the redness, was measured every day for a period of 96 h. Data are means±S.D. of 10 individual experiments. PBS corresponds to the non-treated group injected with PBS. PA+Vehicle corresponds to *P. acnes* injected in ears treated with Vaseline alone. PA+diclazuril corresponds to *P. acnes* injected in ears treated with 1.3% diclazuril mixed with Vaseline. Statistical significance is indicated by * (P<0.05),  (P<0.01), * (P<0.001), and **** (P<0.0001), respectively.
Figure 9B:
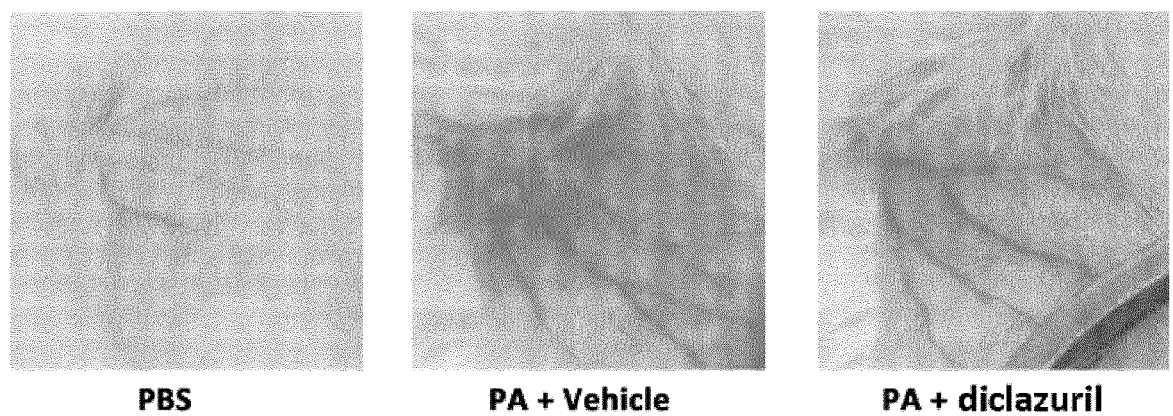

The results are exposed in FIG. 9. It has been shown that diclazuril VNPA-A2 is able to decrease the ear inflammation in topical application by 37% (FIG. 9A).

9—Complementary Data for Chemical Diclazuril Analogue Testing

Diclazuril-Analogue RCL PH000645-PH Dose-Dependently Inhibits *P. acnes*-Induced IL-8 Production in Keratinocytes.

Figure 10:
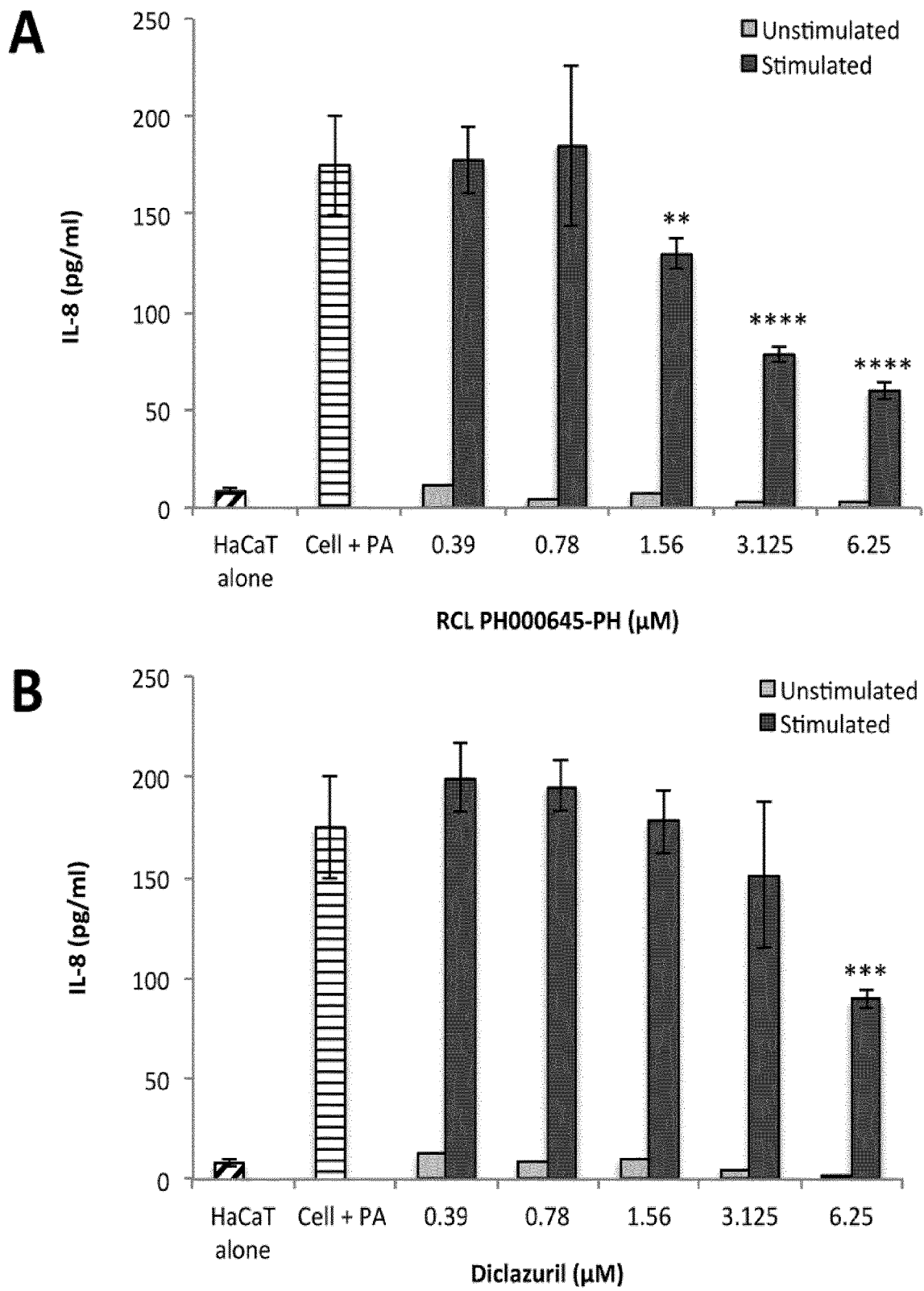
FIG. 10: Dose-dependent inhibition of IL-8 production by keratinocytes stimulated by *P. acnes* pre-treated with the RCL PH000645-PH analogue. HaCaT cell were incubated for 24 h with RCL PH000645-PH (A) and diclazuril (B) at concentrations ranging from 2.5 to 6.25 μM (gray bar) and stimulated with *P. acnes* (dark bar). Controls experiments were done with unstimulated HaCaT cell (hatched bar) and HaCaT stimulated with *P. acnes* (horizontal bar). Measurement of IL-8 production was realized by ELISA as described in Materials and Methods. Data are means±S.D. of three separate experiments. Statistical significance is indicated by * (P<0.05),  (P<0.01), * (P<0.001), and **** (P<0.0001), respectively.
Figure 11:
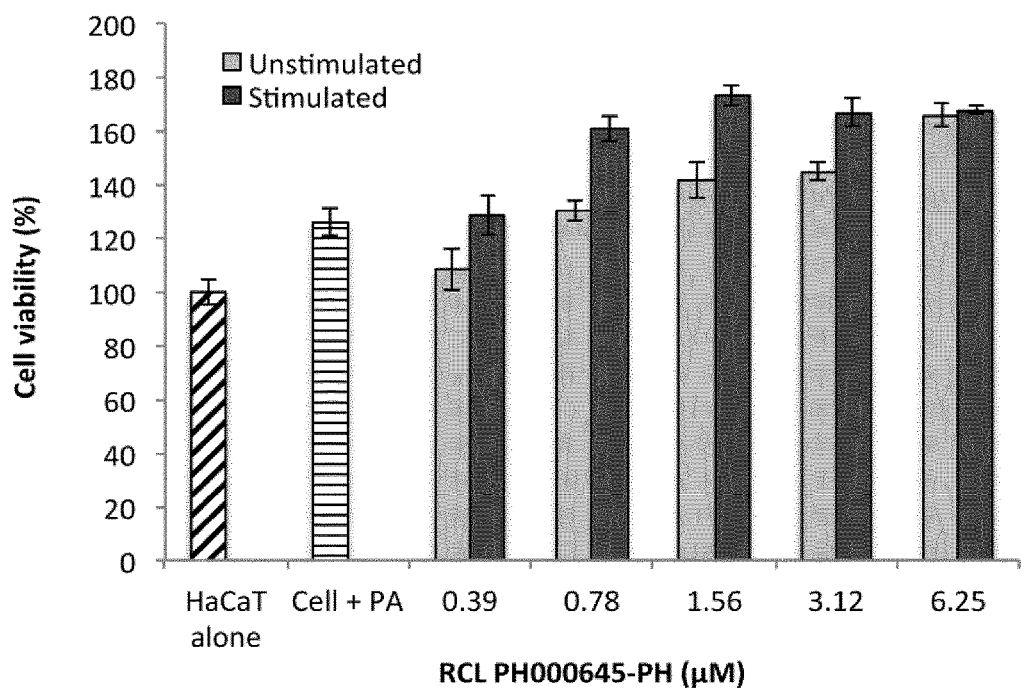
FIG. 11: Evaluation of cell viability after treatment with the RCL PH000645-PH analogue on keratinocytes. HaCaT cell were incubated for 24 h with RCL PH000645-PH (A) and diclazuril (B) at concentrations ranging from 2.5 to 6.25 μM (gray bar) and stimulated with *P. acnes* (dark bar). Controls experiments were done with unstimulated HaCaT cell (hatched bar) and HaCaT stimulated with *P. acnes* (horizontal bar). Measurement of cell viability was realized by the MTT assay as described in Materials and Methods. Data are means±S.D. of three separate experiments.
Figure 11:
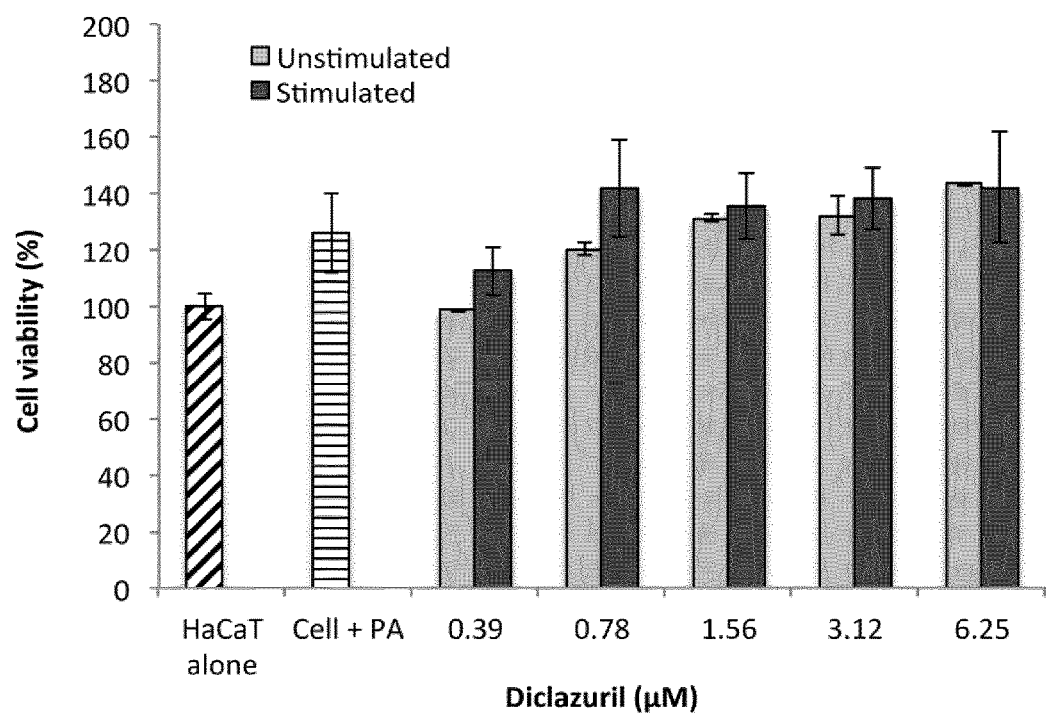

Both molecules, diclazuril and RCL PH000645-PH, were purchased from Sigma and tested independently on immortalized keratinocytes HaCaT cell for their capacity to inhibit the IL-8 production. HaCaT cells were pre-treated with RCL PH000645-PH and diclazuril (used as reference), at the concentrations ranging from 0.39 to 6.25 µM, for 24 h and then stimulated with *P. acnes* suspension as described in Materials and Methods. The production of IL-8 was measured on culture supernatant by ELISA (FIG. 10) and the viability of cells was estimated by the MTT assay (FIG. 11). We confirmed the inhibition of IL-8 production by diclazuril and shown that the analogue RCL PH000645-PH was able to inhibit the production of IL-8 in a dose-dependent manner with an IC50 at about 3 µM (P=0.000069) (FIG. 10A, B), while no change was observed in pretreated cells without being stimulated. In parallel we tested cell viability and shown no cytotoxicity at the IC50 concentration (FIG. 11).

10—Complementary Data for Chemical Meclozine Analogue Testing

Lidoflazine, GBR 12909 dihydrochloride, Chlorcyclizine hydrochloride and Lomerizine were purchased from Prestwick and tested independently on immortalized keratinocytes HaCaT cell for their capacity to inhibit the IL-8 production. HaCaT cells were pre-treated with Lidoflazine, GBR 12909 dihydrochloride, Chlorcyclizine hydrochloride and Lomerizine at the concentration of 10 µM, for 24 h and then stimulated with *P. acnes* suspension as described in Materials and Methods. The production of IL-8 was measured on culture supernatant by ELISA and the viability of cells was estimated by the MTT assay. The results are shown on Table 1 below.

TABLE 1

| Meclozine analogues | Dose-dependent inhibition of IL-8 production by keratinocytes stimulated by *P. acnes* pre-treated with meclozine analogues | Evaluation of cell viability after treatment with meclozine analogues on keratinocytes. |
| --- | --- | --- |
| Lidoflazine | 65% | 107% |
| GBR 12909 dihydrochloride, | 78% | 78% |
| Chlorcyclizine hydrochloride | 54% | 81% |
| Lomerizine | 58% | 95% |

We shown that the meclozine analogues Lidoflazine, GBR 12909 dihydrochloride, Chlorcyclizine hydrochloride and Lomerizine were able to inhibit the production of IL-8 ranging from 54 to 78% (Table 1). In parallel we tested cell viability and shown no (95, 107%) or very weak (78, 81%) cytotoxicity at 10 µM concentration (Table 1).

11—Complementary Data for In Vivo Inflammation Model Testing

According to previous results showing in vitro efficacy of both molecules on the anti-inflammatory response, we tested their capacity to inhibit the inflammatory reaction induced by *P. acnes* in an in vivo model of inflammation.

This model is based on the capacity of mouse ears to react while *P. acnes* is intradermally injected. The inflammatory reaction is evaluated each day over a period of 4 days after *P. acnes* injection by measuring the thickness of the ears, the redness as well as the presence of a desquamation and/or small pustules. At the end of the experiment, final measurement of inflammation was realized and photographic pictures of ears were taken. Then, mice were euthanized and ears were immediately fixed in a formalin-containing buffer for a future histological analysis.

The experimental design consisted of 3 groups containing 8 mice each. 1) PBS corresponds to the non-treated group injected with PBS. 2) PA+Vehicle corresponds to *P. acnes* injected in ears treated with the vehicle alone. 3) PA+meclozine corresponds to *P. acnes* injected in ears topically treated with 1% meclozine mixed with vehicle. The preparation of the 1% meclozine gel consisted of extemporaneously solubilizing 5 mg of meclozine in 150 µl of DMSO and in 300 µl of Solutol HS153070/water (30:70, w/w) to finally gently incorporated in 1.5 g of Vaseline for 1 min at room temperature (21° C.) and then directly applied to the mouse ears.

Figure 12:
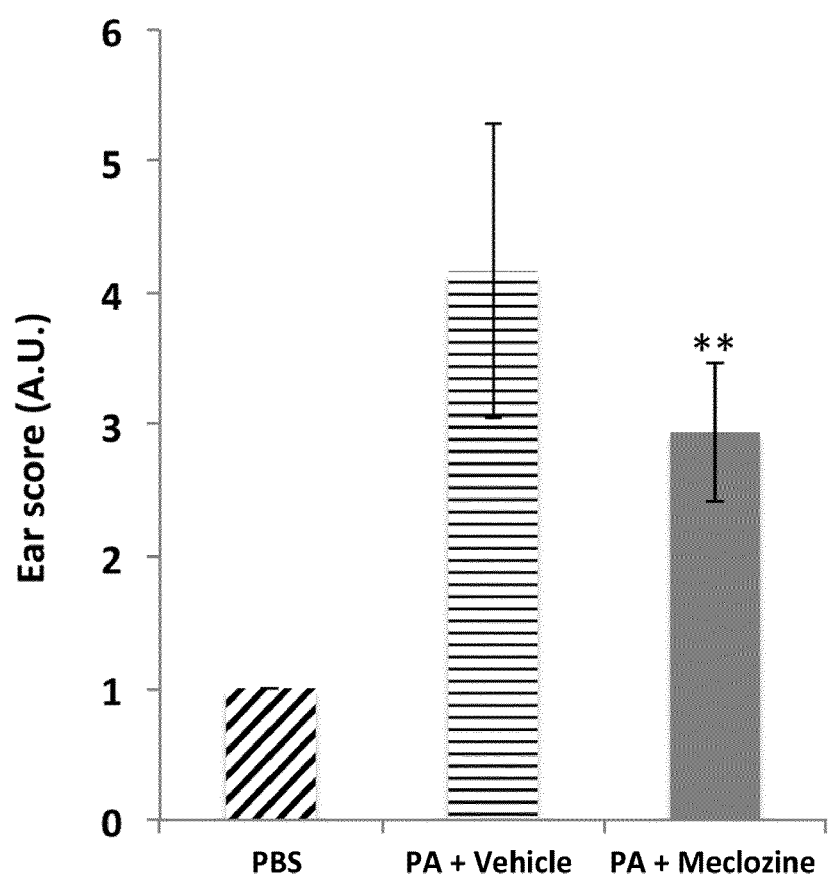
FIG. 12: Effect of Meclozine on *P. acnes*-induced inflammation in vivo. Ears of mice were intradermally injected with *P. acnes* ($OD_{620\,nm}$=1.0 corresponding to $2.10^7$ CFU/20 µl in PBS) to induce inflammation. Subsequently, 1% meclozine gel was applied on the ear skin surface of mice each day for 3 days. The score corresponding to the ear thickness, the peeling and the redness, was measured every day for a period of 96 h. Data are means±S.D. of 8 individual experiments. PBS corresponds to the non-treated group injected with PBS. PA+Vehicle corresponds to *P. acnes* injected in ears treated with Vaseline containing DMSO (150 µl), Solutol HS153070/water (30:70, w/w) (300 µl). PA+meclozine corresponds to *P. acnes* injected in ears treated with 1% meclozine mixed with Vaseline containing DMSO (150 µl), Solutol HS153070/water (30:70, w/w) (300 µl). Statistical significance is indicated by * ($P<0.05$), ** ($P<0.01$).
Figure 13:
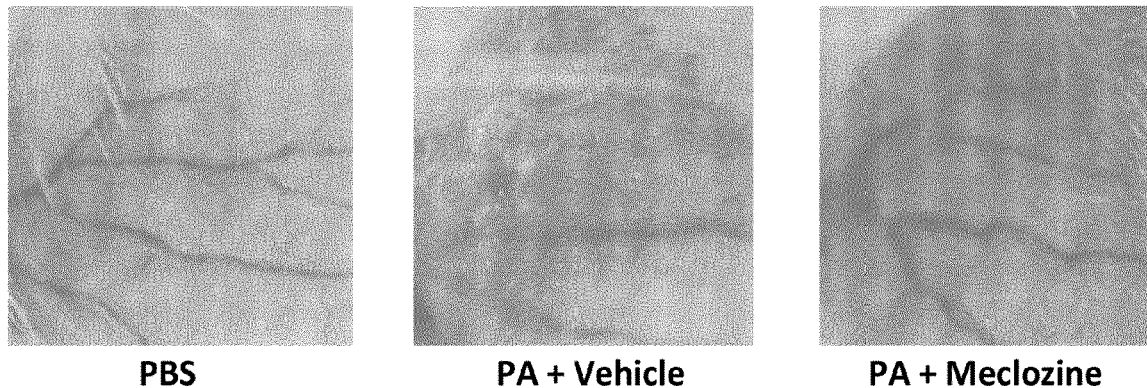
FIG. 13: Effect of Meclozine topical application on *P. acnes*-induced inflammation in vivo. Ears of mice were intradermally injected with *P. acnes* ($OD_{620\,nm}$=1.0 corresponding to $2.10^7$ CFU/20 µl in PBS) to induce inflammation. Subsequently, 1% meclozine gel was applied on the ear skin surface of mice each day for 3 days. PBS corresponds to the non-treated group injected with PBS. PA+Vehicle corresponds to *P. acnes* injected in ears treated with Vaseline containing DMSO (150 µl), Solutol HS153070/water (30:70, w/w) (300 µl). PA+meclozine corresponds to *P. acnes* injected in ears treated with 1% meclozine mixed with Vaseline containing DMSO (150 µl), Solutol HS153070/water (30:70, w/w) (300 µl).
Figure 14:
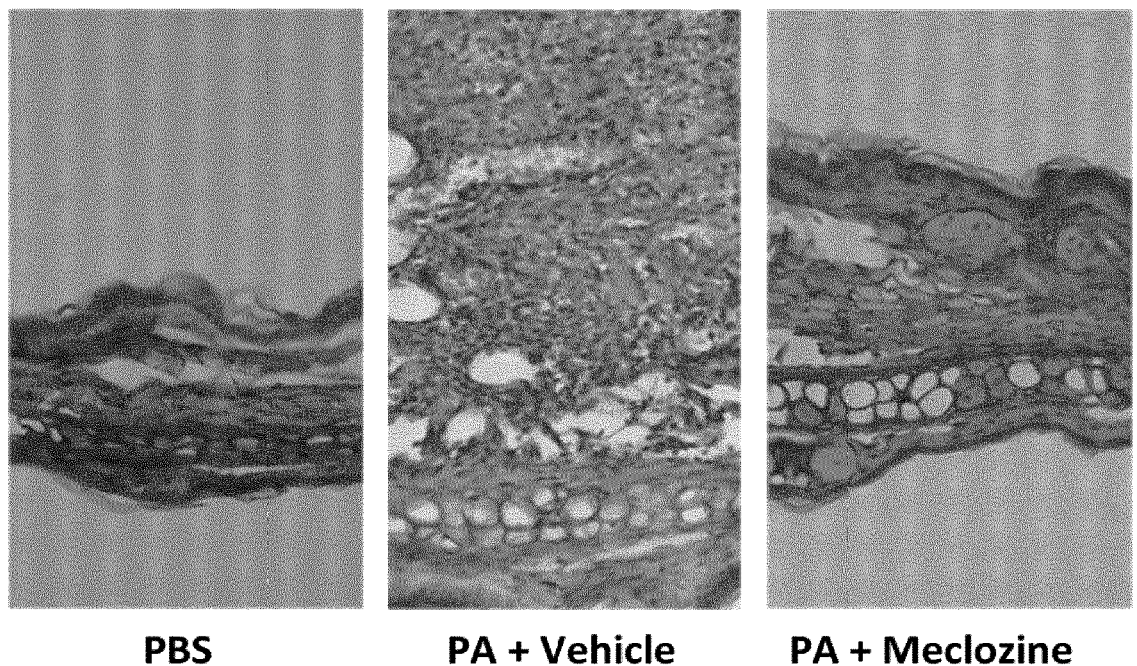
FIG. 14: Histopathological analysis of mouse ears. Ears of mice were intradermally injected with *P. acnes* ($OD_{620\,nm}$=1.0 corresponding to $2.10^7$ CFU/20 µl in PBS) to induce inflammation. Subsequently, 1% meclozine gel was applied on the ear skin surface of mice each day for 3 days. Ears were formalin-fixed and embedded in paraffin. Detection of cells was made by hematoxylin and eosin staining PBS corresponds to the non-treated group injected with PBS. PA+Vehicle corresponds to *P. acnes* injected in ears treated with Vaseline containing DMSO (150 µl), Solutol HS153070/water (30:70, w/w) (300 µl). PA+meclozine corresponds to *P. acnes* injected in ears treated with 1% meclozine mixed with Vaseline containing DMSO (150 µl), Solutol HS153070/water (30:70, w/w) (300 µl).

We have shown that meclozine is able to decrease the ear inflammation in topical application by 29.5% (FIG. 12) as it is shown in the ears pictures (FIG. 13). Histological analysis revealed an increase in ear thickness and an important leukocyte infiltration in the *P. acnes* injected-ears (FIG. 14, panel PA+Vehicle) comparing to negative control (FIG. 14, Panel PBS). When ears were treated with meclozine, the ear thickness decrease as well as the leukocyte infiltration (FIG. 14, Panel PA+Meclozine).

12—Complementary Data for Signalling Pathways Analysis

Diclazuril and meclozine modulation of inflammatory-related pathways. We investigated the molecular basis for the inhibition of IL-8 production by diclazuril and meclozine, in particular we evaluated if both molecules interfered with inflammatory-related signalling pathways as well as cell adhesion- and lipids-related pathways known to be activated when keratinocytes are stimulated with *P. acnes*.

We shown that the activation of HaCaT keratinocytes by *P. acnes* led to the transcient p-IκB degradation while IκB was steady. Pre-treating HaCaT keratinocytes with diclazuril and meclozine before *P. acnes* stimulation did not alter the degradation of p-IκB.

Figure 15:
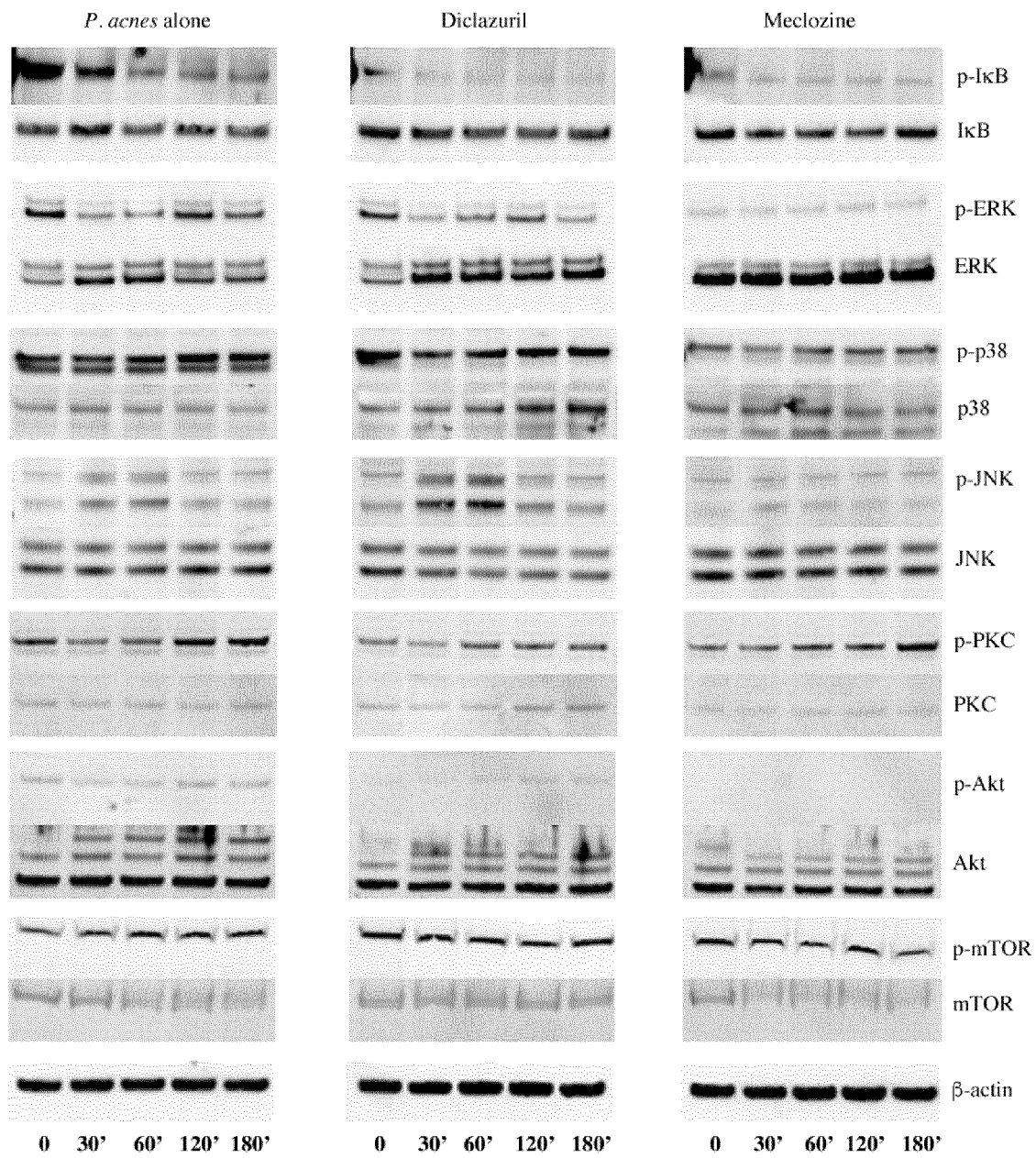
FIG. 15: Diclazuril and meclozine inhibit inflammatory signaling pathways. HaCaT cells were pre-treated for 24 h with diclazuril and meclozine at 25 µM and then stimulated with *P. acnes* for 30, 60, 120, 180 min and 18, 24 h. At each time whole-cell lysates were prepared and used for p-IκB/IκB, p-ERK/ERK, p-p38/p38, p-JNK/JNK, p-PKC/PKC, p-Akt/Akt, p-mTOR/mTOR western blot analysis, using the appropriate antibodies. Protein load (25 µg protein per lane) was assessed by using β-actin.
Figure 16:
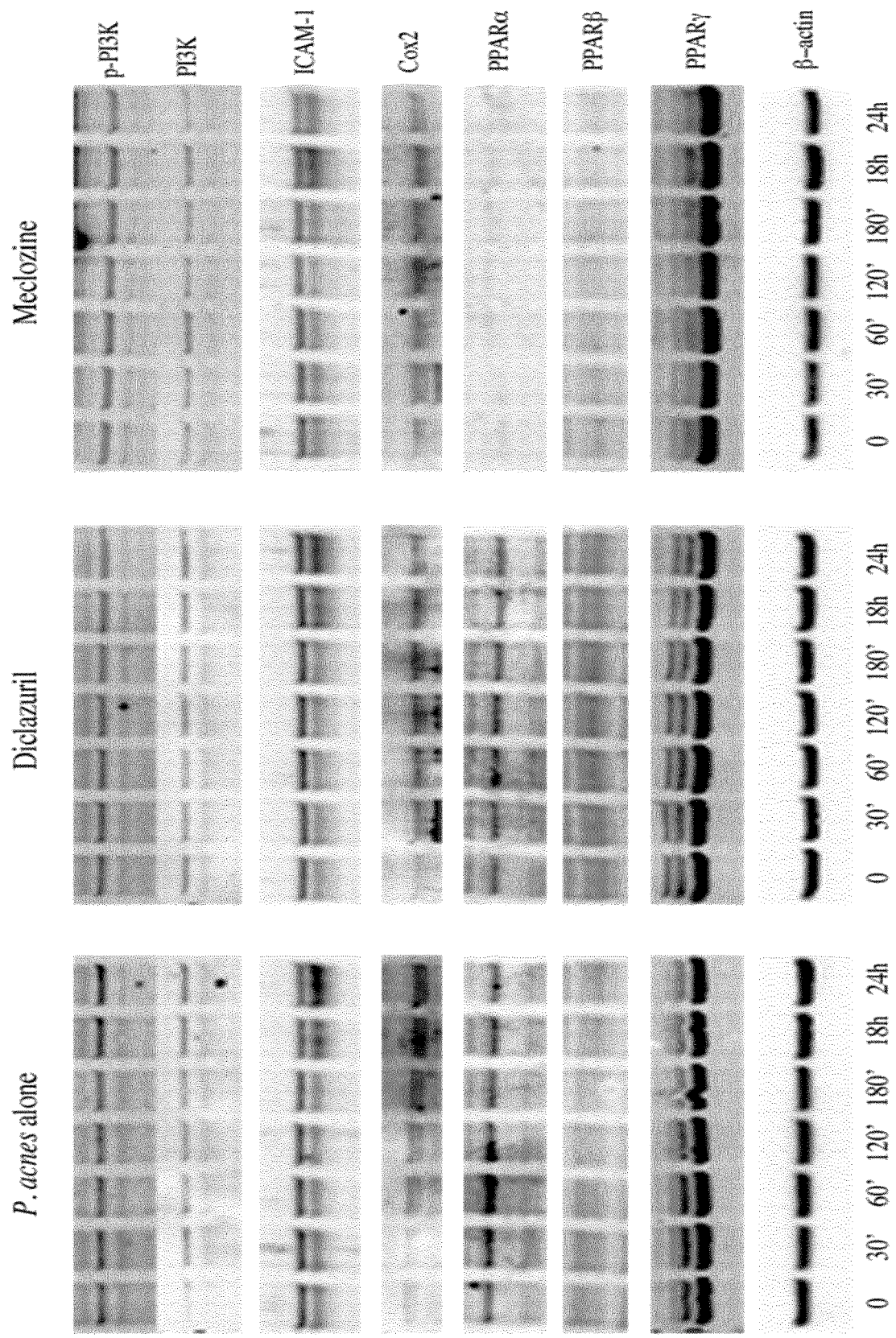
FIG. 16: Diclazuril and meclozine inhibit inflammatory signaling pathways. HaCaT cells were pre-treated for 24 h with diclazuril and meclozine at 25 µM and then stimulated with *P. acnes* for 30, 60, 120, 180 min and 18, 24 h. At each time whole-cell lysates were prepared and used for p-PI3K/PI3K, ICAM-1, Cox2, PPAR alpha, PPAR beta, PPAr gamma western blot analysis, using the appropriate antibodies. Protein load (25 µg protein per lane) was assessed by using β-actin.

We also shown that the activation of HaCaT keratinocytes by *P. acnes* led to the activation of p-ERK, p-p38, p-JNK, p-PKC, p-Akt, p-mTOR (FIG. 15, panel *P. acnes* alone) and p-PI3K (FIG. 16, panel *P. acnes* alone). However, both molecules prevented the phosphorylation of ERK-, p38-, PKC-, Akt-, and PI3K-induced by *P. acnes*, while they did not cause any changed in the phosphorylation of JNK-, and mTOR-induced *P. acnes* (FIGS. 15 and 16, panels diclazuril and meclozine). Interestingly, diclazuril was able to inhibits the phosphorylation of PKC and PI3K stronger than meclozine while meclozine hah a stronger effect on the inhibition of the phosphorylation of Akt. Stripping and subsequent reprobing of the blot with antibodies against total IκB, ERK, p38, JNK, PKC, Akt, mTOR, and PI3K demonstrated no change in total protein levels following *P. acnes* stimulation, suggesting that *P. acnes* activated pre-existing all of these proteins (FIGS. 15 and 16).

These data suggested that the inhibition by diclazuril and meclozine of *P. acnes*-induced IL-8 production in keratinocytes involves downregulation of the MAPK, PKC, Akt and PI3 kinase pathways.

Diclazuril and meclozine modulation of adhesion molecules- and lipids-related pathways. We investigated the up-regulation of adhesion molecules onto keratinocytes which play subsequently an important role in the infiltration of leukocytes into the skin during the inflammation reaction. Stimulating HaCaT keratinocytes by *P. acnes* increase the expression of the intercellular adhesion molecule-1 (ICAM-1). Pre-treating HaCaT cells with diclazuril had no effect on the *P. acnes*-induced ICAM-1 expression while meclozine decreased its expression (FIG. 16). Inflammatory acne is a multifactorial disease of the pilosebaceous unit where lipids and fatty acids present in sebum induced an inflammation reaction as well. Increase sebum production is essential to the development of acne and its serves as a nutrient source for *P. acnes*. It has been shown that the peroxisome-proliferator activated receptors (PPARs) influence lipid catabolism by increasing sebum production and are important mediators of inflammatory responses as well as prostaglandins (PG) induced by the activation of the cyclooxygenase (Cox-2) gene expression (Tsai 2013, Gupta 2015). We then analysed the expression of these markers (PPARs and Cox-2) and shown that the *P. acnes*-induced keratinocytes increase the expression of Cox-2, PPARα and PPARβ and no significant change in PPARγ expression. Pre-treating HaCaT cells with diclazuril decrease the expression of Cox-2 and no change for the PPARs expression. On the other hand, meclozine treatment strongly decrease the expression of Cox-2 as well as for the PPARα and PPARβ (FIG. 7)

These data suggested that diclazuril inhibited weakly the ICAM-1 and the Cox-2/PPARs expressions, while meclozine had a stronger inhibitory capacity.

13—Complementary Data for Psoriasis Testing

To assess the meclozine and diclazuril anti-inflammatory activities on psoriasis, we used an in vitro model of normal human epidermal keratinocytes (NHDK) stimulated by a pro-inflammatory mixture M5 mimicking a psoriasis-like phenotype. We then evaluated the meclozine and diclazuril abilities to inhibit the release of IL-8 and of β-defensin-2 protein (hBD-2) by the keratinocytes stimulated in this condition (Rabeony et al., 2014).

Figure 17:
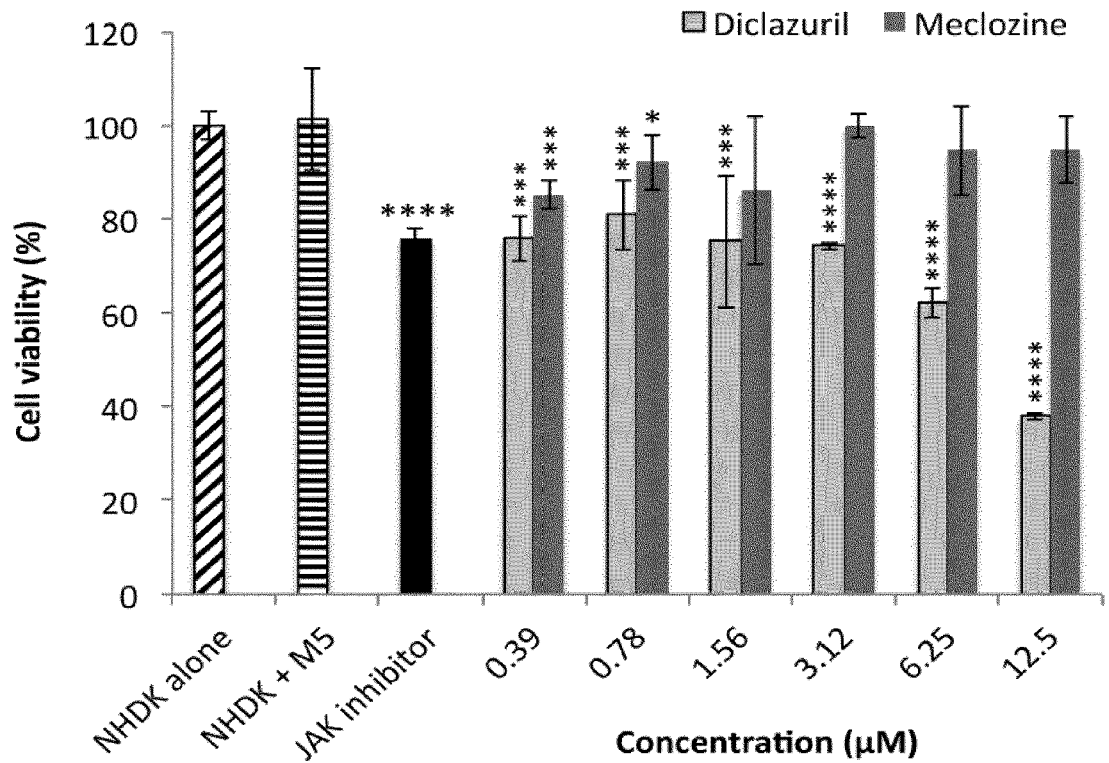
FIG. 17: Evaluation of keratinocyte viability after treatment with meclozine and diclazuril in the in vitro psoriasis-like model. Human cutaneous primary keratinocytes (NHDK) were stimulated by the solution M5 consisting by a combination of IL-17A, OSM, TNF-α, IL-22, IL-1□ (10 ng/ml) and treated for 48 h with JAK inhibitor at 6.25 µM (positive control) or meclozine and diclazuril at concentrations ranging from 0.39 to 12.5 µM. Control experiments were done with untreated unstimulated NHDK cells (NHDK alone) and untreated NHDK stimulated by M5 (NHDK+M5). Measurement of cytotoxicity was determined by the MTT assay as described in the Materials and Methods. Data are means±S.D. of three individual experiments. Statistical significance (versus NHDK alone) is indicated by * ($P<0.05$),  ($P<0.01$), and * ($P<0.001$), respectively.

The M5 stimulation on primary keratinocytes had no deleterious effect on cell viability. When cells are pre-treated with the JAK inhibitor we observed a decrease by 24.4% of the cell viability. Pre-treatment of cells with meclozine decrease the cell viability by 0.14 to 15%, while pre-treatment with diclazuril decrease the cell viability by 20 to 62% (FIG. 17).

Figure 18:
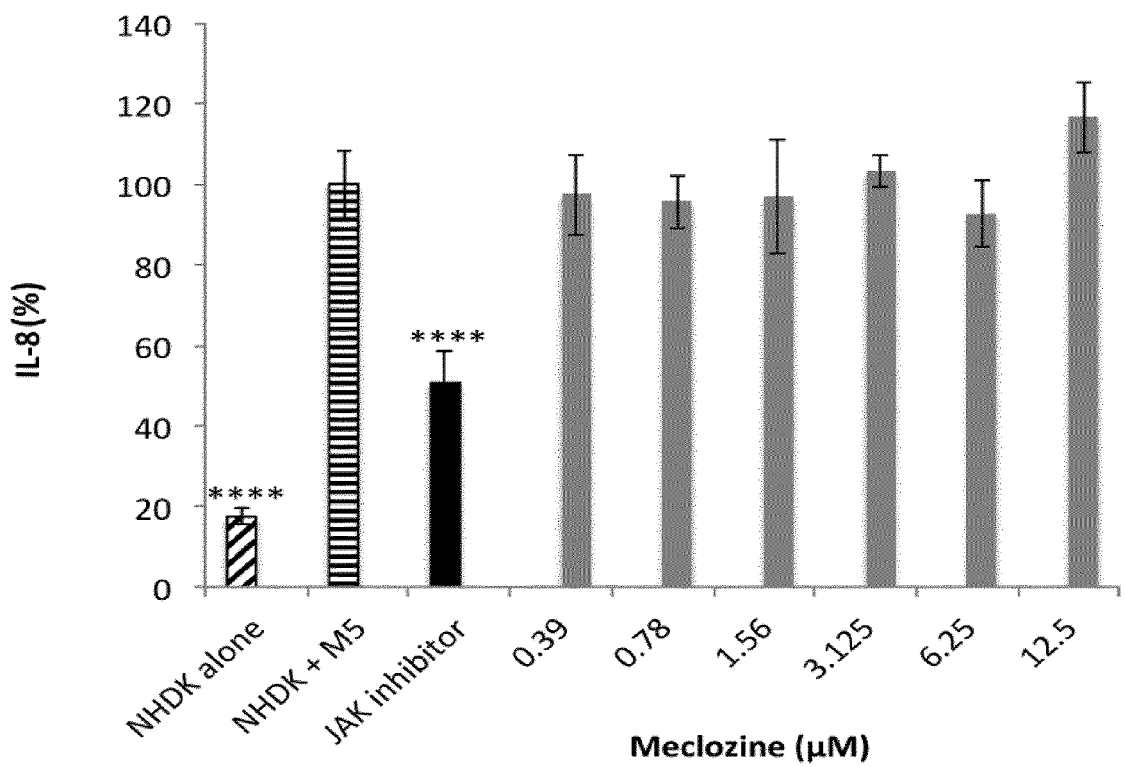
FIG. 18: IL-8 production by meclozine-treated keratinocytes in the in vitro psoriasis-like model. Human cutaneous primary keratinocytes (NHDK) were stimulated by the solution M5 consisting by a combination of IL-17A, OSM, TNF-α, IL-22, IL-1α (10 ng/ml) and treated for 48 h with JAK inhibitor at 6.25 µM (positive control) or meclozine and diclazuril at concentrations ranging from 0.39 to 12.5 µM. Control experiments were done with untreated unstimulated NHDK cells (NHDK alone) and untreated NHDK stimulated by M5 (NHDK+M5). Measurement of IL-8 was realized by ELISA as described in the Materials and Methods. Data are means±S.D. of three individual experiments. Statistical significance (versus NHDK+M5) is indicated by **** ($P<0.0001$).
Figure 19:
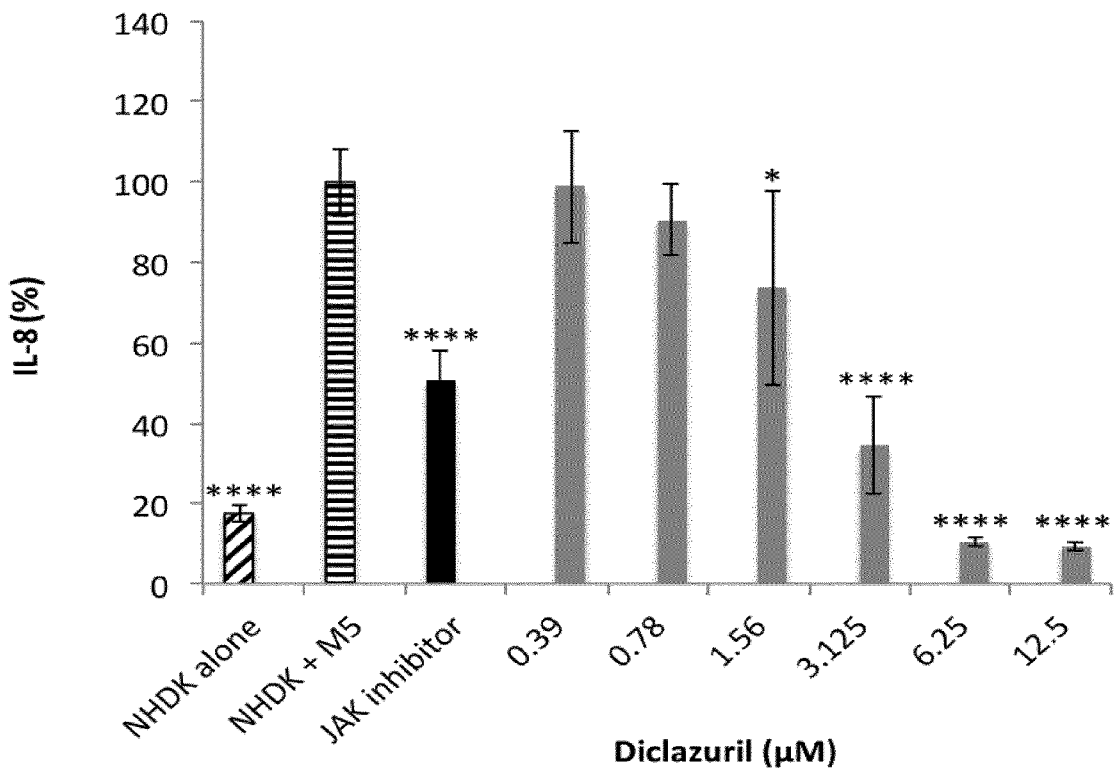
FIG. 19: Inhibition of IL-8 production by diclazuril in the in vitro psoriasis-like model. Human cutaneous primary keratinocytes (NHDK) were stimulated by the solution M5 consisting by a combination of IL-17A, OSM, TNF-α, IL-22, IL-1 α (10 ng/ml) and treated for 48 h with JAK inhibitor at 6.25 µM (positive control) or meclozine and diclazuril at concentrations ranging from 0.39 to 12.5 µM. Control experiments were done with untreated unstimulated NHDK cells (NHDK alone) and untreated NHDK stimulated by M5 (NHDK+M5). Data are means±S.D. of three individual experiments. Statistical significance (versus NHDK+M5) is indicated by **** ($P<0.0001$).

Meclozine and diclazuril activity on IL-8 production. In basal conditions, normal human epidermal keratinocytes (NHDK) produced a small amount of IL-8. The IL-8 production was greatly increased by the stimulation with the combination of 5 cytokines. The reference Jak Inhibitor I (positive control) moderately inhibited the stimulating effect of this association (49% inhibition) (FIGS. 18 and 19). Under the experimental conditions of this study, meclozine had no effect on the IL-8 production (FIG. 18) while diclazuril decreased the IL-8 production in a dose-dependent manner with an IC50 around 2-3 µM with a decrease by 66% at 3,125 µM (FIG. 19).

Figure 20:
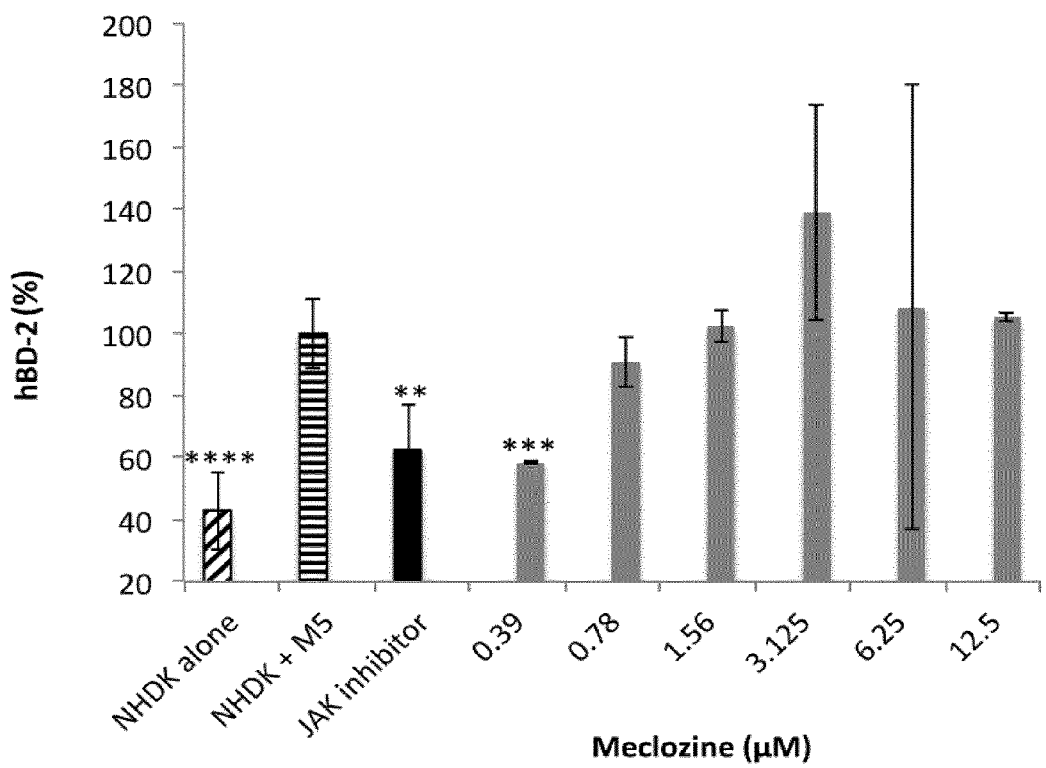
FIG. 20: hBD-2 production by meclozine-treated keratinocytes in the in vitro psoriasis-like model. Human cutaneous primary keratinocytes (NHDK) were stimulated by the solution M5 consisting by a combination of IL-17A, OSM, TNF-α, IL-22, IL-1α (10 ng/ml) and treated for 48 h with JAK inhibitor at 6.25 µM (positive control) and meclozine at concentrations ranging from 0.39 to 12.5 µM. Control experiments were done with untreated unstimulated NHDK cells (NHDK alone) and untreated NHDK stimulated by M5 (NHDK+M5). Data are means±SD. of three individual experiments. Statistical significance is indicated by  ($P<0.01$), * ($P<0.001$) and **** ($P<0.0001$), respectively.
Figure 21:
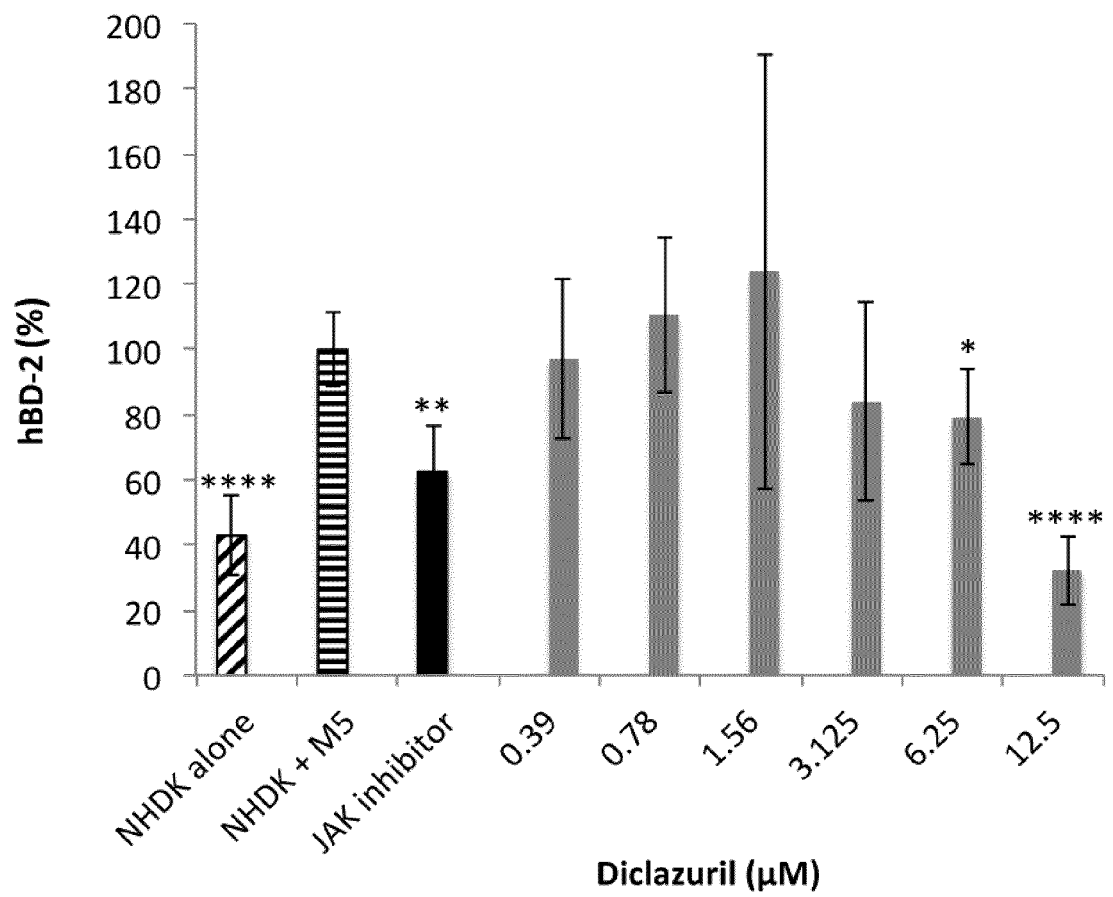
FIG. 21: Inhibition of hBD-2 production by diclazuril in the in vitro psoriasis-like model. Human cutaneous primary keratinocytes (NHDK) were stimulated by the solution M5 consisting by a combination of IL-17A, OSM, TNF-α, IL-22, IL-1α (10 ng/ml) and treated for 48 h with JAK inhibitor at 6.25 µM (positive control) and diclazuril at concentrations ranging from 0.39 to 12.5 µM. Control experiments were done with untreated unstimulated NHDK cells (NHDK alone) and untreated NHDK stimulated by M5 (NHDK+M5). Data are means±S.D. of three individual experiments. Statistical significance is indicated by  ($P<0.01$), and ** ($P<0.0001$), respectively.

Meclozine and diclazuril activities on hBD-2 production. In basal conditions, normal human epidermal keratinocytes released a very small amount of β-defensin-2 protein (hBD-2). The hBD-2 production was greatly increased by the treatment with the combination of Il-17, TNF-α and OSM. The reference Jak Inhibitor I (positive control) inhibited the stimulating effect of this association (38% inhibition) (FIGS. 20 and 21). Under the experimental conditions of this study, meclozine had no effect on the hBD-2 production (FIG. 20) while diclazuril decreased the hBD-2 production in a dose-dependent manner with a decrease by 68% at 12.5 µM (FIG. 21).

REFERENCES

Achermann, Y., E. J. C. Goldstein, T. Coenye, M. E. Shirtliff. 2014. *Propionibacterium acnes*: from commensal to opportunistic biofilm-associated implant pathogen. Clinical Microbiology Reviews. 27:419-440.

Brüggemann, H., A. Henne, F. Hoster, H. Liesegang, A. Wiezer, A. Strittmatter, S. Hujer, P. Dürre, G. Gottschalk. 2004. The complete genome sequence of *Propionibacterium acnes*, a commensal of human skin. Science. 305: 671-673.

Graham G. M., M. D. Farrar, J. E. Cruse-Sawyer, K. T. Holland, E. Ingham. 2004. Proinflammatory cytokine production by human keratinocytes stimulated with *Propionibacterium acnes* and *P. acnes* GroEL. Br. J. Dermatol. 150:421-428.

Grange, P. A., C. Chéreau, J. Raingeaud, C. Nicco, B. Weill, N. Dupin, F. Batteux. 2009a. Production of superoxide anions by keratinocytes initiates *P. acnes*-induced inflammation of the skin. PLoS Pathog. 5(7): e1000527. doi: 10.1371/journal.ppat.1000527

Grange, P. A., J. Raingeaud, V. Calvez, N. Dupin. 2009b. Nicotinamide inhibits *Propionibacterium acnes*-induced IL-8 production in keratinocytes through the NF-kappaB and MAPK pathways. J Dermatol. Sci. 56:106-112.

Gupta M, Mahajan V K, Mehta K S, Chauhan P S, Rawat R. (2015) Peroxisome proliferator-activated receptors (PPARs) and PPAR agonists: the 'futur' in dermatology therapeutics? Arch Dermatol Res 307:767-780.

Jugeau, S., I. Tenaud, A. C. Knol, V. Jarrousse, G. Quereux, A. Khammari, B. Dreno. 2005. Induction of toll-like receptors by *Propionibacterium acnes*. Br. J. Dermatol. 153:1105-1113.

Kistowska, M., S. Gehrke, D. Jankovic, K. Kerl, A. Fettelschoss, L. Feldmeyer, G. Fenini, A. Kolios, A. Navarini, R. Ganceviciene, J. Schauber, E. Contassot, L. E. French. 2014 IL-1β drives inflammatory responses to *Propionibacterium acnes* in vitro and in vivo. J. Invest. Dermatol. 134:677-685.

McDowell, A., I. Nagy, M. Magyari, E. Barnard, S. Patrick. 2013. The opportunistic pathogen *Propionibacterium acnes*: Insights into typing, human disease, clonal diversification and CAMP factor evolution. PLoS ONE 8(9): e70897. Doi:10.1371/journal.pone.0070897.

Nagy, I., A. Pivarcsi, A. Koreck, M. Széll, E. Urbán, and L. Kemény. 2005. Distinct strains of *Propionibacterium acnes* induce selective human □-defensin-2 and interleukin-8 expression in human keratinocytes through Toll-like receptors. J. Invest. Dermatol. 124:931-938.

Rabeony H, Petit-Paris I, Gamier J, Barrault C, Pedretti N, Guilloteau K, Jegou J F, Guillet G, Huguier V, Lecron J C, Bernard F X, Morel F. (2014) Inhibition of keratinocyte differentiation by the synergistic effect of IL-17A, IL-22, IL-1a, TNFa and oncostatin M. PLoS ONE 9(7): e101937.

Trivedi, N. R., K. L. Gilliland, W. Zhao, W. Liu, D. M. Thiboutot. 2006. Gene array expression profiling in acne lesions reveals marked upregulation of genes involved in inflammation and matrix remodeling. J. Invest. Dermatol. 126:1071-1079.

Tsai H H, Lee W R, Wang P H, Cheng K T, Chen Y C, Shen S C. (2013). (2013) *Propionibacterium acnes*-induced iNOS and COX-2 protein expression via ROS-dependent NF-kB and AP-1 activation in macrophages. J Dermatol Sci 69: 122-131.

---

The invention claimed is:

1. A method for treating disorders associated to the inflammation induced by *P. acnes* comprising administering to a subject in need thereof an effective amount of a compound of following general formula (II):

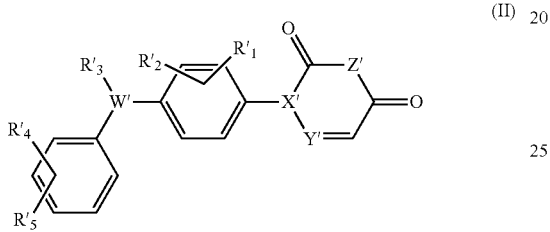

or a pharmaceutically acceptable salt and/or solvate thereof, wherein:

X', Y' and Z' are, independently of one another, CH, CH$_2$, NH or N;

W' is CHR'3, S=O or S;

R'$_1$ and R'$_2$ are, independently of one another, hydrogen atom, halo, —CN, —NO$_2$, —CF$_3$, —OR'$_7$, —NR'$_8$R'$_9$, or a (C$_1$-C$_6$)alkyl group;

R'$_3$ is H, —CN, OR'$_{10}$, or a (C$_1$-C$_6$)alkyl group;

R'$_4$ and R'$_5$, are, independently of one another, hydrogen atom or a group selected from halo, —NO$_2$, —CN, —OR'$_{11}$, —NR'$_{12}$R'$_{13}$, —C(O)OR'$_{14}$, —S(O)$_2$R'$_{15}$, or a (C$_1$-C$_6$)alkyl group optionally substituted with one or several groups selected from halo or —OR'$_{16}$;

R'$_7$ to R'$_{16}$ are, independently of one another, hydrogen atom or a group selected from (C$_1$-C$_6$)alkyl, aryl, (C$_1$-C$_6$)alkyl-aryl, heterocycle, (C$_1$-C$_6$)alkyl-heterocycle, said group being optionally substituted with one or several groups selected from halo, (C$_1$-C$_6$) alkyl, CF$_3$ or —OR'$_{17}$;

R'$_{17}$ is hydrogen atom, halo or a (C$_1$-C$_6$)alkyl group.

2. The method of claim 1, wherein said compound is a compound of the following general formula (IIa):

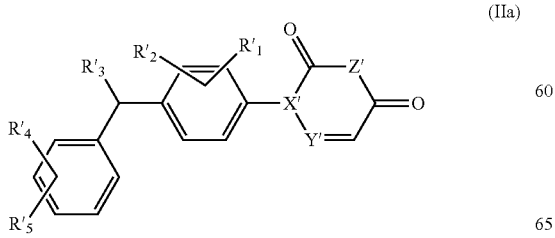

or a pharmaceutically acceptable salt and/or solvate thereof, wherein:

X', Y' and Z' are, independently of one another, CH, CH$_2$, NH, or N;

R'$_1$ and R'$_2$ are, independently of one another, hydrogen atom, halo, —CN, —NO$_2$, —CF$_3$, —OR'$_7$, —NR'$_8$R'$_9$, or a (C$_1$-C$_6$)alkyl group;

R'$_3$ is H, —CN, OR'$_{10}$, or a (C$_1$-C$_6$)alkyl group;

R'$_4$ and R'$_5$, are, independently of one another, hydrogen atom or a group selected from halo, —NO$_2$, —CN, —OR'$_{11}$, —NR'$_{12}$R'$_{13}$, —C(O)OR'$_{14}$, —S(O)$_2$R'$_{15}$, or a (C$_1$-C$_6$)alkyl group optionally substituted with one or several groups selected from halo or —OR'$_{16}$;

R'$_7$ to R'$_{16}$ are, independently of one another, hydrogen atom, or a group selected from (C$_1$-C$_6$)alkyl, aryl, (C$_1$-C$_6$)alkyl-aryl, heterocycle, (C$_1$-C$_6$)alkyl-heterocycle, said group being optionally substituted with one or several groups selected from halo, (C$_1$-C$_6$) alkyl, CF$_3$ or —OR'$_{17}$;

R'$_{17}$ is hydrogen atom, halo or a (C$_1$-C$_6$)alkyl group.

3. The method of claim 1, wherein X', Y', and Z' are each a nitrogen atom.

4. The method of claim 1, wherein R'$_3$ is —CN, or OH.

5. The method of claim 1, wherein and R'$_1$ and R'$_2$ are, independently of one another, hydrogen atom, halo, —CF$_3$, —OH, or a (C$_1$-C$_6$)alkyl group.

6. The method of claim 1, wherein R'$_5$ is an hydrogen atom and R'$_4$ is selected from the group consisting of hydrogen atom, halo, —CF$_3$, —OH, and a (C$_1$-C$_6$)alkyl group.

7. The method of claim 1, wherein said compound is a compound of the following general formula (IIb):

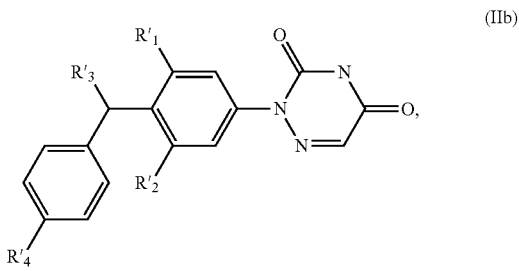

or a pharmaceutically acceptable salt and/or solvate thereof.

8. The method of claim 1, wherein said compound is a compound of the following formula (IId):

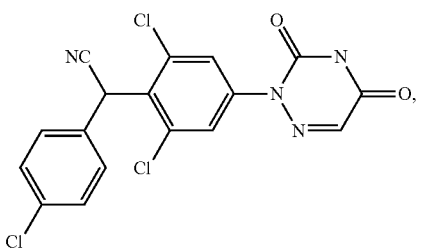

(IId)

or a pharmaceutically acceptable salt and/or solvate thereof.

9. The method of claim 1, wherein said disorders associated to the inflammation induced by *P. acnes* are acne, psoriasis, chronic urticaria, urticaria pigmentosa, cutaneous autoinflammatory diseases, hidradenitis, or atopic dermatis.

10. A method for treating disorders associated to the inflammation induced by *P. acnes* comprising administering to a subject in need thereof an effective amount of a pharmaceutical composition comprising at least one compound of claim 1 and at least one pharmaceutically acceptable excipient.

11. The method of claim 10, wherein said composition further comprises another active principle selected from the group consisting of a topical antibiotic, topical anti-inflammatory, topical anti-seborrheic zinc derivative, cyclin, and isotretinoin.

12. The method of claim 10, wherein said composition further comprises another active principle selected from the group consisting of erythromycine, dalacine, benzoyl peroxyde derivatives, isotretinoin, tretinoin, adapalene, zinc gluconate, cyclins, and isotretinoin.

* * * * *

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: IL-8 sens primer

<400> SEQUENCE: 1
tcttggcagc cttcctgatt                                              20

<210> SEQ ID NO 2
<211> LENGTH: 19
<212> TYPE: DNA
<213> ORGANISM: Artificial Sequence
<220> FEATURE:
<223> OTHER INFORMATION: IL-8 antisens primer

<400> SEQUENCE: 2
tttcgtgttg gcgcagtgt                                               19

<210> SEQ ID NO 3
<211> LENGTH: 18
<212> TYPE: DNA
<213> ORGANISM: Artificial Sequence
<220> FEATURE:
<223> OTHER INFORMATION: GAPDH sens primer

<400> SEQUENCE: 3
gccacatcgc tcagacac                                                18

<210> SEQ ID NO 4
```

```
<211> LENGTH: 19
<212> TYPE: DNA
<213> ORGANISM: Artificial Sequence
<220> FEATURE:
<223> OTHER INFORMATION: GADPH anti-sens primer

<400> SEQUENCE: 4
gcccaatacg accaaatcc                                            19
```